United States Patent
Collingwood et al.

(10) Patent No.: US 8,236,808 B2
(45) Date of Patent: Aug. 7, 2012

(54) PYRAZINE DERIVATIVES AS ENAC BLOCKERS

(75) Inventors: Stephen Paul Collingwood, Horsham (GB); Nicholas James Devereux, Ash (GB); Catherine Howsham, Horsham (GB); Peter Hunt, Storrington (GB); Thomas Anthony Hunt, Croydon (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/995,647

(22) PCT Filed: Jun. 8, 2009

(86) PCT No.: PCT/EP2009/057060
§ 371 (c)(1),
(2), (4) Date: Apr. 27, 2011

(87) PCT Pub. No.: WO2009/150137
PCT Pub. Date: Dec. 17, 2009

(65) Prior Publication Data
US 2011/0201625 A1   Aug. 18, 2011

(30) Foreign Application Priority Data
Jun. 10, 2008   (EP) ..................................... 08157980

(51) Int. Cl.
*A61K 31/4965* (2006.01)
*C07D 241/20* (2006.01)
(52) U.S. Cl. .................................. 514/255.06; 544/407
(58) Field of Classification Search ............. 514/255.06; 544/407
See application file for complete search history.

(56) References Cited

U.S. PATENT DOCUMENTS 4,910,202 A * 3/1990 Schwartz ................. 514/255.06
2011/0059989 A1 * 3/2011 Collingwood et al. .. 514/255.05

OTHER PUBLICATIONS

Donaldson, Sodium Channels and Cystic Fibrosis, 2007, Chest, vol. 132, p. 1631-1636.*
Hummler, Genetic Disorders of Membrane Transport V. The epithelial sodium channel and its implication in human diseases, 1999, Am. J. Physiol. Gastrointest Liver Physiol, vol. 276, p. G567-G571.*

* cited by examiner

*Primary Examiner* — Golam M M Shameem
*Assistant Examiner* — Karen Cheng
(74) *Attorney, Agent, or Firm* — Mark W. Milstead

(57) ABSTRACT

A compound of Formula I

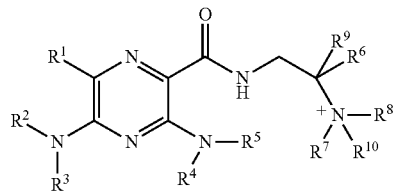

or a hydrate or solvate thereof, where $R^1$, $R^2$, $R^3$, $R^4$, $R^5$, $R^6$, $R^7$, $R^8$, $R^9$, and $R^{10}$ have the meanings as indicated in the specification, is useful for treating diseases which respond to the blockade of the epithelial sodium channel. Pharmaceutical compositions that contain the compounds and processes for preparing the compounds are also described.

8 Claims, No Drawings

PYRAZINE DERIVATIVES AS ENAC BLOCKERS

This application is a U.S. National Phase filing of International Application Serial No. PCT/EP2009/057060 filed 8 Jun. 2009 and claims priority to European Patent Application No. 08157980.7 filed 10 Jun. 2008; the contents of each of these applications are incorporated herein by reference in their entirety.

This invention relates to organic compounds, their preparation and use as pharmaceuticals.

In one aspect, the invention provides compounds according to Formula I:

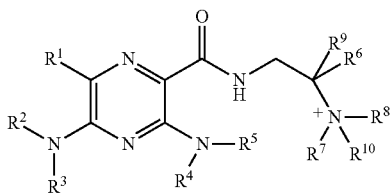

or solvates or hydrates thereof, wherein $R^1$ is halogen;

$R^2$, $R^3$, $R^4$ and $R^5$ are each independently selected from H and $C_1$-$C_6$ alkyl;

$R^6$ is —($C_0$-$C_6$ alkylene)-$R^{6a}$, wherein the alkylene linker is optionally substituted by one or more groups selected from $C_1$-$C_3$ alkyl, halo and OH;

$R^{6a}$ is selected from H, a $C_3$-$C_{10}$ carbocyclic group, $NR^{11}R^{12}$, $C(O)NR^{13}R^{14}$, aryl, heteroaryl, heterocyclyl and a group of the formula P—$(CH_2)_m$-Q, wherein each of the ring systems is optionally substituted by one or more substituents selected from the List Z;

P is selected from a bond, —O—, —C(O)—, —C(O)O—, —NHC(=N)NH— and —S($O_2$)—, —S($O_2$)$NR^a$—, —$NR^a$C(O)—, —$NR^a$C(O)O—, —$NR^a$S($O_2$)— and —$NR^a$C(O)$NR^b$—;

$R^a$ and $R^b$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

Q is selected from H, $C_1$-$C_6$ alkyl, a $C_3$-$C_{10}$ carbocyclic group, aryl, heteroaryl and heterocyclyl, wherein the carbocyclic, aryl, heteroaryl and heterocyclyl groups are each optionally substituted by one or more substituents selected from List Z;

m is 0, 1, 2 or 3;

$R^7$, $R^8$ and $R^{10}$ are each independently selected from $C_1$-$C_6$ alkyl, $C_2$-$C_6$ alkenyl, $C_2$-$C_6$ alkynyl, a $C_3$-$C_{10}$ carbocyclic group, —($C_1$-$C_3$ alkylene)-$C_3$-$C_{10}$ carbocyclic group, aryl, heteroaryl, heterocyclyl or a group of the formula $(CH_2)_d$-A-$(CH_2)_b$—B, wherein the carbocyclic, aryl, heteroaryl and heterocyclyl groups are each optionally substituted by one or more substituents selected from List Z; and wherein the alkyl and alkylene groups are optionally substituted by one or more halogen atoms, OH groups or phenyl groups; or $R^7$ and $R^8$, together with the nitrogen atom to which they are attached form a 4- to 10-membered nitrogen-containing heterocyclic group which is optionally substituted by one or more substituents selected from the List Z; or $R^6$ and $R^8$, together with the atoms to which they are attached form a 4- to 10-membered nitrogen-containing heterocyclic group which is optionally substituted by one or more substituents selected from the List Z;

A is selected from a bond, —O—, —C(O)—, —C(O)$NR^c$—, —C(O)O—, —OC(O)—, —NHC(=N)NH—, —S($O_2$)—, —S($O_2$)$NR^c$—, —$NR^c$C(O)—, —$NR^c$C(O)O—, —OC(O)$NR^c$—, —$NR^c$S($O_2$)—, —C(O)$NR^c$S($O_2$)—, —$NR^c$C(O)$NR^d$—, —$NR^2$—, -aryl-, —$C_3$-$C_{10}$ carbocyclyl-, -heteroaryl-, -heterocyclyl-, -aryl-O—, —O-aryl-, —O—$C_3$-$C_{10}$ carbocyclyl- and —$C_3$-$C_{10}$ carbocyclyl-O—, wherein the aryl, carbocyclyl, heteroaryl and heterocyclyl groups are each optionally substituted by one or more substituents selected from List Z;

B is selected from H, $C_1$-$C_6$ alkyl, a $C_3$-$C_{10}$ carbocyclic group, $NR^xR^y$, $C(O)OR^z$, aryl, heteroaryl and heterocyclyl, wherein the carbocyclic, aryl, heteroaryl and heterocyclyl groups are each optionally substituted by one or more substituents selected from List Z;

d is 1, 2, 3, 4, 5, 6 or 7;

b is 0, 1, 2 or 3;

$R^c$, $R^d$, $R^x$ and $R^y$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

$R^z$ is H or $C_1$-$C_6$ alkyl;

$R^9$ is H or $C_1$-$C_6$ alkyl; or $R^6$ and $R^9$, together with the carbon atom to which they are attached, form a $C_3$-$C_{10}$ carbocyclic group or a 4- to 10-membered heterocyclyl group, wherein each of the ring systems is optionally substituted by one or more substituents selected from the List Z;

$R^{11}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{12}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —C(O)$C_1$-$C_6$ alkyl, —C(O)$C_3$-$C_{10}$ carbocyclic, —C(O)($C_1$-$C_3$ alkylene)-$C_3$-$C_{10}$ carbocyclic, —C(O)$(CH_2)_x$ aryl, —C(O)$(CH_2)_x$ heteroaryl, —C(O)$(CH_2)_x$ heterocyclyl, —C(O)Oalkyl, C(O)Oaryl, $(CH_2)_x$ aryl, $(CH_2)_x$ heteroaryl and —$(CH_2)_x$ heterocyclyl, wherein each of the ring systems is optionally substituted by one or more substituents selected from the List Z;

$R^{13}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{14}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —$(CH_2)_z$ aryl, $(CH_2)_z$ heteroaryl and $(CH_2)_z$ heterocyclyl, wherein each of the ring systems is optionally substituted by one or more substituents selected from the List Z;

x is 0, 1, 2 or 3;

z is 0, 1, 2 or 3;

each Z is independently selected from OH, aryl, heteroaryl, heterocyclyl, benzyl, $C_1$-$C_6$ alkyl optionally substituted by one or more halogen atoms, CN or OH groups, $C_1$-$C_6$ alkoxy optionally substituted by one or more halogen atoms, CN or OH groups, -Oaryl, -Obenzyl, —O$(CH_2)_a$C(O)E, $NR^{15}$($SO_2$)$R^{17}$, ($SO_2$)$NR^{15}R^{16}$, ($SO_2$)$R^{18}$, $NR^{15}$C(O)$R^{17}$, C(O)$NR^{15}R^{17}$, $NR^{15}$C(O)$NR^{16}R^{17}$, $NR^{15}$C(O)O$R^{17}$, $NR^{15}R^{17}$, C(O)O$R^{15}$, OC(O)$R^{15}$, OC(O)$NR^{15}$, C(O)$R^{17}$, $SR^{15}$, CN, $NO_2$, and halogen; and when there are two or more Z substitutents, two Z substituents together with the atoms to which they are attached optionally form a 5- to 7-membered carbocyclic or a 4- to 7-membered heterocyclic substituent fused to the ring system;

a is 0, 1, 2, 3 or 4, where the alkylene group is optionally substituted by OH or $NH_2$ when a is 1, 2, 3 or 4;

E is $NR^{15}R^{17}$ or $OR^{17}$;

each $R^{15}$ and $R^{16}$ is independently selected from H, $C_1$-$C_6$ alkyl, a $C_3$-$C_{10}$ carbocyclic group and —($C_1$-$C_3$ alkylene)-$C_3$-$C_{10}$ carbocyclic;

each $R^{17}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl and heterocyclyl, where each of the ring systems is optionally substituted by OH, halo, $C_1$-$C_3$ alkyl and $C_1$-$C_3$ alkoxy; and $R^{18}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl, heterocyclyl and NHC(=NH)NH$_2$, where each of the ring systems is optionally substituted by OH, halo, $C_1$-$C_3$ alkyl and $C_1$-$C_3$ alkoxy.

The compounds of the invention typically include a suitable, negatively-charged counter ion. This may be any suitable counter ion and in particular may be any suitable pharmaceutically acceptable counter ion. Examples of suitable counter ions include, but are not limited to: fluoride, chloride, bromide, iodide, nitrate, sulfate, phosphate, hexafluorophosphate, formate, acetate, trifluoroacetate, propionate, butyrate, lactate, citrate, tartrate, malate, maleate, succinate, benzoate, p-chlorobenzoate, diphenylacetate, triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate.

In an embodiment of the invention, there is provided a compound according to the Formula Ia:

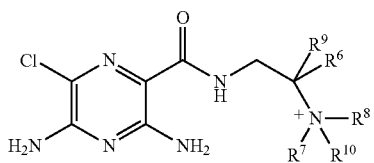

Ia or solvates or hydrates thereof, wherein $R^6$ is —($C_0$-$C_6$ alkylene)-$R^{6a}$, wherein the alkylene linker is optionally substituted by one or more groups selected from $C_1$-$C_3$ alkyl, halo and OH;

$R^{6a}$ is selected from H, a $C_3$-$C_{10}$ carbocyclic group, $NR^{11}R^{12}$, $C(O)NR^{13}R^{14}$, aryl, heteroaryl, heterocyclyl and a group of the formula P—(CH$_2$)$_m$-Q, wherein each of the ring systems is optionally substituted by one or more substituents selected from the List Z;

P is selected from a bond, —O—, —C(O)—, —C(O)O—, —NHC(=N)NH— and —S(O$_2$)—, —S(O$_2$)NR$^a$—, —NR$^a$C(O)—, —NR$^a$C(O)O—, —NR$^a$S(O$_2$)— and —NR$^a$C(O)NR$^b$—;

R$^a$ and R$^b$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

Q is selected from H, $C_1$-$C_6$ alkyl, a $C_3$-$C_{10}$ carbocyclic group, aryl, heteroaryl and heterocyclyl, wherein the carbocyclic, aryl, heteroaryl and heterocyclyl groups are each optionally substituted by one or more substituents selected from List Z;

m is 0, 1, 2 or 3;

$R^7$, $R^8$ and $R^{10}$ are each independently selected from $C_1$-$C_6$ alkyl, $C_2$-$C_6$ alkenyl, $C_2$-$C_6$ alkynyl, a $C_3$-$C_{10}$ carbocyclic group, —($C_1$-$C_3$ alkylene)-$C_3$-$C_{10}$ carbocyclic group, aryl, heteroaryl, heterocyclyl or a group of the formula (CH$_2$)$_d$-A-(CH$_2$)$_b$—B, wherein the carbocyclic, aryl, heteroaryl and heterocyclyl groups are each optionally substituted by one or more substituents selected from List Z; and wherein the alkyl and alkylene groups are optionally substituted by one or more halogen atoms, OH groups or phenyl groups; or $R^7$ and $R^8$, together with the nitrogen atom to which they are attached form a 4- to 10-membered nitrogen-containing heterocyclic group which is optionally substituted by one or more substituents selected from the List Z; or $R^6$ and $R^8$, together with the atoms to which they are attached form a 4- to 10-membered nitrogen-containing heterocyclic group which is optionally substituted by one or more substituents selected from the List Z;

A is selected from a bond, —O—, —C(O)—, —C(O)NR$^c$—, —C(O)O—, —OC(O)—, —NHC(=N)NH—, —S(O$_2$)—, —S(O$_2$)NR$^c$—, —NR$^c$C(O)—, —NR$^c$C(O)O—, —OC(O)NR$^c$—, —NR$^c$S(O$_2$)—, —C(O)NR$^c$S(O$_2$)—, —NR$^c$C(O)NR$^d$—, —NR$^c$—, -aryl-, —$C_3$-$C_{10}$ carbocyclyl-, -heteroaryl-, -heterocyclyl-, -aryl-O—, —O-aryl-, —O—$C_3$-$C_{10}$ carbocyclyl- and —$C_3$-$C_{10}$ carbocyclyl-O—, wherein the aryl, carbocyclyl, heteroaryl and heterocyclyl groups are each optionally substituted by one or more substituents selected from List Z;

B is selected from H, $C_1$-$C_6$ alkyl, a $C_3$-$C_{10}$ carbocyclic group, NR$^x$R$^y$, C(O)OR$^z$, aryl, heteroaryl and heterocyclyl, wherein the carbocyclic, aryl, heteroaryl and heterocyclyl groups are each optionally substituted by one or more substituents selected from List Z;

d is 1, 2, 3, 4, 5, 6 or 7;

b is 0, 1, 2 or 3;

R$^c$, R$^d$, R$^x$ and R$^y$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

R$^z$ is H or $C_1$-$C_6$ alkyl;

$R^9$ is H or $C_1$-$C_6$ alkyl; or $R^6$ and $R^9$, together with the carbon atom to which they are attached, form a $C_3$-$C_{10}$ carbocyclic group or a 4- to 10-membered heterocyclyl group, wherein each of the ring systems is optionally substituted by one or more substituents selected from the List Z;

$R^{11}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{12}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —C(O)$C_1$-$C_6$ alkyl, —C(O)$C_3$-$C_{10}$ carbocyclic, —C(O)($C_1$-$C_3$ alkylene)-$C_3$-$C_{10}$ carbocyclic, —C(O)(CH$_2$)$_x$ aryl, —C(O)(CH$_2$)$_x$ heteroaryl, —C(O)(CH$_2$)$_x$ heterocyclyl, —C(O)Oalkyl, C(O)Oaryl, (CH$_2$)$_x$ aryl, (CH$_2$)$_x$ heteroaryl and —(CH$_2$)$_x$ heterocyclyl, wherein each of the ring systems is optionally substituted by one or more substituents selected from the List Z;

$R^{13}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{14}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —(CH$_2$)$_z$ aryl, (CH$_2$)$_z$ heteroaryl and (CH$_2$)$_z$ heterocyclyl, wherein each of the ring systems is optionally substituted by one or more substituents selected from the List Z;

x is 0, 1, 2 or 3;

z is 0, 1, 2 or 3;

each Z is independently selected from OH, aryl, heteroaryl, heterocyclyl, benzyl, $C_1$-$C_6$ alkyl optionally substituted by one or more halogen atoms, CN or OH groups, $C_1$-$C_6$ alkoxy optionally substituted by one or more halogen atoms, CN or OH groups, -Oaryl, -Obenzyl, —O(CH$_2$)$_a$C(O)E, NR$^{15}$(SO$_2$)R$^{17}$, (SO$_2$)NR$^{15}$R$^{16}$, (SO$_2$)R$^{18}$, NR$^{15}$C(O)R$^{17}$, C(O)NR$^{15}$R$^{17}$, NR$^{15}$C(O)NR$^{16}$R$^{17}$, NR$^{15}$C(O)OR$^{17}$, NR$^{15}$R$^{17}$, C(O)OR$^{15}$, OC(O)R$^{15}$, OC(O)NR$^{15}$, C(O)R$^{17}$, SR$^{15}$, CN, NO$_2$, and halogen; and when there are two or more Z substitutents, two Z substituents together with the atoms to which they are attached optionally form a 5- to 7-membered carbocyclic or a 4- to 7-membered heterocyclic substituent fused to the ring system;
a is 0, 1, 2, 3 or 4, where the alkylene group is optionally substituted by OH or $NH_2$ when a is 1, 2, 3 or 4;
E is $NR^{15}R^{17}$ or $OR^{17}$;
each $R^{15}$ and $R^{16}$ is independently selected from H, $C_1$-$C_6$ alkyl, a $C_3$-$C_{10}$ carbocyclic group and —($C_1$-$C_3$ alkylene)-$C_3$-$C_{10}$ carbocyclic;
each $R^{17}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl and heterocyclyl, where each of the ring systems is optionally substituted by OH, halo, $C_1$-$C_3$ alkyl and $C_1$-$C_3$ alkoxy; and $R^{18}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl, heterocyclyl and $NHC(=NH)NH_2$, where each of the ring systems is optionally substituted by OH, halo, $C_1$-$C_3$ alkyl and $C_1$-$C_3$ alkoxy.

In a still further embodiment of the invention as defined anywhere above, $R^9$ is H. Suitably, $R^9$ is H and $R^6$ is selected from H and $C_1$-$C_6$ alkyl. Optionally, $R^9$ and $R^6$ are both H.

In a yet further embodiment of the invention as defined anywhere above, there is provided a compound according to Formula I selected from:

| Structure |
| --- |
| 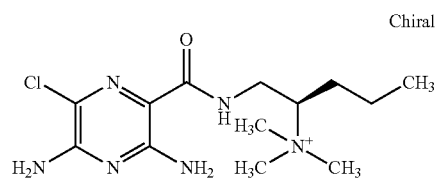 |
| 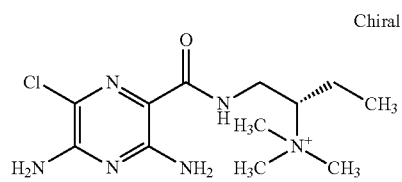 |
| 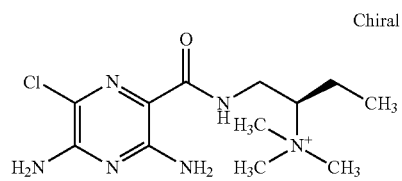 |
| 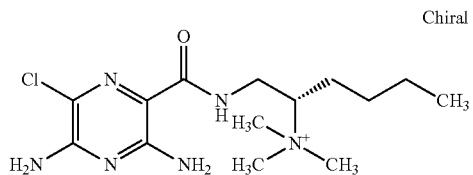 |
| 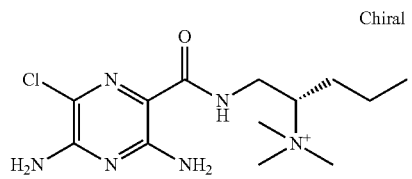 |
| 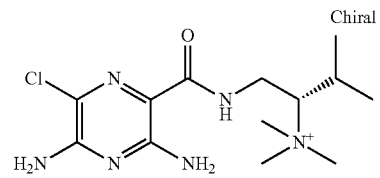 |

-continued
| Structure |
|---|
| 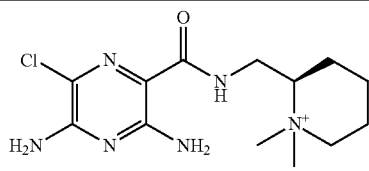 |
| Chiral |
| 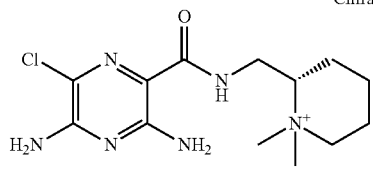 |
| 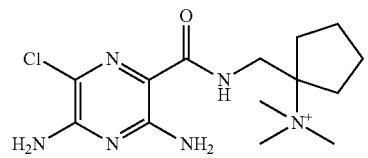 |
| Chiral |
| 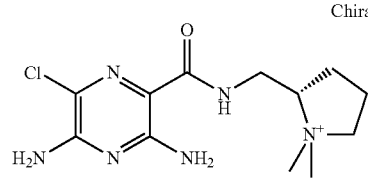 |
| Chiral |
| 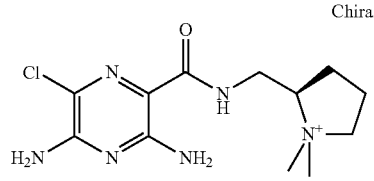 |
| Chiral |
| 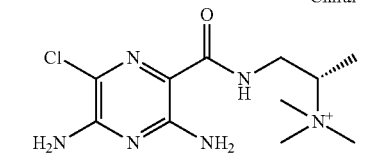 |
| 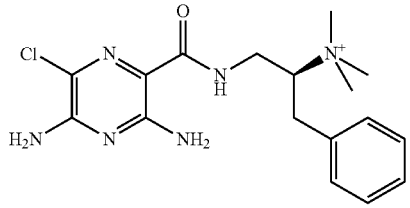 |
| Chiral |
| 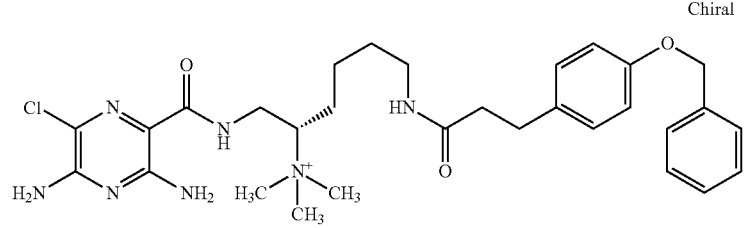 |

| Structure |
|---|
| 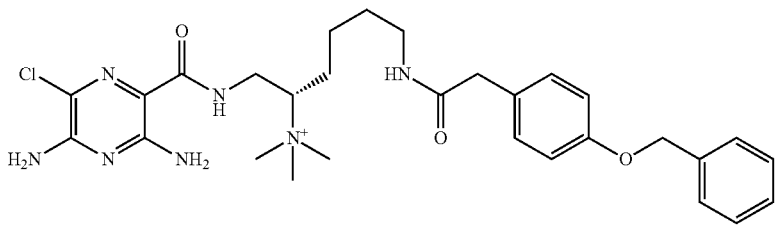 |
| 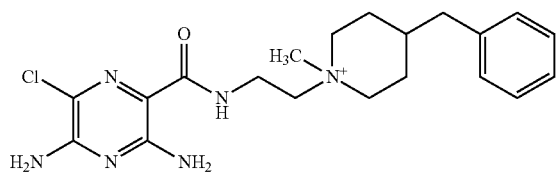 |
| 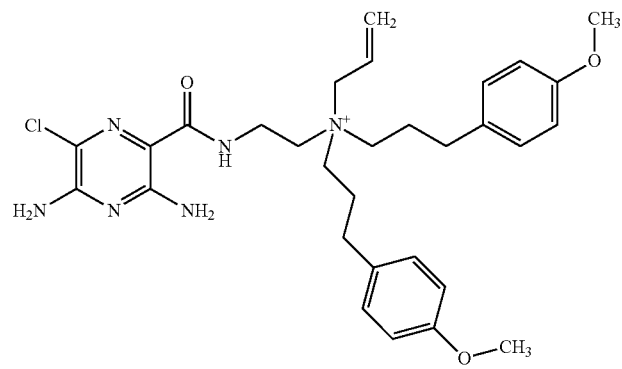 |
| 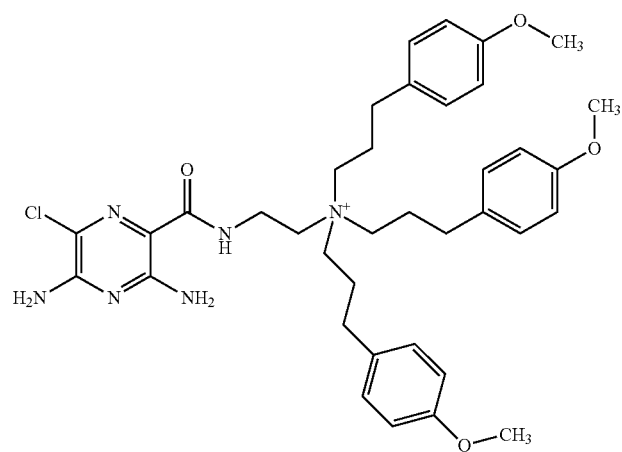 |

| Structure |
|---|
| 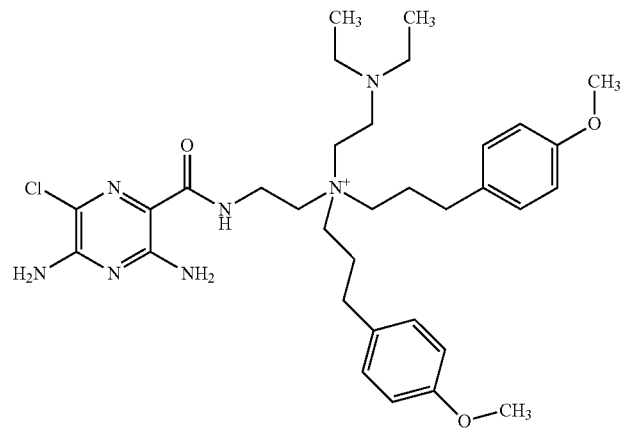 |
| 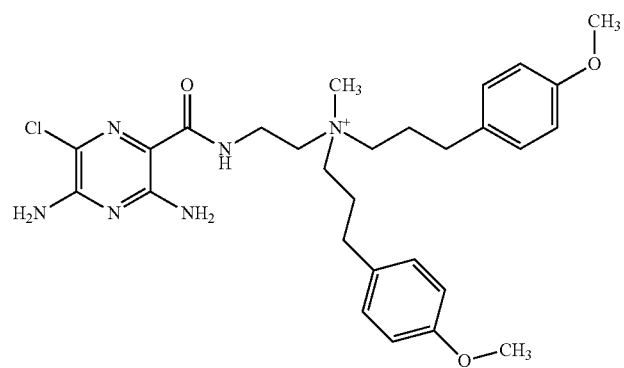 |
| 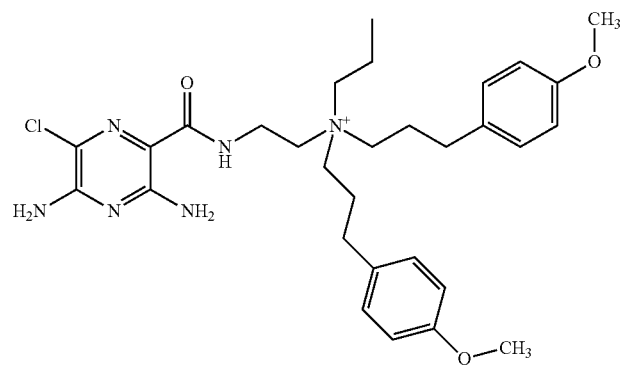 |
| 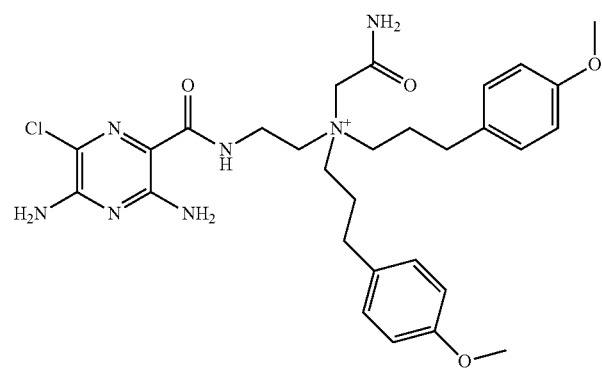 |

| Structure |
|---|
| 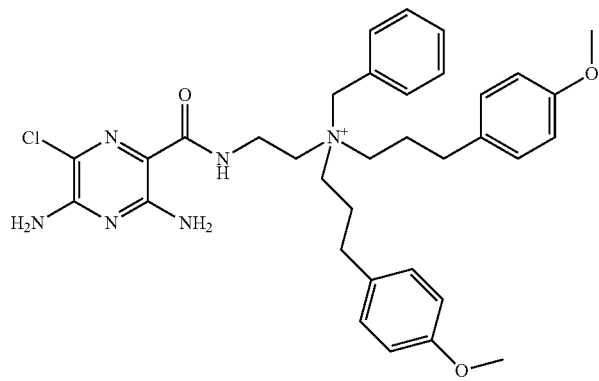 |
| 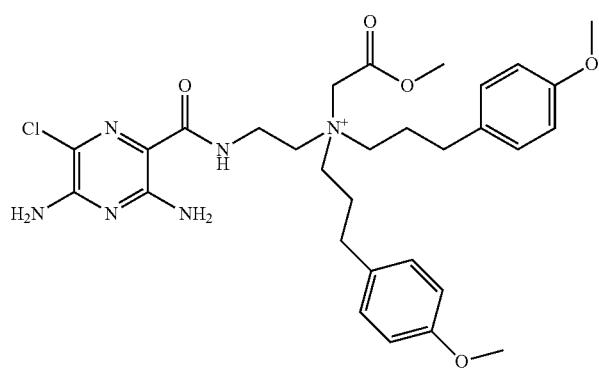 |
| 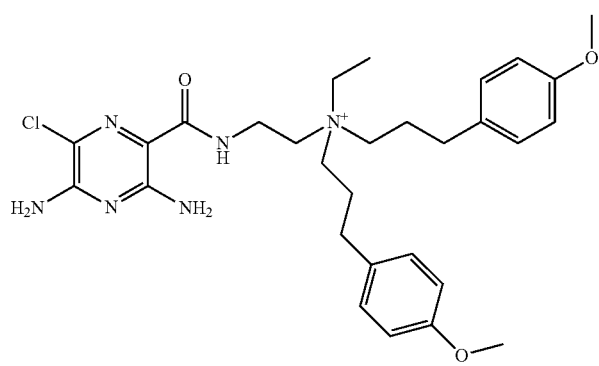 |
| 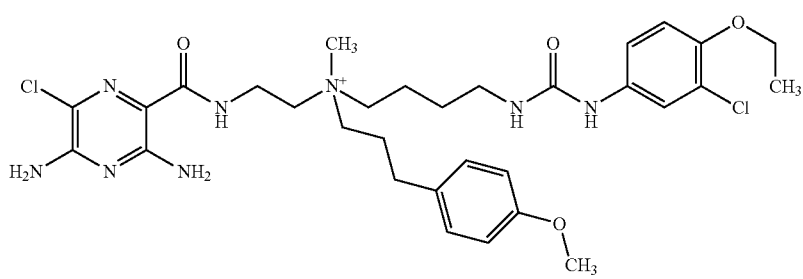 |
| 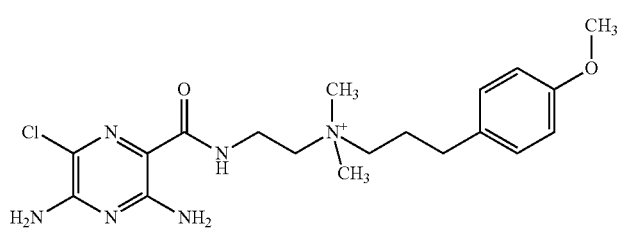 |

| Structure |
|---|
| 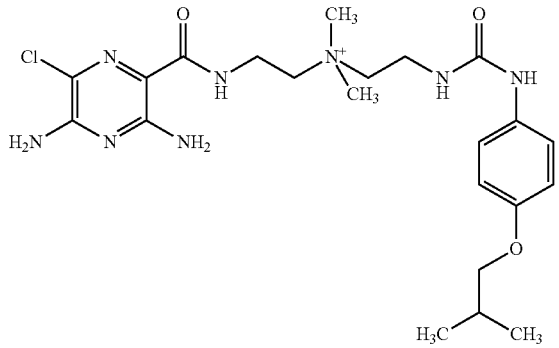 |
| 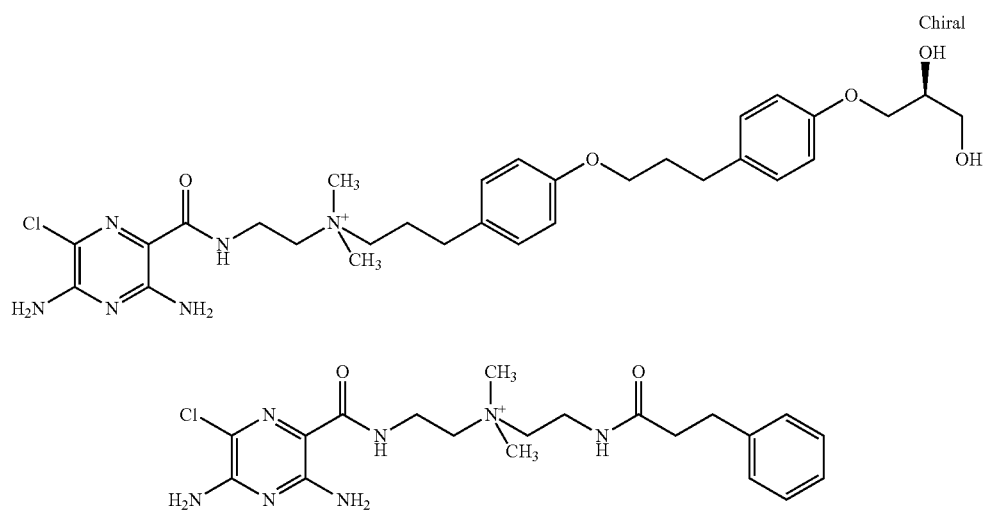 |
| 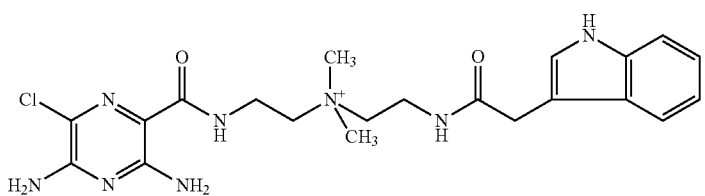 |
| 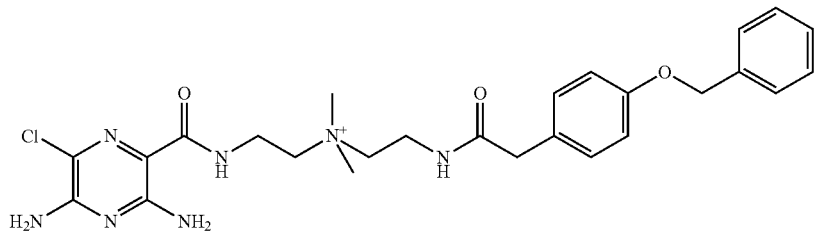 |
| 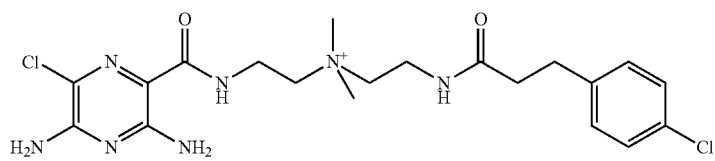 |

-continued
| Structure |
|---|
| 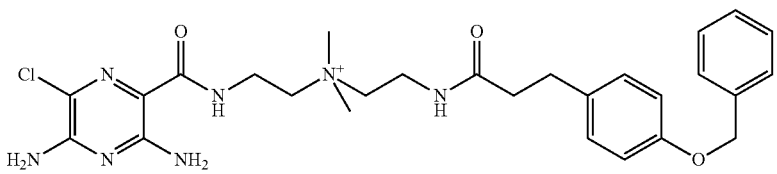 |
| 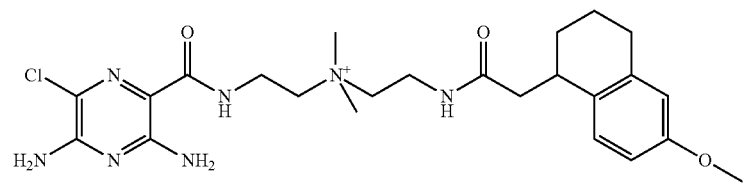 |
| 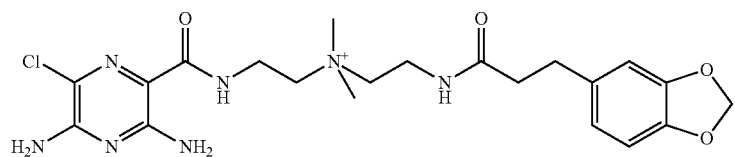 |
| 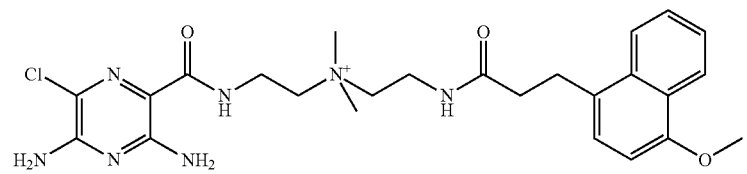 |
| 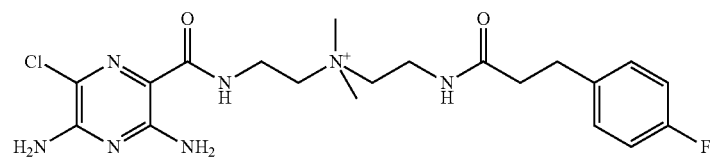 |
| 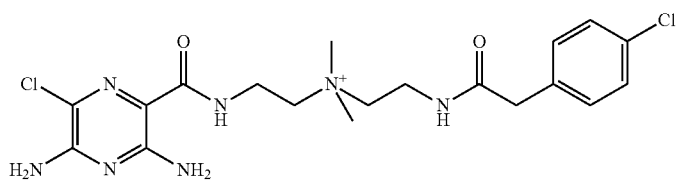 |
| 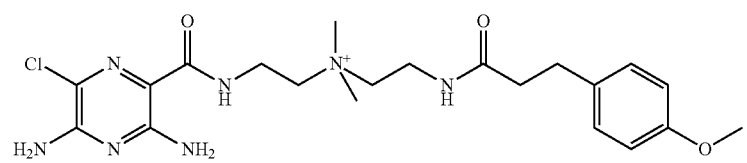 |
| 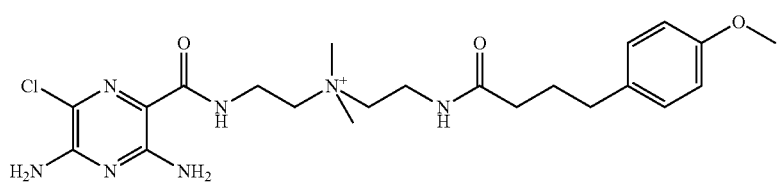 |
| 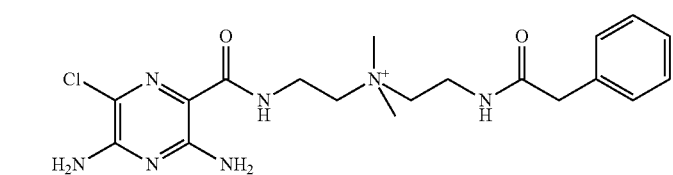 |

| Structure |
| --- |
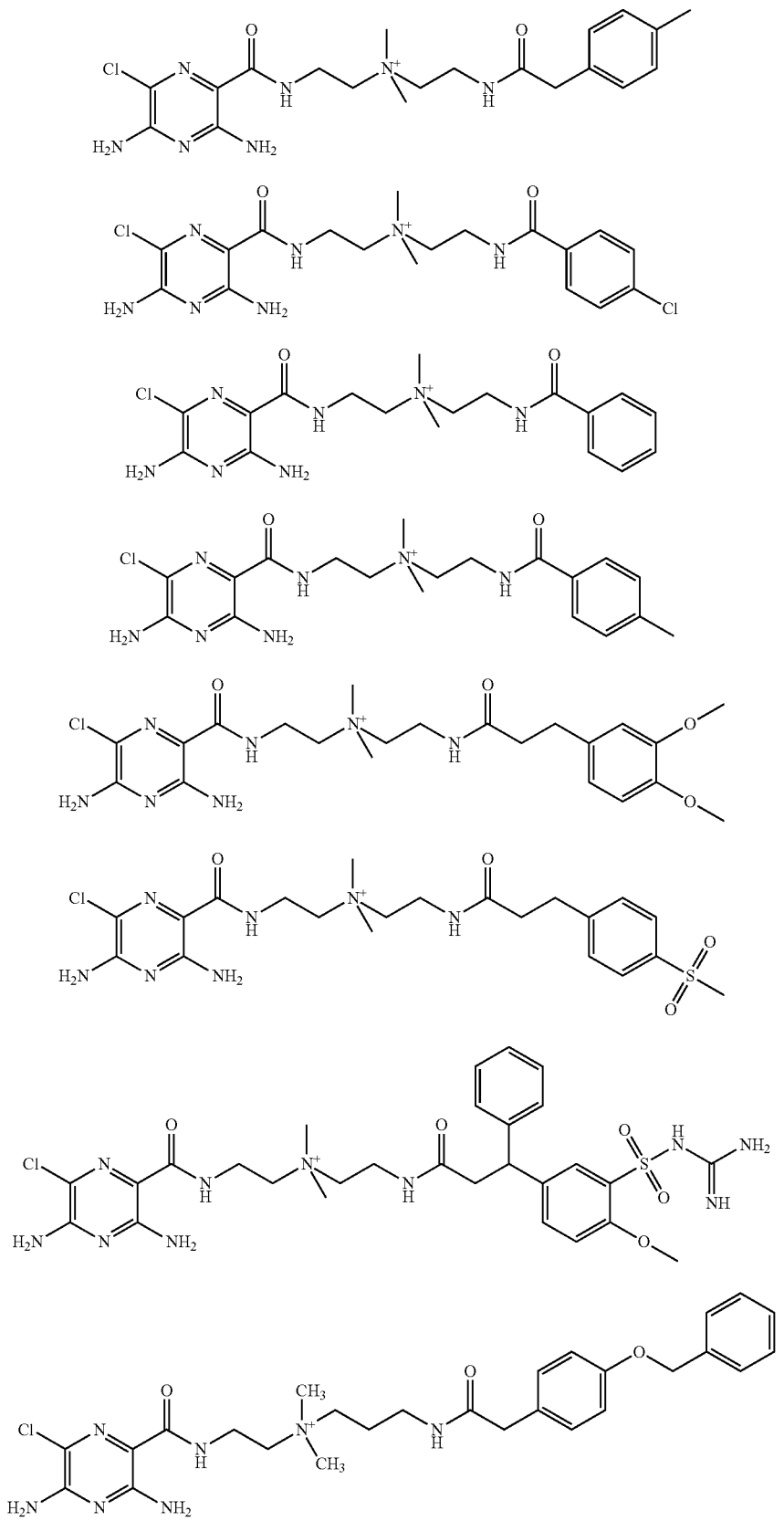

-continued
Structure
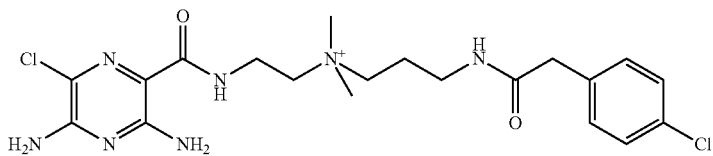
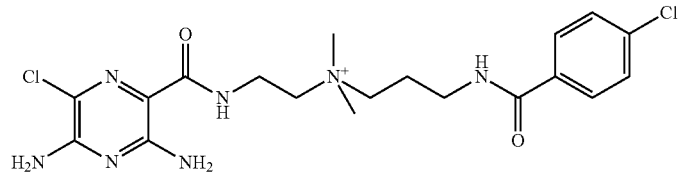
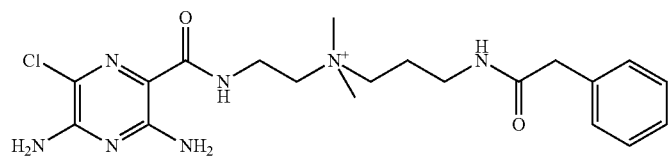
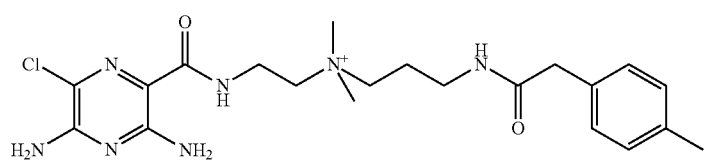
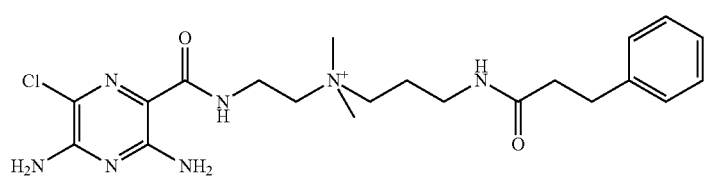
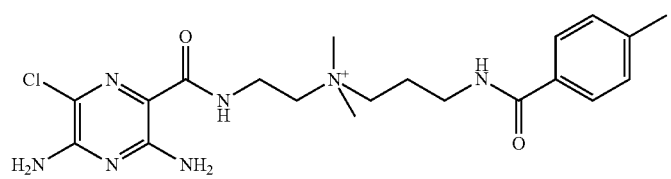
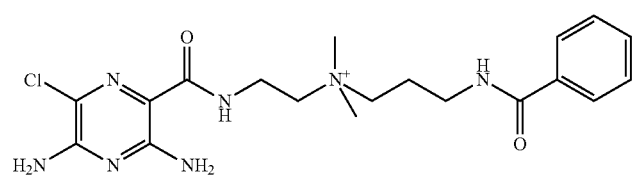
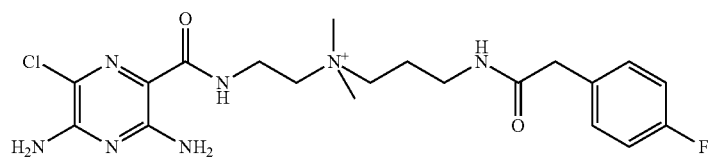
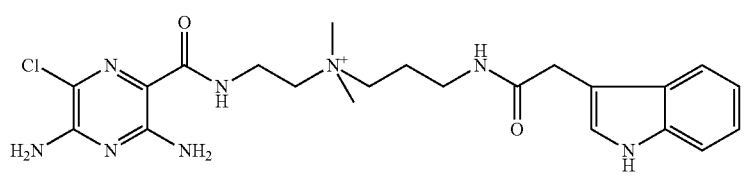

| Structure |
| --- |
| 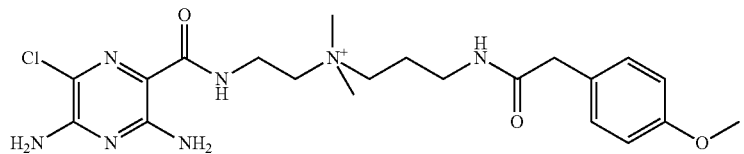 |
| 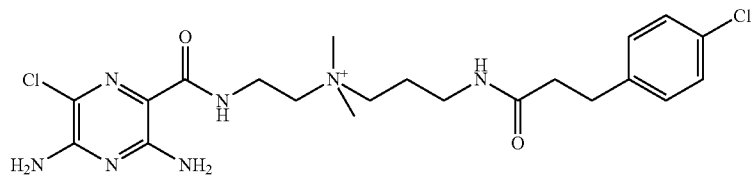 |
| 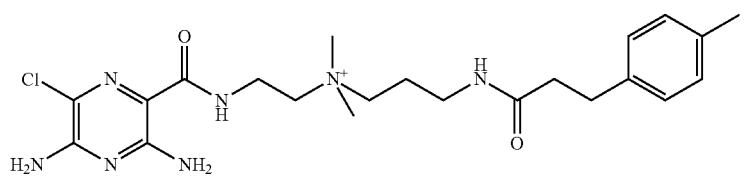 |
| 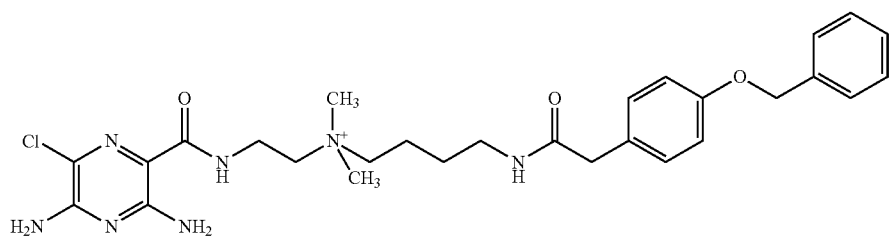 |
| 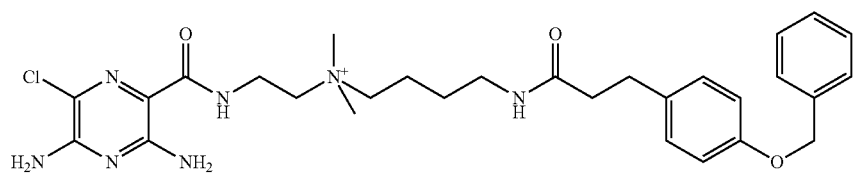 |
| 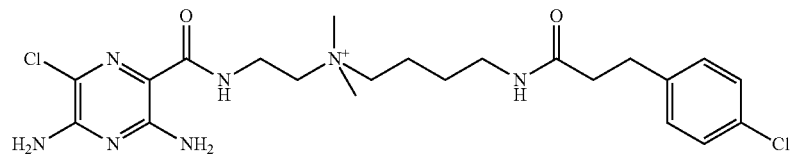 |
| 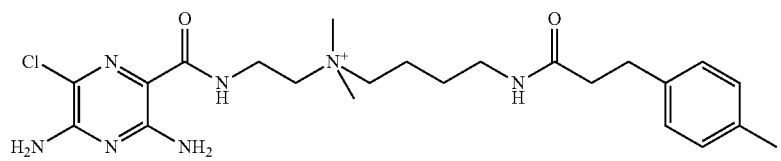 |
| 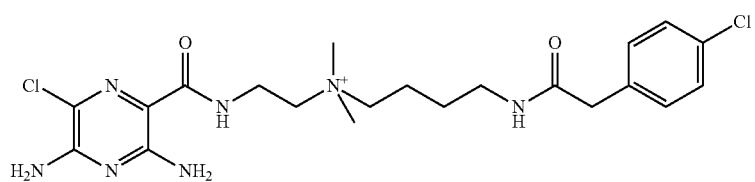 |

| Structure |
| --- |
| 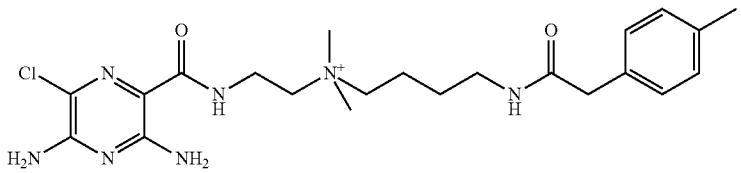 |
| 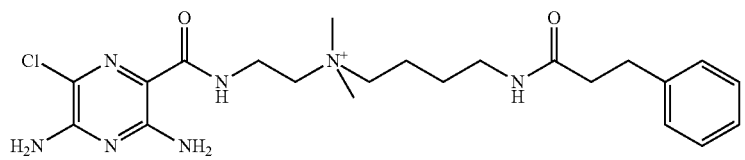 |
| 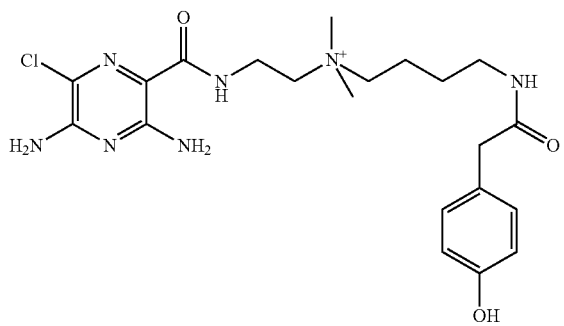 |
| 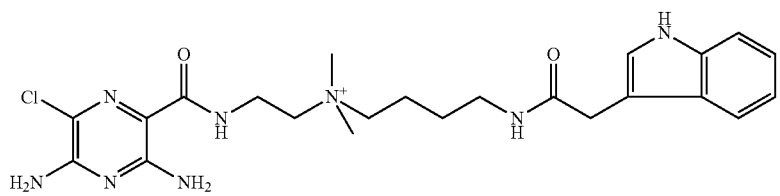 |
| 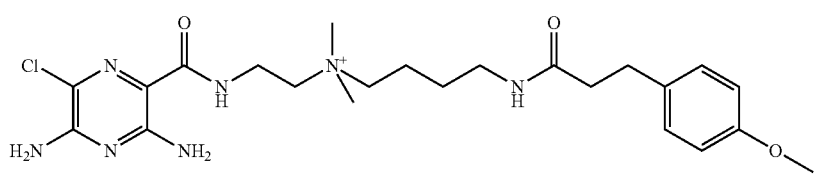 |
| 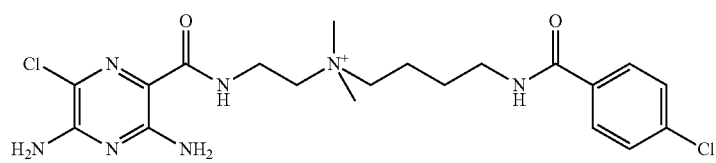 |
| 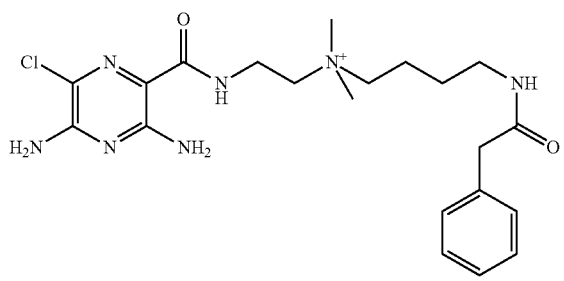 |

| Structure |
|---|
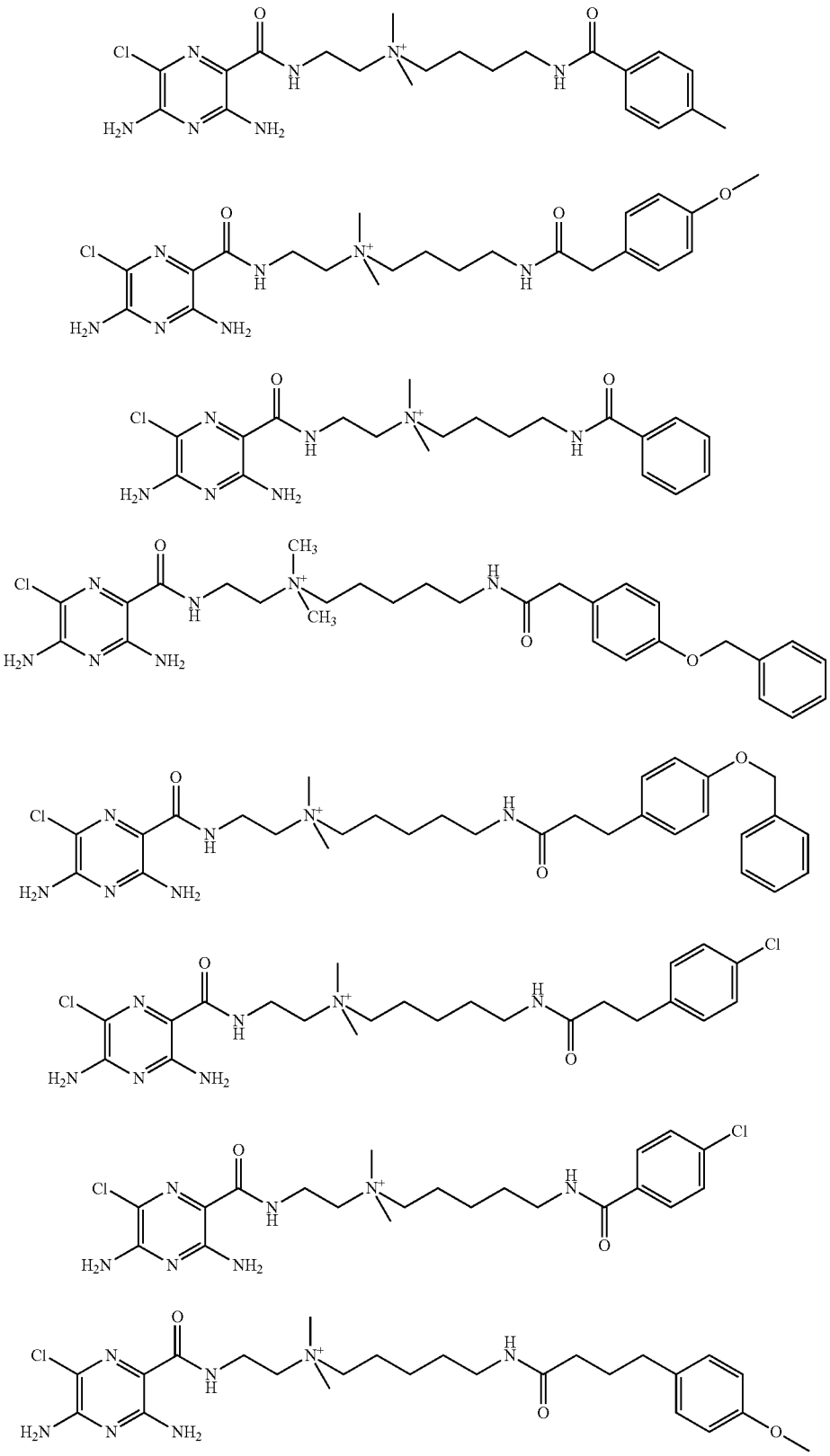

| Structure |
|---|
| 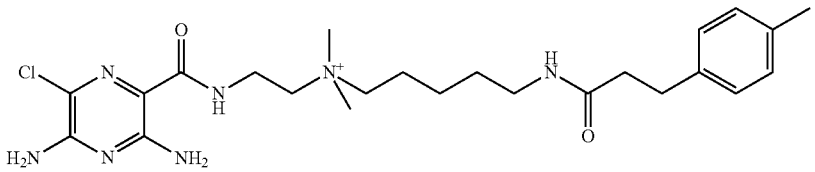 |
| 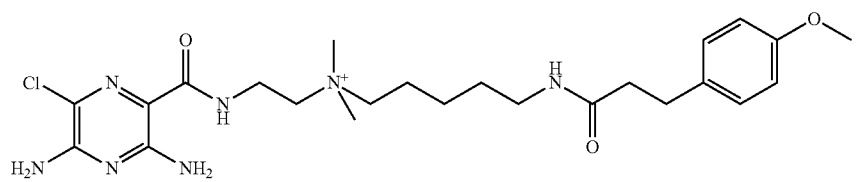 |
| 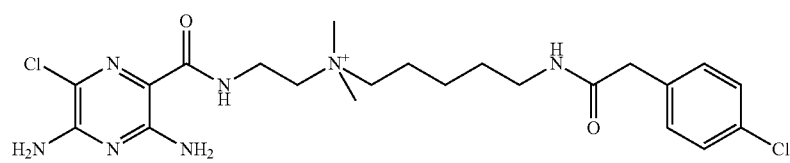 |
| 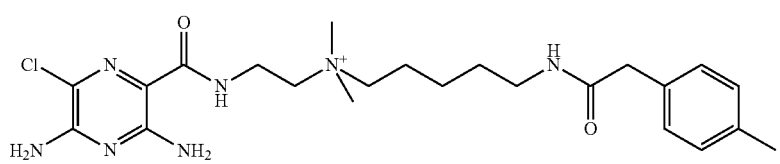 |
| 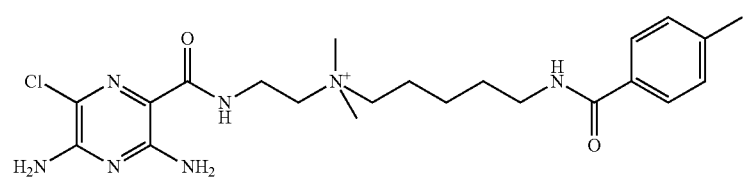 |
| 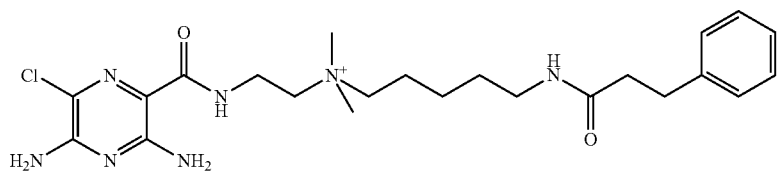 |
| 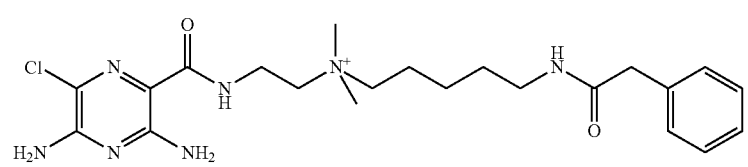 |
| 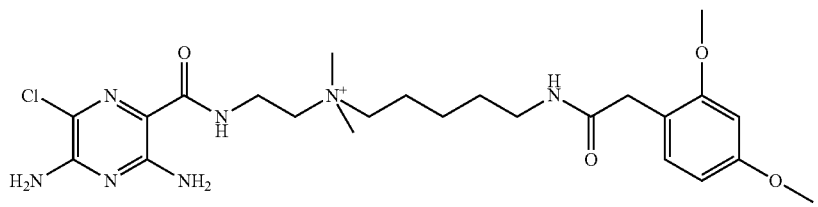 |

-continued
| Structure |
|---|
| 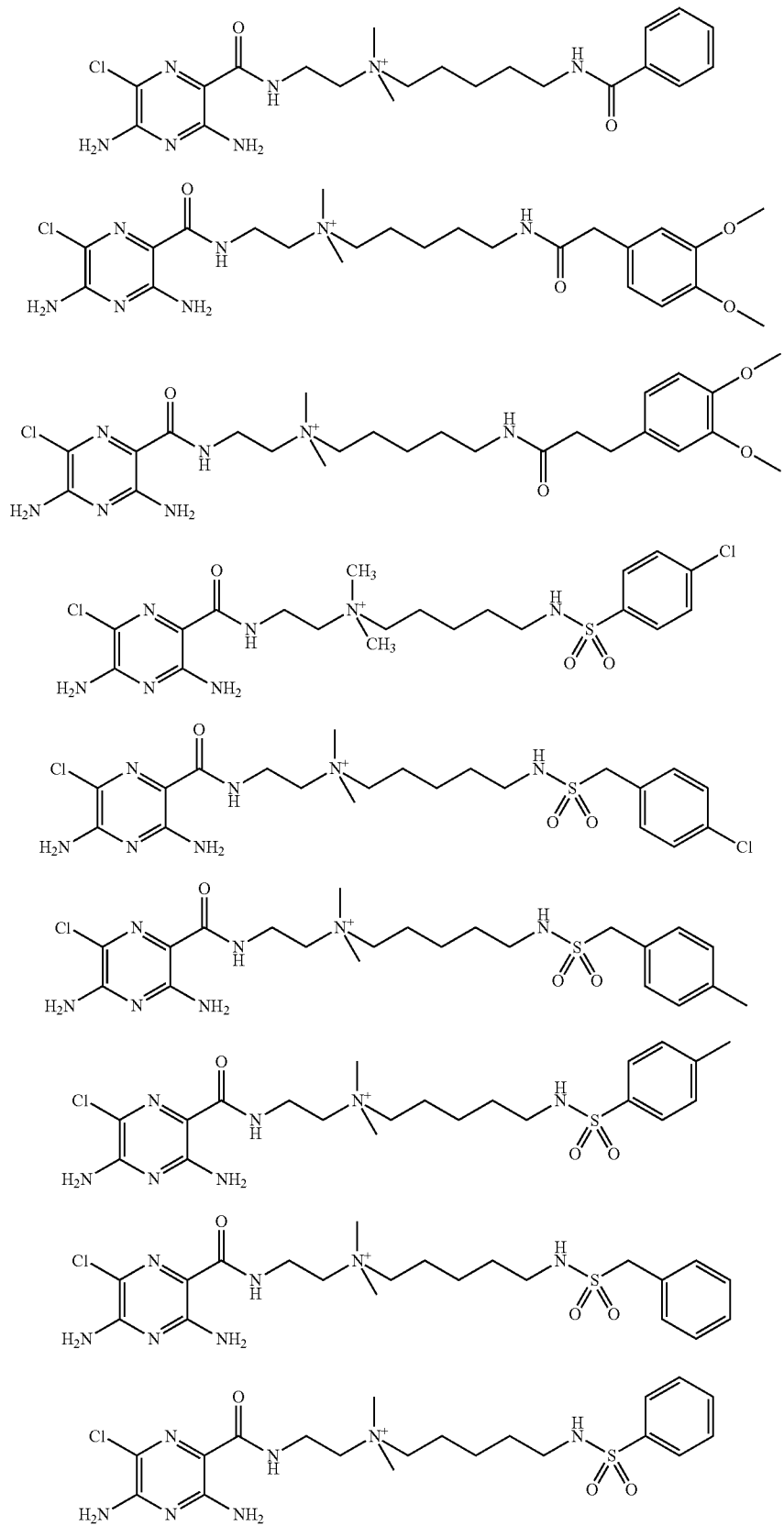 |

| Structure |
|---|
| 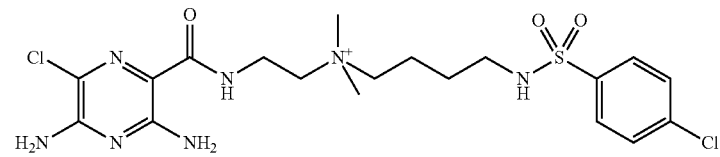 |
| 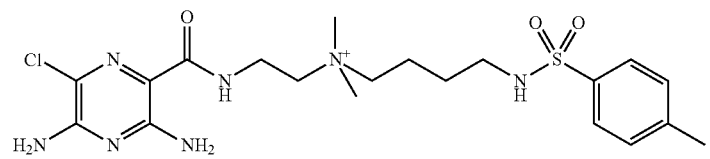 |
| 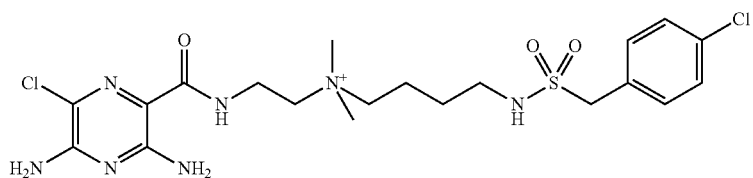 |
| 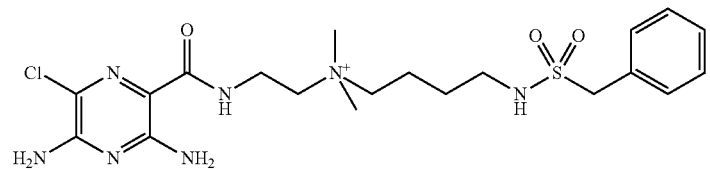 |
| 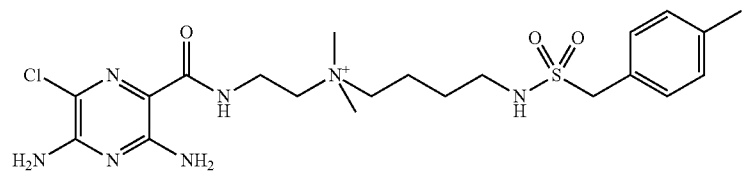 |
| 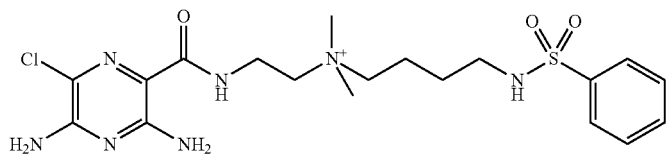 |
| 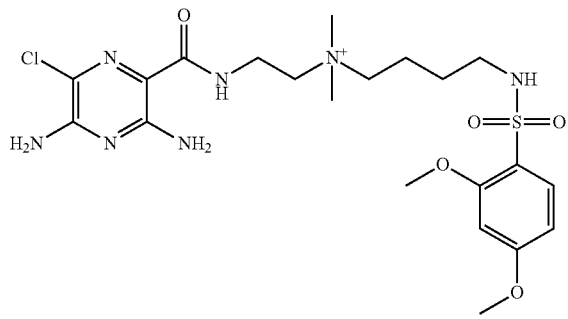 |

| Structure |
|---|
| 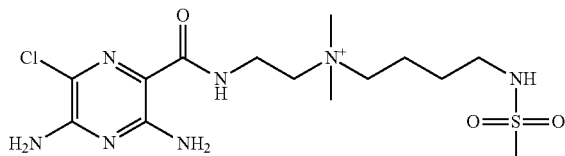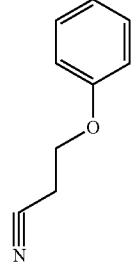 |
| 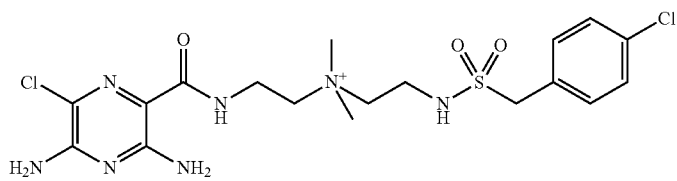 |
| 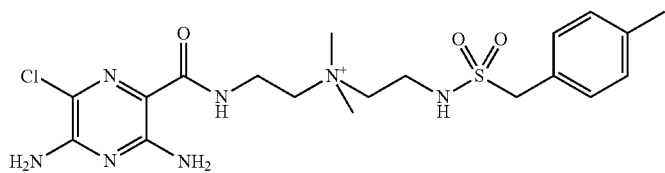 |
| 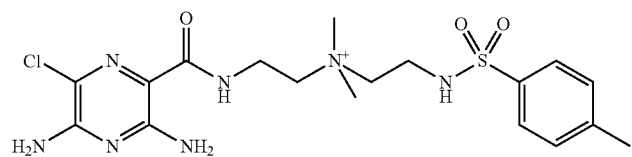 |
| 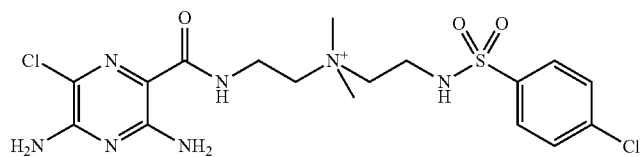 |
| 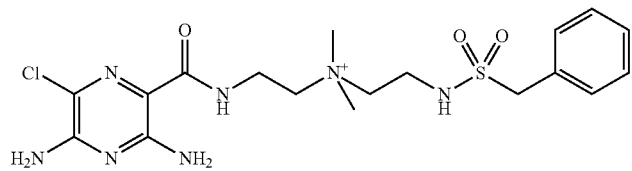 |
| 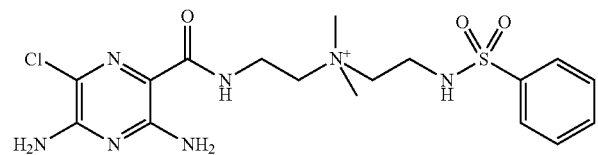 |

-continued
| Structure |
|---|
| 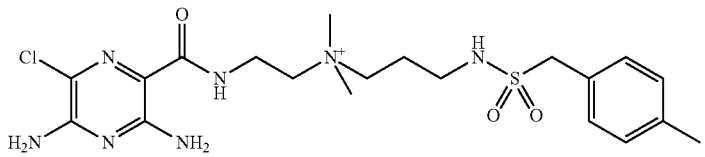 |
| 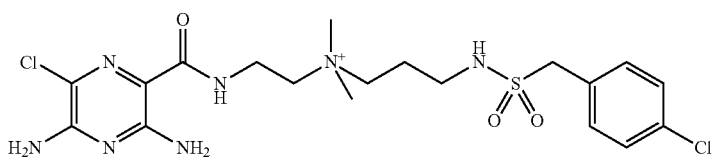 |
| 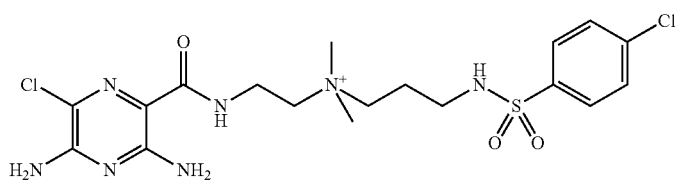 |
| 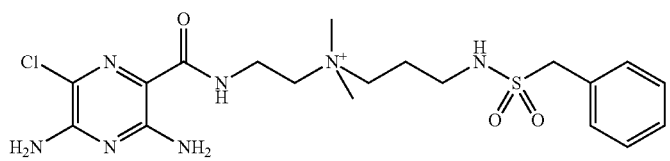 |
| 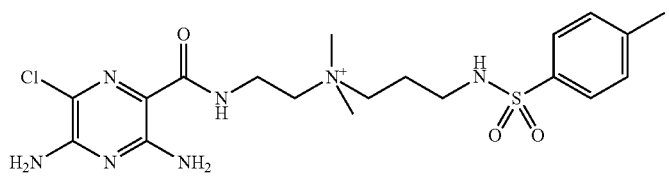 |
| 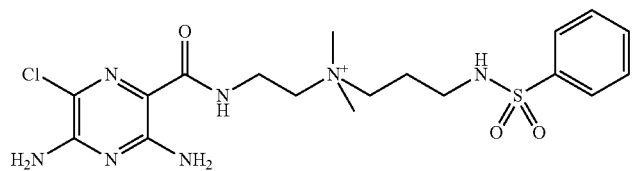 |
| 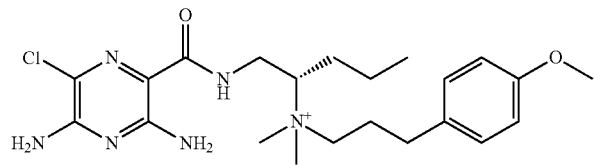 |
| 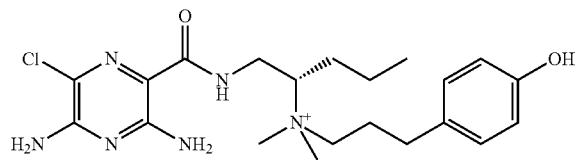 |

| Structure |
|---|
| 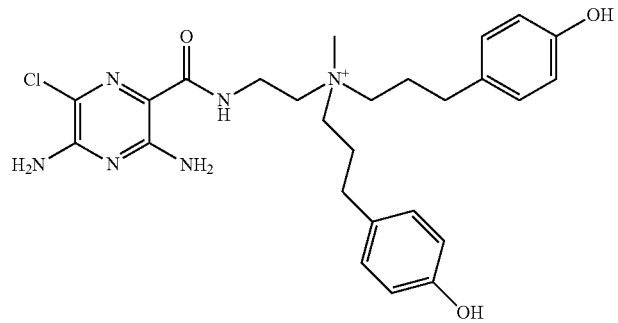 |
| 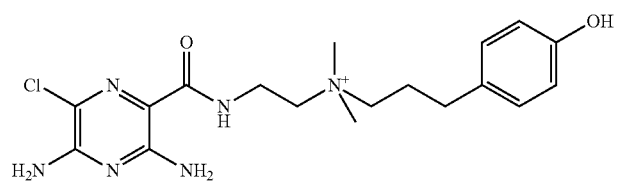 |
| 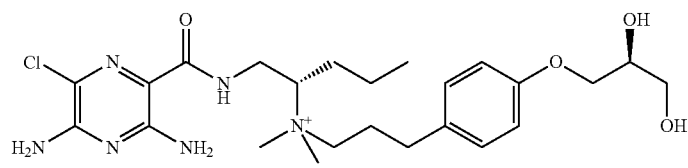 |
| 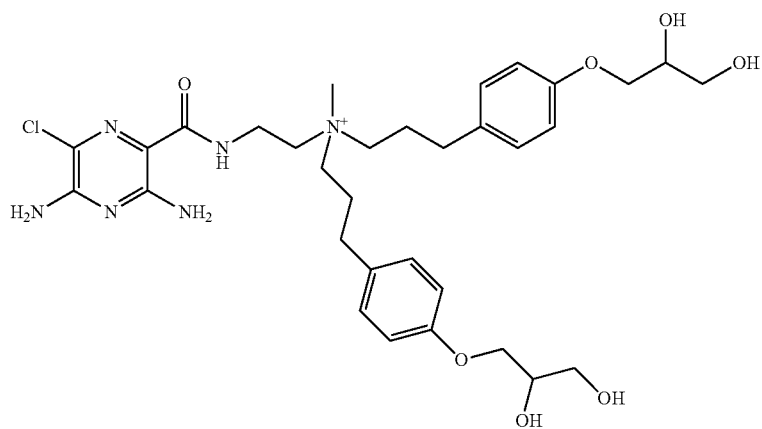 |
| 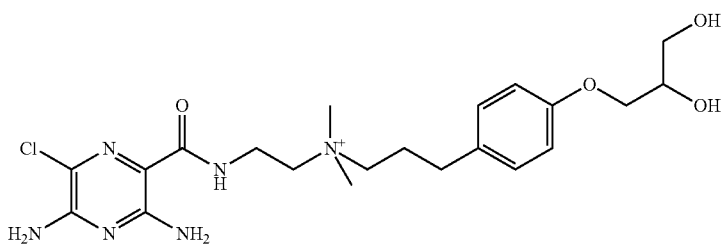 |
| 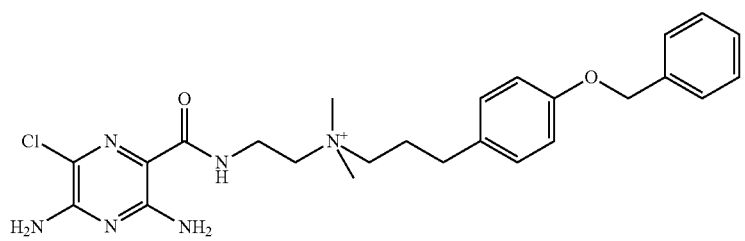 |

-continued
| Structure |
| --- |
| 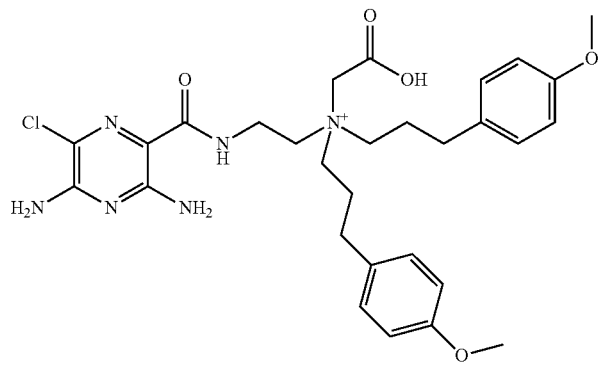 |
| 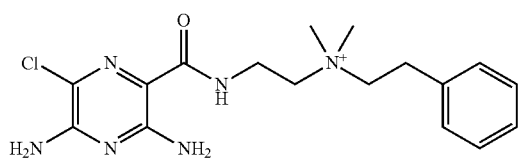 |
| 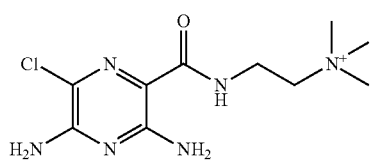 |
| 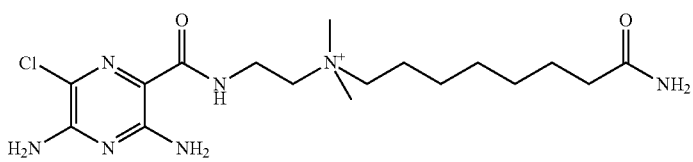 |
| 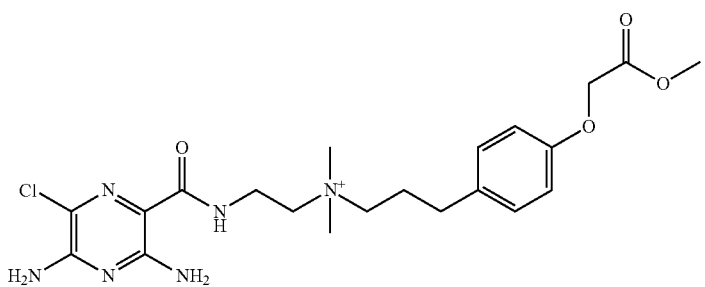 |
| 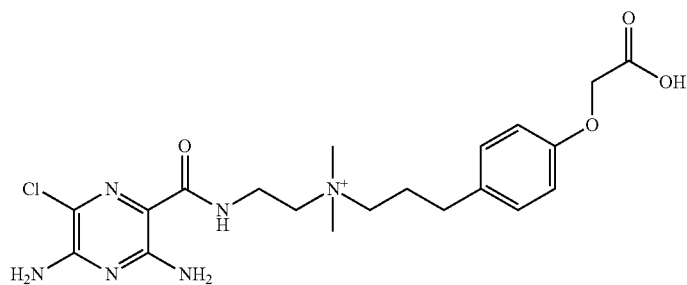 |

DEFINITIONS

Terms used in the specification have the following meanings:

"Optionally substituted" means the group referred to can be substituted at one or more positions by any one or any combination of the radicals listed thereafter.

"optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_6$ alkyl", as used herein, denotes straight chain or branched alkyl group having 1-6 carbon atoms. If a different number of carbon atoms is specified, such as $C_4$ or $C_3$, then the definition is to be amended accordingly.

"$C_2$-$C_6$ alkenyl", as used herein, denotes straight chain or branched alkenyl group having 2-6 carbon atoms and one or more carbon-carbon double bonds. If a different number of carbon atoms is specified, such as $C_4$ or $C_3$, then the definition is to be amended accordingly.

"$C_2$-$C_6$ alkynyl", as used herein, denotes straight chain or branched alkynyl group having 2-6 carbon atoms and one or more carbon-carbon triple bonds. If a different number of carbon atoms is specified, such as $C_4$ or $C_3$, then the definition is to be amended accordingly.

"$C_1$-$C_6$-alkoxy", as used herein, denotes straight chain or branched alkoxy having 1-6 carbon atoms. If a different number of carbon atoms is specified, such as $C_4$ or $C_3$, then the definition is to be amended accordingly.

The term "alkylene" denotes a straight chain or branched saturated hydrocarbon linking group containing the relevant number of carbon atoms.

The terms "—($C_1$-$C_6$ alkylene)-" or "—($C_1$-$C_4$ alkylene)-" denote a hydrocarbon linking group having the relevant number of carbon atoms. If a different number of carbon atoms is specified, such as $C_4$ or $C_3$, then the definition is to be amended accordingly.

"a $C_3$-$C_{10}$ carbocyclic group", "$C_3$-$C_{10}$ carbocyclic" or "$C_3$-$C_{10}$ carbocyclyl", as used herein, denotes a non-aromatic carbocyclic group having 3- to 10-ring carbon atoms that is saturated or partially unsaturated. This term includes both $C_3$-$C_{10}$ cycloalkyl and $C_5$-$C_{10}$ cycloalkenyl groups, as well as bicyclic and spirocyclic groups. Where the group is bicyclic, it may comprise an aromatic or non-aromatic monocyclic ring fused to a non-aromatic monocyclic ring. Optionally, the ring system contains 3-6 carbon atoms, i.e. a $C_3$-$C_6$ carbocyclic group. Examples of $C_3$-$C_{10}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and bicyclodecyl. If a different number of carbon atoms is specified, such as $C_6$, then the definition is to be amended accordingly.

"$C_3$-$C_{10}$ cycloalkyl", as used herein denotes a saturated carbocyclic ring system having 3- to 10-ring carbon atoms. Optionally, the ring system contains 5 or 6 carbon atoms, i.e. $C_5$-$C_6$ cycloalkyl.

"$C_5$-$C_{10}$ cycloalkenyl", as used herein, denotes a non-aromatic carbocyclic group having 5- to 10-ring carbon atoms that contains one or more carbon-carbon double bonds. Optionally, the ring system contains 5 or 6 carbon atoms, i.e. $C_5$-$C_6$ cycloalkenyl.

The terms "aryl" and "$C_6$-$C_{15}$-Aromatic carbocyclic group", as used herein, denote an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_{10}$ (e.g. a $C_6$-$C_{10}$ aryl group), then the definition is to be amended accordingly. In certain embodiments, aryl is phenyl or naphthylenyl. In further embodiments, aryl is phenyl.

The terms "heterocyclic group" and "4- to 10-Membered heterocyclic group" refer to 4- to 10-membered heterocyclic rings containing at least one ring heteroatom selected from the group consisting of nitrogen, oxygen and sulphur, which may be saturated or partially saturated. The group includes benzofused heterocyclic ring systems. Examples of such heterocyclic groups include, but are not limited to, pyrrolidine, piperidine, piperazine, pyrrolidinone, morpholine, tetrahyrofuran, tetrahydrothiophene, tetrahydrothiopyran, tetrahydropyran, 1,4-dioxane and 1,4-oxathiane. Suitably, the heterocyclic group may be a 5- to 6-membered group.

The terms "heteroaryl group" and "heteroaromatic group" denote a 5- to 10-membered aromatic heterocyclic ring containing at least one ring heteroatom selected from the group consisting of nitrogen, oxygen and sulphur. Examples of such heteroaryl groups include, but are not limited to, pyrrole, pyrazole, imidazole, triazole, tetrazole, pyridine, pyridazine, pyrimidine, pyrazine, triazine, quinoline, isoquinoline, indole, isoindole, indolizine, indazole, benzimidazole, purine, quinolizine, cinnoline, quinazoline, quinoxaline, naphthyridine, phthalazine, pteridine, acridine, phenazine and phenanthroline. Suitably, the heteroaryl group may be a 5- to 6-membered group. It is to be understood that any and all embodiments of the present invention may be taken in conjunction with any other embodiment to describe additional embodiments of the present invention. Furthermore, any elements of an embodiment are intended to be combinable with any and all other elements from any of the embodiments to describe additional embodiments. It is understood by those skilled in the art that combinations of substituents where not possible are not an aspect of the present invention.

A second aspect of the present invention provides for the use of a compound of formula (I) in any of the aforementioned embodiments for the manufacture of a medicament for the treatment of an inflammatory or allergic condition, particularly an inflammatory or obstructive airways disease, or mucosal hydration.

An embodiment of the present invention provides for the use of a compound of formula (I) in any of the aforementioned embodiments for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis sire.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Especially suitable compounds of formula (I) are those described hereinafter in the Examples.

As mentioned above, the skilled person will appreciate that the compounds of Formula (I) will typically include a counter ion. Thus, the compounds of the invention may be considered as follows:

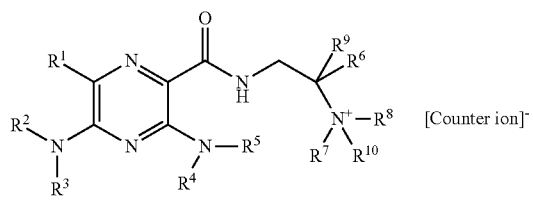

I wherein $R^1$, $R^2$, $R^3$, $R^4$, $R^5$, $R^6$, $R^7$, $R^8$, $R^9$ and $R^{10}$ are as defined above and [Counter ion]⁻ is a suitable counter ion, optionally selected from fluoride, chloride, bromide, iodide, nitrate, sulfate, phosphate, hexafluorophosphate, formate, acetate, trifluoroacetate, propionate, butyrate, lactate, citrate, tartrate, malate, maleate, succinate, benzoate, p-chlorobenzoate, diphenylacetate, triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate.

The skilled person will also appreciate that the counter ion may exist in different stoichiometries. Thus, the two ionic components of the compound may not exist in a 1:1 ratio. For example, certain counter ions may exist in a "2⁻" form such that the ratio of the cationic component to counter ion may be 2:1. Other stoichiometries are, of course, possible and all such combinations are considered to be within the scope of the invention.

Pharmaceutically acceptable solvates in accordance with the invention include those wherein the solvent of crystallisation may be isotopically substituted e.g. $D_2O$, $d_6$-acetone or $d_6$-DMSO.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2H$ and $^3H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with heavier isotopes such as deuterium ($^2H$) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Some of the compounds of Formula I may exist in different tautomeric forms. Tautomerism is well known to those skilled in the art and the skilled person will readily appreciate which groups are able to tautomerise to form the different tautomeric forms. The invention includes all tautomeric forms of the compounds of Formula I.

Synthesis

Generally, compounds according to Formula I can be synthesized by the routes described in Scheme 1 and the Examples.

For instance, intermediate 1 can be reacted with intermediate 2 in the presence of a suitable coupling agent and organic base in organic solvent to provide a compound of Formula 3 as the free base. Reaction of this intermediate with a suitable alkylating agent, $R^{10}$—X, wherein X is a suitable leaving group, provides a compound of Formula I. The leaving group X is well known in the art and may be any suitable group that facilitates alkylation. Examples of the leaving group X include chloride, bromide, iodide, mesylate and tosylate groups.

Intermediates can be prepared from methods known by those skilled in the art or are commercially available.

Scheme 1

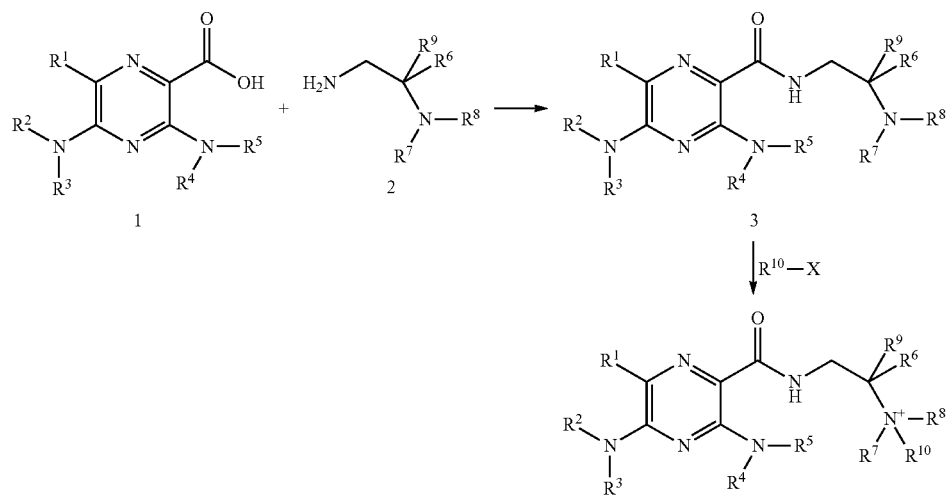

The compounds of Formula (I) can be obtained in the form of hydrates or solvates containing a solvent used for crystallisation. Compounds of formula (I) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of formula (I) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

Pharmacological Activity

Having regard to their blockade of the epithelial sodium channel (ENaC), compounds of formula (I), hereinafter alternately referred to as "agents of the invention", are useful in the treatment of conditions which respond to the blockade of the epithelial sodium channel, particularly conditions benefiting from mucosal hydration.

Diseases treatable by blockade of the epithelial sodium channel, include diseases associated with the regulation of fluid volumes across epithelial membranes. For example, the volume of airway surface liquid is a key regulator of mucociliary clearance and the maintenance of lung health. The blockade of the epithelial sodium channel will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases treatable by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Treatment in accordance with the invention may be symptomatic or prophylactic.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

The suitability of epithelial sodium channel blocker as a treatment of a disease benefiting from mucosal hydration, may be tested by determining the inhibitory effect of the epithelial sodium channel blocker on: the ion channel/ion transport function in suitable isolated cells or confluent epithelia using the methods described in Hirsh et al., *J Pharm Exp Ther* (2004).

Epithelial sodium channel blockers, including the compounds of formula (I), are also useful as co-therapeutic agents for use in combination with other drug substances, such as anti-inflammatory, bronchodilatory, antihistamine or antitussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

The epithelial sodium channel blocker may be mixed with the other drug substance in a fixed pharmaceutical composition or it may be administered separately, before, simultaneously with or after the other drug substance.

Accordingly, the invention includes as a further aspect a combination of epithelial sodium channel blocker with osmotic agents (hypertonic saline, dextran, mannitol, Xylitol)+modifiers of CFTR function, both wild-type and mutant (correctors+potentiators), e.g., those described in WO 2007/021982, WO 2006/099256, WO 2006/127588, WO 2004/080972, WO 2005/026137, WO 2005/035514, WO 2005/075435, WO 2004/111014, WO 2006/101740, WO 2004/110352, WO 2005/120497 and US 2005/0176761, an anti-inflammatory, bronchodilatory, antihistamine, anti-tussive, antibiotic or DNase drug substance, said epithelial sodium channel blocker and said drug substance being in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of epithelial sodium channel blockers with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-aminium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

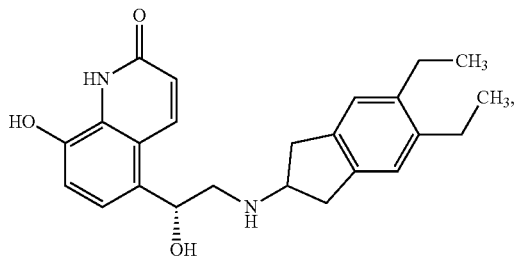

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

In accordance with the foregoing, the invention also provides as a further aspect a method for the treatment of a condition responsive to blockade of the epithelial sodium channel, e.g., diseases associated with the regulation of fluid volumes across epithelial membranes, particularly an obstructive airways disease, which comprises administering to a subject, particularly a human subject, in need thereof a compound of formula (I).

In another aspect the invention provides a compound of formula (I) for use in the manufacture of a medicament for the treatment of a condition responsive to blockade of the epithelial sodium channel, particularly an obstructive airways disease, e.g., cystic fibrosis and COPD.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula (I) optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations. When the composition comprises an aerosol formulation, it preferably contains, e.g., a hydrofluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

Further aspects of the invention include:
(a) a compound of formula (I) in inhalable form, e.g., in an aerosol or other atomisable composition or in inhalable particulate, e.g., micronised form;
(b) an inhalable medicament comprising a compound of formula (I) in inhalable form;
(c) a pharmaceutical product comprising a compound of formula (I) in inhalable form in association with an inhalation device; and
(d) an inhalation device containing a compound of formula I in inhalable form.

Dosages of compounds of formula (I) employed in practising the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of formula (I), hereinafter referred to alternatively as "agents of the invention", are useful as pharmaceuticals. In particular, the compounds have good ENaC blocker activity and may be tested in the following assays.

Cell Culture

Human Bronchial Epithelial cells (HBECs) (Cambrex) were cultured under air-liquid interface conditions to provide a well differentiated mucociliary phenotype.

HBECs were cultured using a modification of the method described by Gray and colleagues (Gray et al., 1996). Cells were seeded in plastic T-162 flasks and were grown in bronchial epithelial cell growth medium (BEGM; Cambrex) supplemented with bovine pituitary extract (52 μg/mL), hydrocortisone (0.5 μg/mL), human recombinant epidermal growth factor (0.5 ng/mL), epinephrine (0.5 μg/mL), transferrin (10 μg/mL), insulin (5 μg/mL), retinoic acid (0.1 μg/mL), triiodothyronine (6.5 μg/mL), gentamycin (50 μg/mL) and amphotericin B (50 ng/mL). Medium was changed every 48 hours until cells were 90% confluent. Cells were then passaged and seeded ($8.25 \times 10^5$ cells/insert) on polycarbonate Snapwell inserts (Costar) in differentiation media containing 50% DMEM in BEGM with the same supplements as above but without triiodothyronine and a final retinoic acid concentration of 50 nM (all-trans retinoic acid). Cells were maintained submerged for the first 7 days in culture, after which time they were exposed to an apical air interface for the remainder of the culture period. At this time, media was changed to DMEM:F12 media containing 2% v/v Ultroser G for the remainder of culture. Amphotericin B was removed from all media 3 feeds prior to use in the Ussing Chambers. Cells were used between days 7 and 21 after establishment of the apical-air interface. At all stages of culture, cells were maintained at 37° C. in 5% $CO_2$ in an air incubator.

Short Circuit Current (ISC) Measurements

Snapwell inserts were mounted in Vertical Diffusion Chambers (Costar) and were bathed with continuously gassed Ringer solution (5% $CO_2$ in $O_2$; pH 7.4) maintained at 37° C. containing (in mM): 120 NaCl, 25 $NaHCO_3$, 3.3 $KH2PO_4$, 0.8 $K_2HPO_4$, 1.2 $CaCl_2$, 1.2 $MgCl_2$, and 10 glucose. The solution osmolarity was between 280 and 300 mOsmol/kg $H_2O$ for all physiological salt solutions used. Cells were voltage clamped to 0 mV (model EVC4000; WPI). RT was measured by applying a 1- or 2-mV pulse at 30-s intervals and calculating RT by Ohm's law. Data were recorded using a PowerLab workstation (ADInstruments).

Test compounds were prepared as a 10 mM stock solution in DMSO (95%). Serial 3-fold dilutions were freshly prepared in an appropriate vehicle (distilled $H_2O$ or Ringers solution). The initial concentration was added to the apical chamber as a 1000× concentrate in 5 μL, resulting in a final 1× concentration the 5 mL volume of the Ussing chamber. Subsequent additions of compound were added in a 3.3 μL volume of the 1000× serially diluted stock solution. At the completion of the concentration-response experiment, amiloride (10 μM) was added into the apical chamber to enable the total amiloride-sensitive current to be measured. An amiloride control $IC_{50}$ was established at the start of each experiment.

Results are expressed as the mean % inhibition of the amiloride-sensitive ISC. Concentration-response curves were plotted and $IC_{50}$ values generated using GraphPad Prism 3.02. Cell inserts were typically run in duplicate and the $IC_{50}$ calculated on the mean % inhibition data.

Compounds of the Examples, herein below, generally have $IC_{50}$ values in the data measurements described above below 10 μM. For example, the compounds detailed below have the $IC_{50}$ values shown.

| Example | $IC_{50}$ (μM) |
|---|---|
| 1 | 0.25 |
| 5 | 0.02 |
| 9 | 3.46 |
| 11 | 5.32 |
| 13 | 0.17 |
| 14 | 0.046 |
| 15 | 0.052 |
| 16 | 0.64 |
| 17 | 0.0075 |
| 18 | 0.037 |
| 19 | 0.020 |
| 20 | 0.002 |
| 21 | 5.69 |
| 22 | 0.051 |
| 23 | 0.034 |
| 26 | 0.012 |
| 27 | 0.22 |
| 29 | 0.025 |
| 30 | 0.14 |
| 33 | 0.15 |
| 35 | 0.41 |
| 38 | 0.81 |
| 50 | 0.24 |
| 51 | 0.42 |
| 53 | 0.60 |
| 63 | 0.043 |
| 65 | 0.15 |
| 78 | 0.062 |
| 94 | 0.25 |
| 100 | 0.29 |
| 108 | 0.54 |
| 120 | 0.004 |
| 121 | 0.01 |
| 122 | 0.13 |
| 124 | 0.025 |
| 125 | 0.24 |
| 126 | 2.27 |
| 129 | 1.14 |
| 130 | 5.81 |
| 132 | 1.49 |
| 133 | 6.52 |

The invention is illustrated by the following Examples.

EXAMPLES

Suitable compounds of the present invention include compounds of formula Ia which as shown in Table 1 below. The method of preparation being described hereinafter.

TABLE 1

| Ex. | Structure | M+ |
|---|---|---|
| 1 | 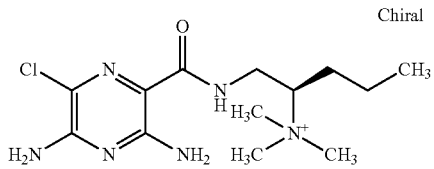 Chiral | 315 |
| 2 | 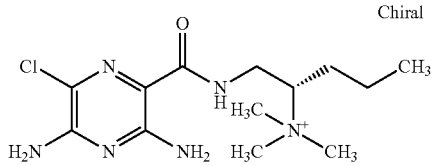 Chiral | 301 |

TABLE 1-continued
| Ex. | Structure | M+ |
|---|---|---|
| 3 | 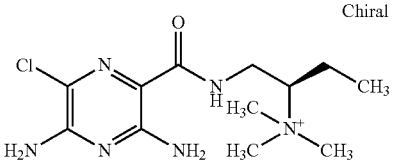 Chiral | 301 |
| 4 | 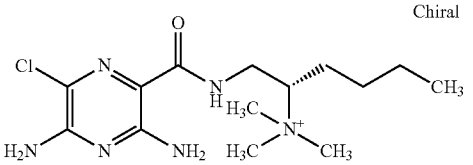 Chiral | 329 |
| 5 | 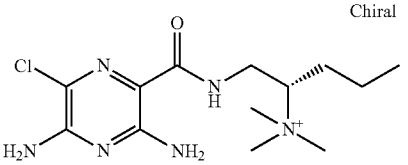 Chiral | 315 |
| 6 | 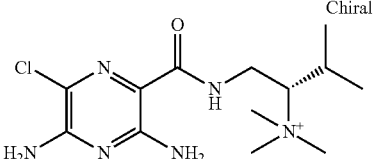 Chiral | 315 |
| 7 | 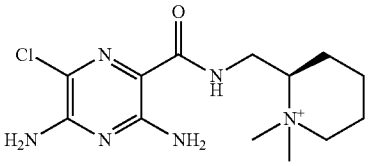 | 313 |
| 8 | 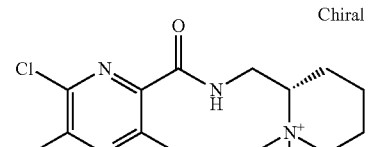 Chiral | 313 |
| 9 | 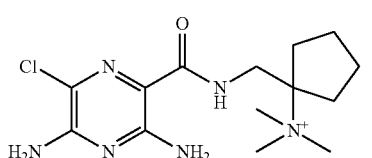 | 327 |
| 10 | 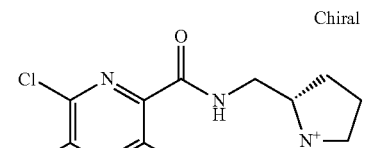 Chiral | 299 |

TABLE 1-continued
| Ex. | Structure | M+ |
|---|---|---|
| 11 | 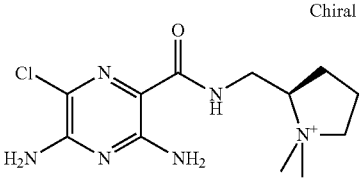 | 299 |
| 12 | 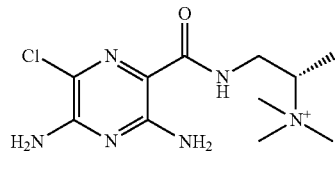 | 287 |
| 13 | 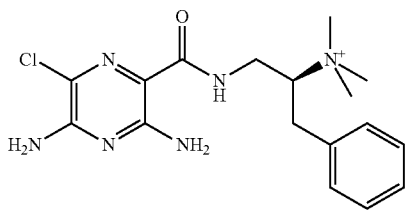 | 363 |
| 14 | 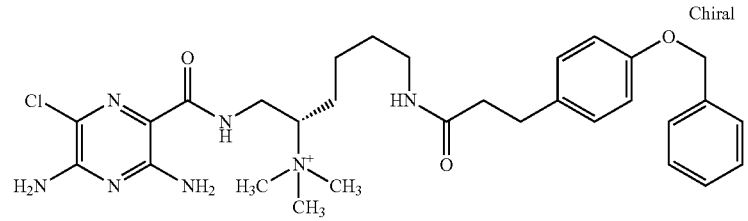 | 582 |
| 15 | 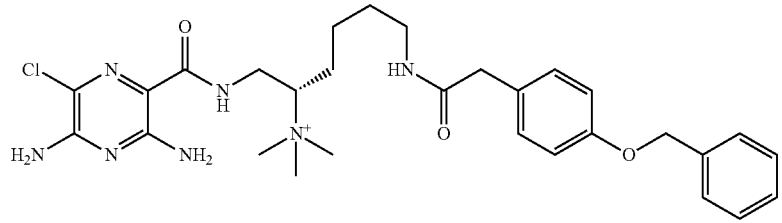 | 568 |
| 16 | 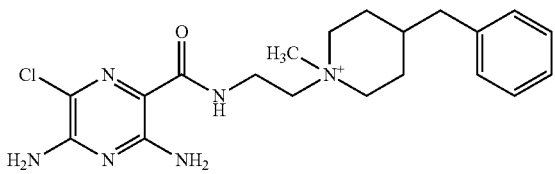 | 403 |

TABLE 1-continued

| Ex. | Structure | M+ |
|---|---|---|
| 17 | 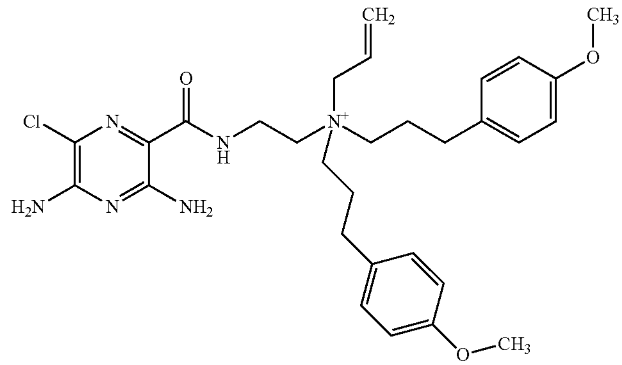 | 567 |
| 18 | 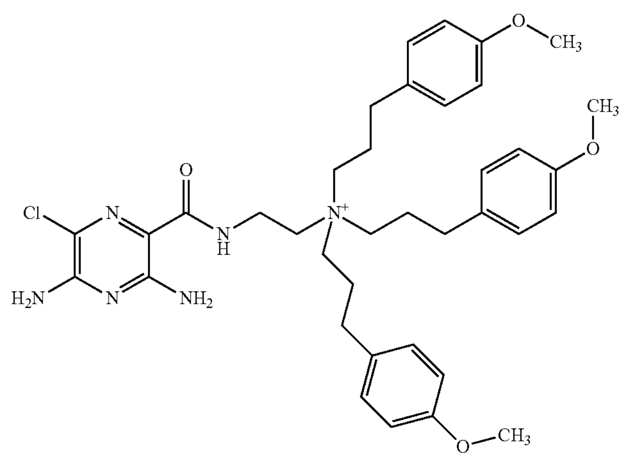 | 675 |
| 19 | 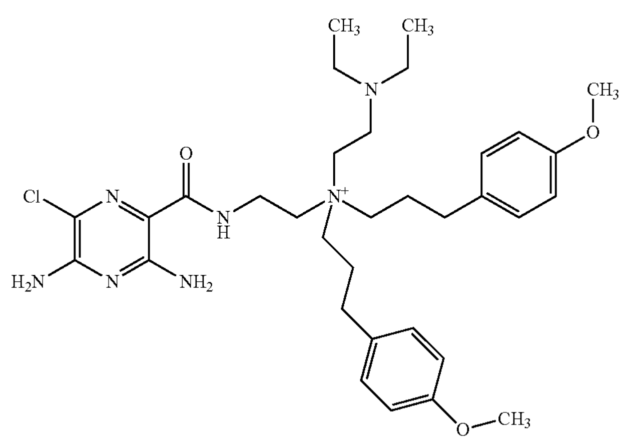 | 626 |
| 20 | 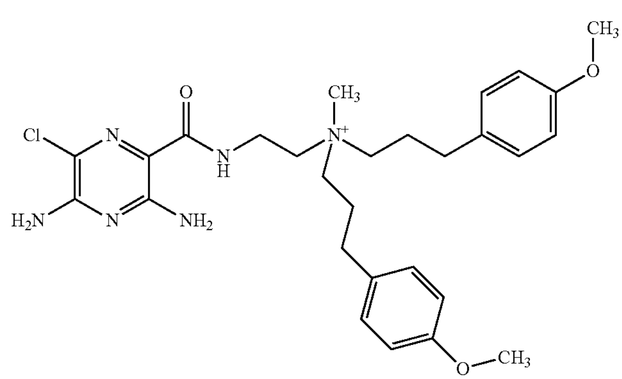 | 541 |

TABLE 1-continued

| Ex. | Structure | M+ |
|---|---|---|
| 21 | 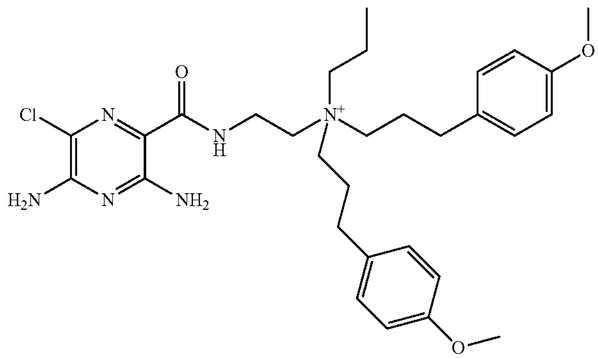 | 0.011 |
| 22 | 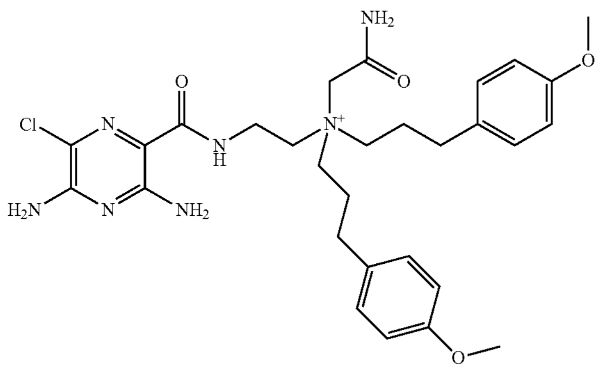 | 584 |
| 23 | 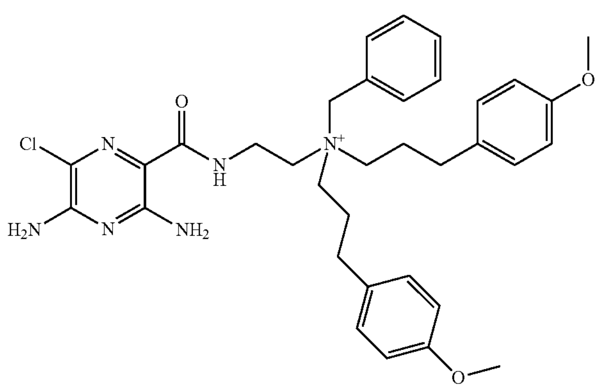 | 617 |
| 24 | 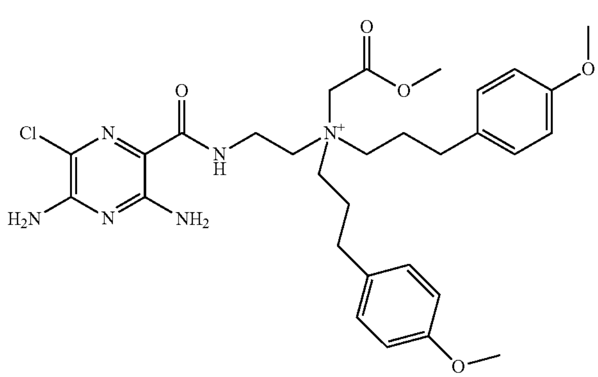 | 599 |

TABLE 1-continued

| Ex. | Structure | M+ |
|---|---|---|
| 25 | 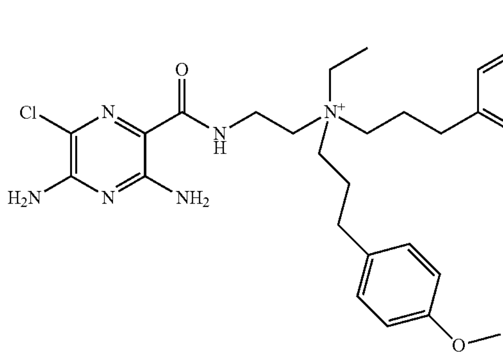 | 555 |
| 26 | 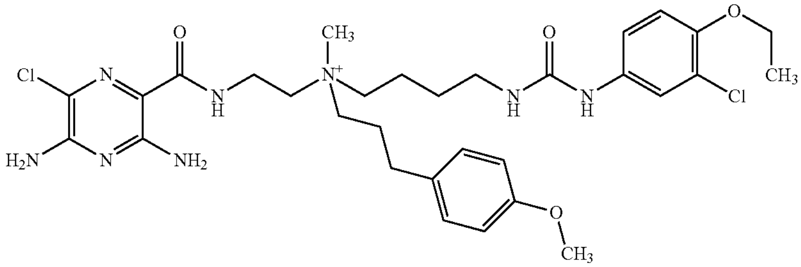 | 661 |
| 27 | 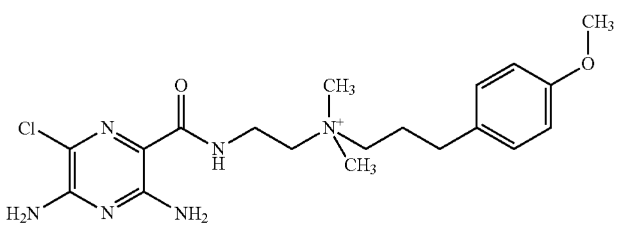 | 407 |
| 28 | 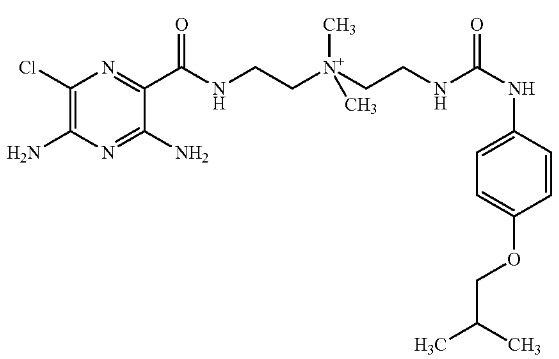 | 493 |
| 29 | 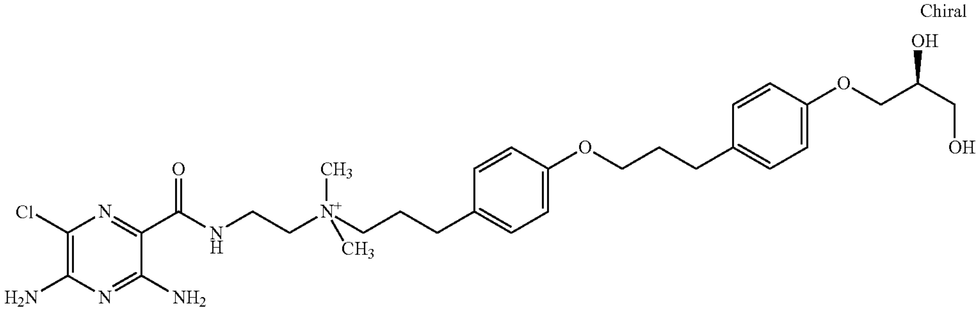 | Chiral 601 |

TABLE 1-continued

| Ex. | Structure | M+ |
|---|---|---|
| 30 | 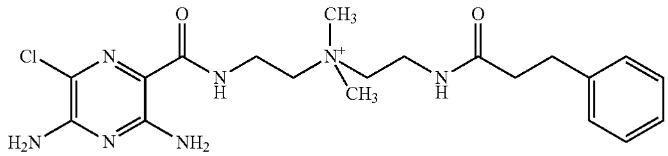 | 434 |
| 31 | 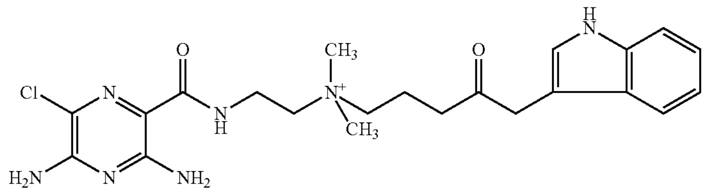 | 459 |
| 32 | 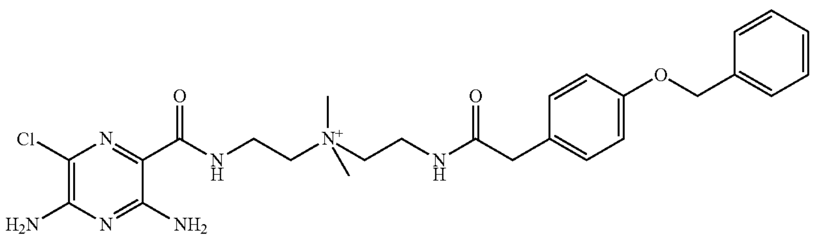 | 526 |
| 33 | 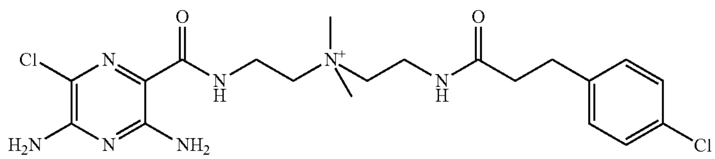 | 468 |
| 34 | 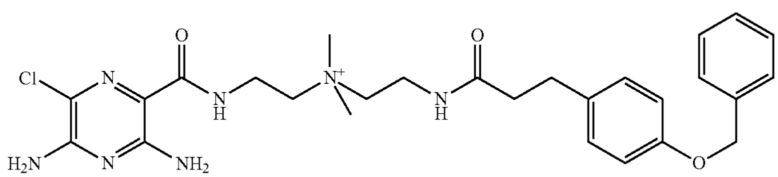 | 540 |
| 35 | 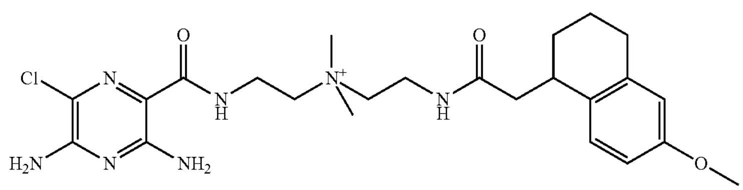 | 504 |
| 36 | 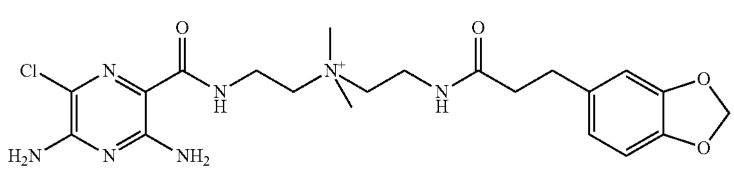 | 478 |
| 37 | 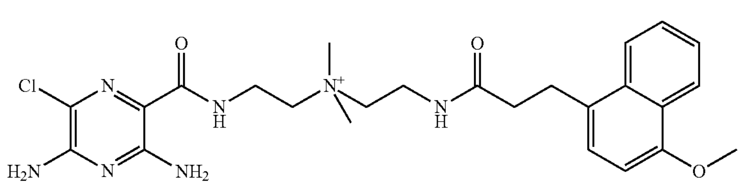 | 514 |

TABLE 1-continued

| Ex. | Structure | M+ |
|---|---|---|
| 38 | pyrazine-C(O)NH-CH2CH2-N+(CH3)2-CH2CH2-NHC(O)CH2CH2-C6H4-F (4-F phenyl) | 452 |
| 39 | pyrazine-C(O)NH-CH2CH2-N+(CH3)2-CH2CH2-NHC(O)CH2-C6H4-Cl (4-Cl phenyl) | 454 |
| 40 | pyrazine-C(O)NH-CH2CH2-N+(CH3)2-CH2CH2-NHC(O)CH2CH2-C6H4-OCH3 (4-OMe phenyl) | 464 |
| 41 | pyrazine-C(O)NH-CH2CH2-N+(CH3)2-CH2CH2-NHC(O)CH2CH2CH2-C6H4-OCH3 (4-OMe phenyl) | 478 |
| 42 | pyrazine-C(O)NH-CH2CH2-N+(CH3)2-CH2CH2-NHC(O)CH2-C6H5 | 420 |
| 43 | pyrazine-C(O)NH-CH2CH2-N+(CH3)2-CH2CH2-NHC(O)CH2-C6H4-CH3 (4-Me phenyl) | 434 |
| 44 | pyrazine-C(O)NH-CH2CH2-N+(CH3)2-CH2CH2-NHC(O)-C6H4-Cl (4-Cl phenyl) | 440 |
| 45 | pyrazine-C(O)NH-CH2CH2-N+(CH3)2-CH2CH2-NHC(O)-C6H5 | 406 |
| 46 | pyrazine-C(O)NH-CH2CH2-N+(CH3)2-CH2CH2-NHC(O)-C6H4-CH3 (4-Me phenyl) | 420 |

(Pyrazine group in all entries: 3,5-diamino-6-chloropyrazine-2-carboxamide)

TABLE 1-continued

| Ex. | Structure | M+ |
|---|---|---|
| 47 | 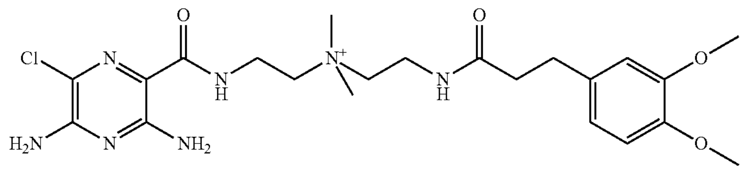 | 494 |
| 48 | 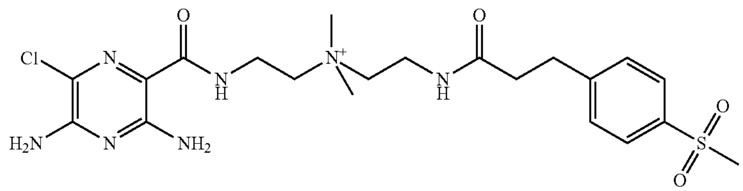 | 512 |
| 49 | 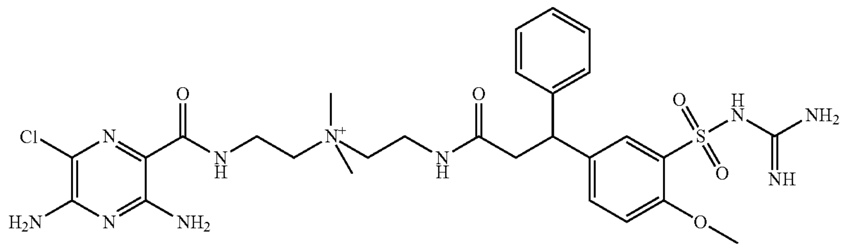 | 661 |
| 50 | 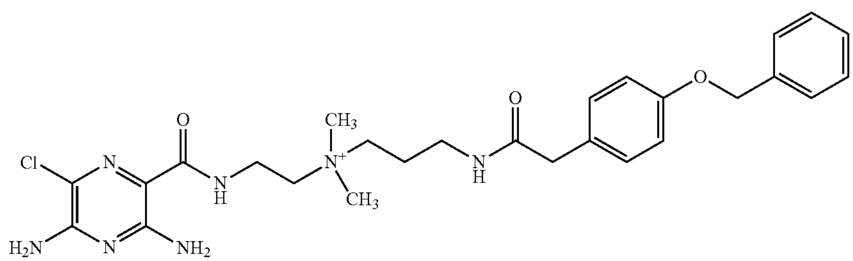 | 540 |
| 51 | 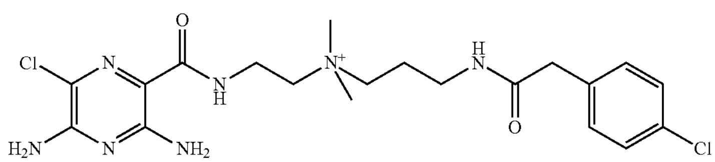 | 468 |
| 52 | 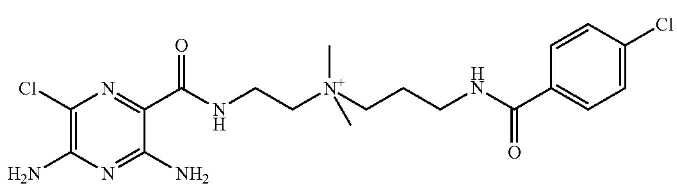 | 454 |
| 53 | 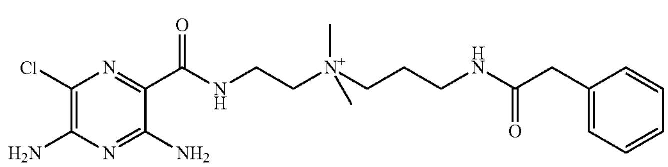 | 434 |
| 54 | 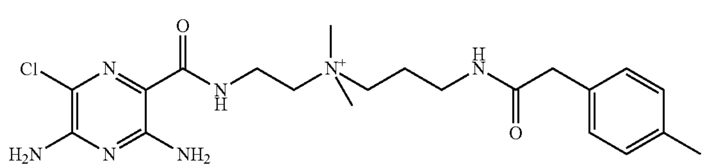 | 448 |

TABLE 1-continued

| Ex. | Structure | M+ |
|---|---|---|
| 55 | 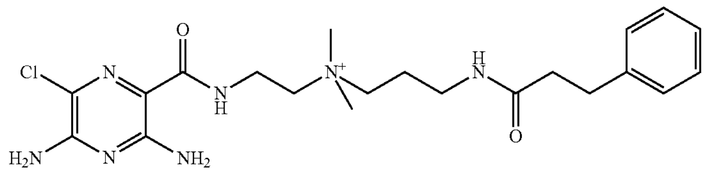 | 448 |
| 56 | 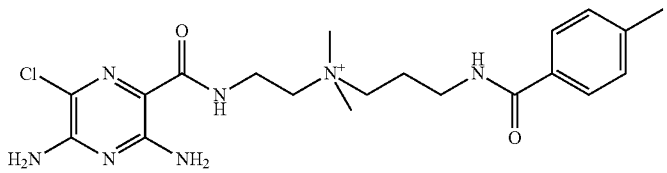 | 434 |
| 57 | 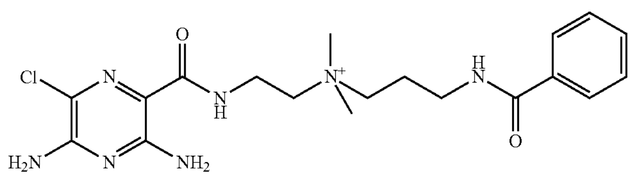 | 420 |
| 58 | 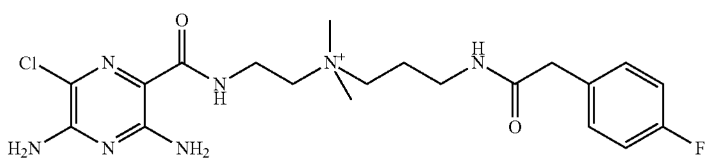 | 452 |
| 59 | 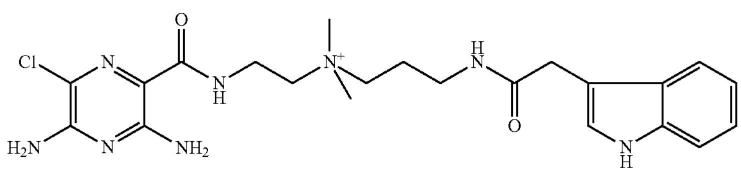 | 473 |
| 60 | 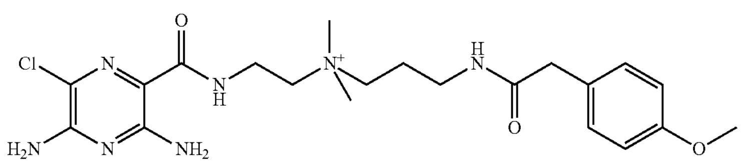 | 464 |
| 61 | 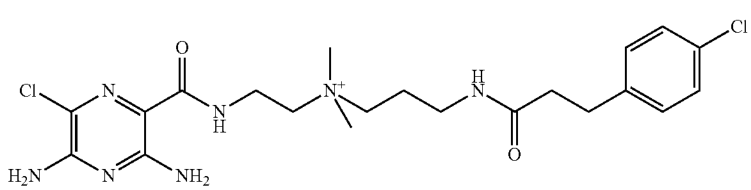 | 482 |
| 62 | 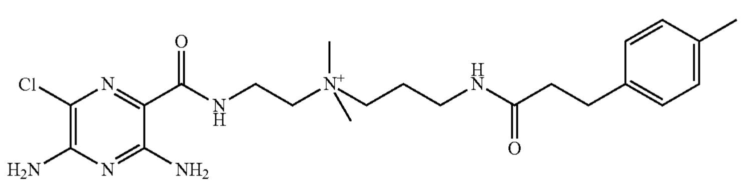 | 462 |

TABLE 1-continued

| Ex. | Structure | M+ |
|---|---|---|
| 63 | 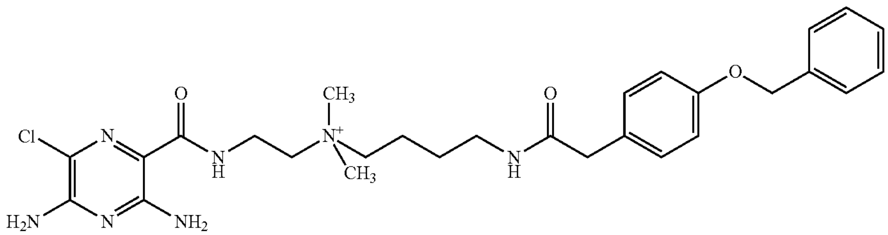 | 554 |
| 64 | 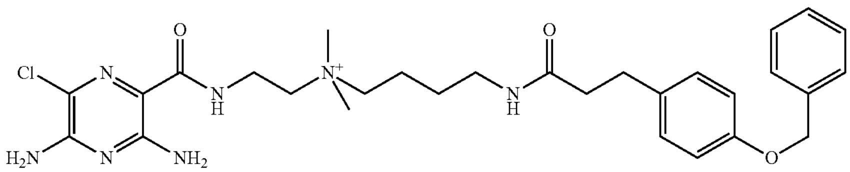 | 568 |
| 65 | 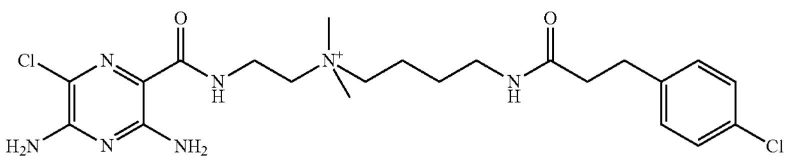 | 496 |
| 66 | 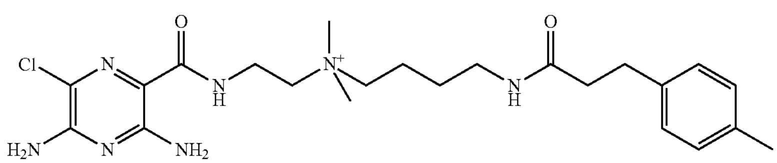 | 476 |
| 67 | 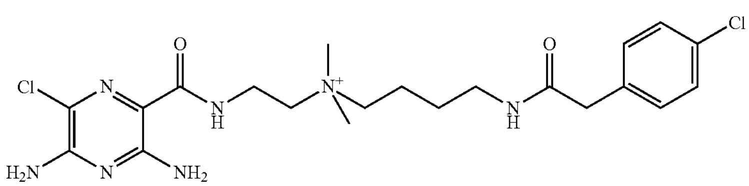 | 482 |
| 68 | 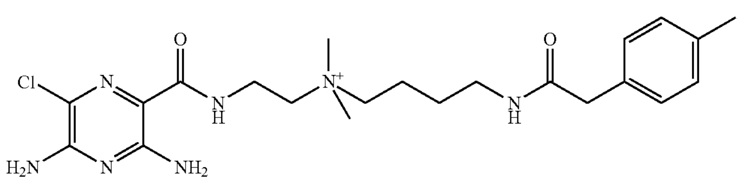 | 463 |
| 69 | 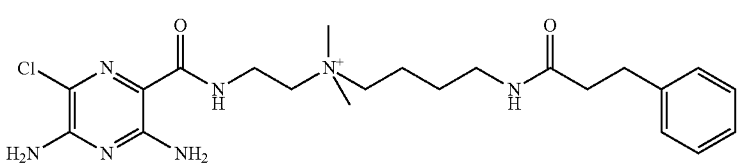 | 462 |

TABLE 1-continued

| Ex. | Structure | M+ |
|---|---|---|
| 70 | 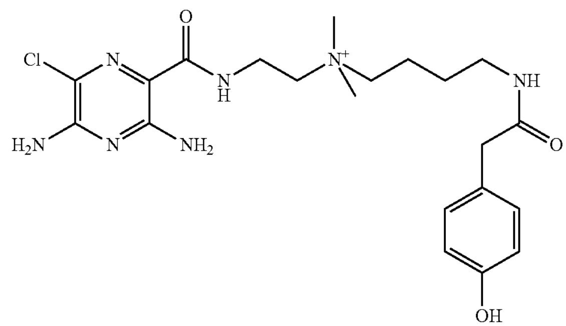 | 464 |
| 71 | 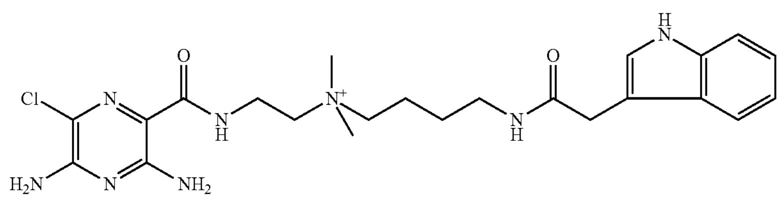 | 487 |
| 72 | 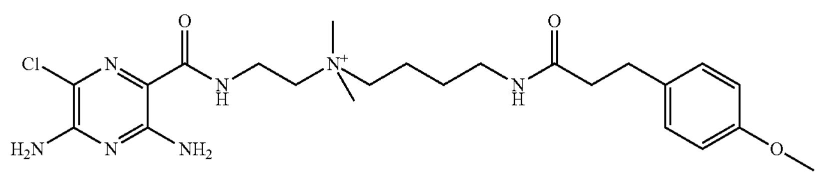 | 492 |
| 73 | 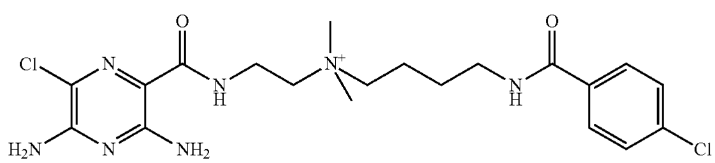 | 468 |
| 74 | 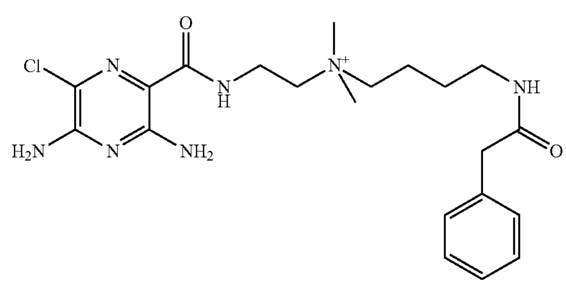 | 448 |
| 75 | 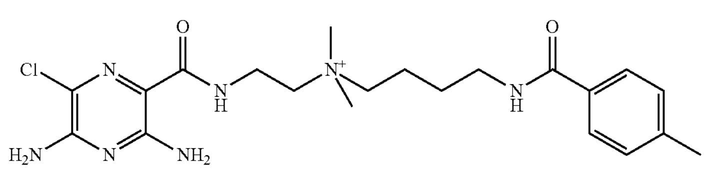 | 448 |
| 76 | 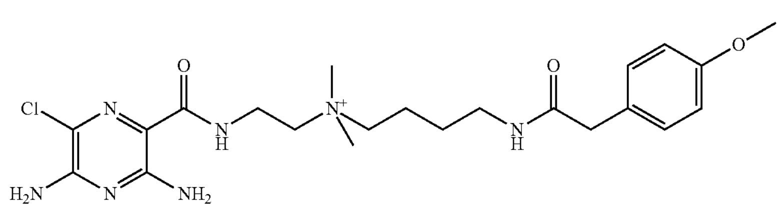 | 478 |

TABLE 1-continued

| Ex. | Structure | M+ |
|---|---|---|
| 77 | 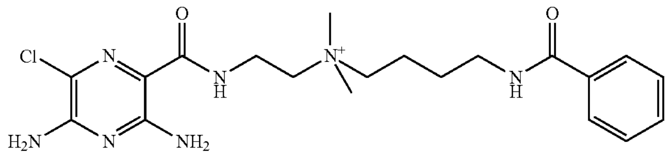 | 434 |
| 78 | 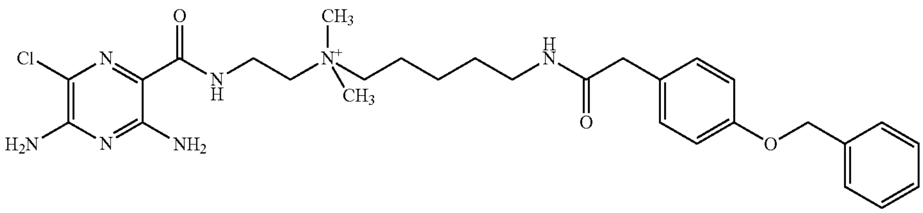 | 568 |
| 79 | 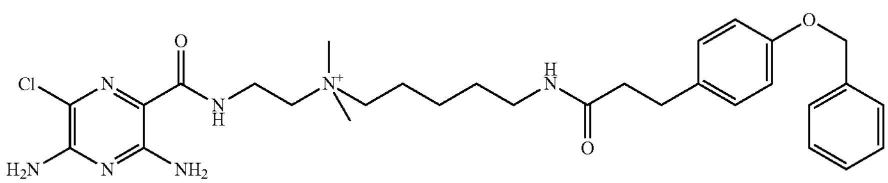 | 582 |
| 80 | 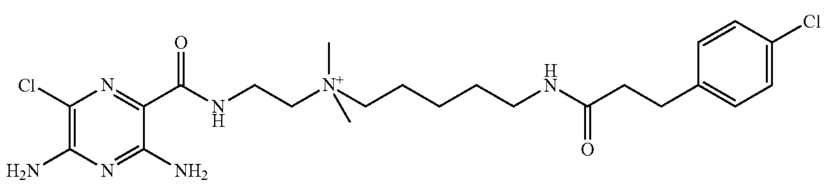 | 510 |
| 81 | 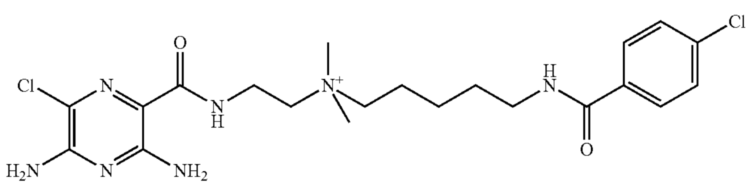 | 482 |
| 82 | 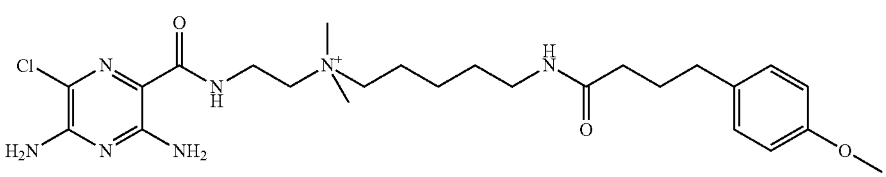 | 520 |
| 83 | 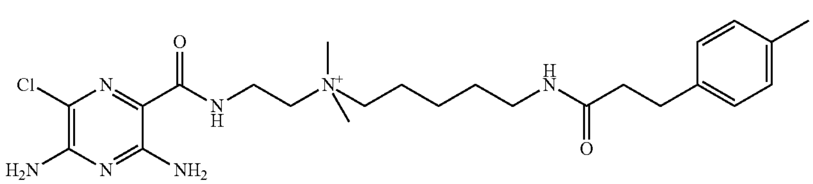 | 490 |
| 84 | 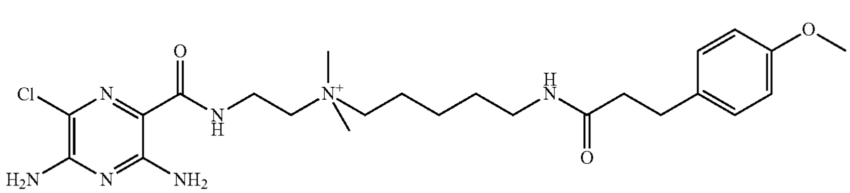 | 506 |

TABLE 1-continued
| Ex. | Structure | M+ |
|---|---|---|
| 85 | 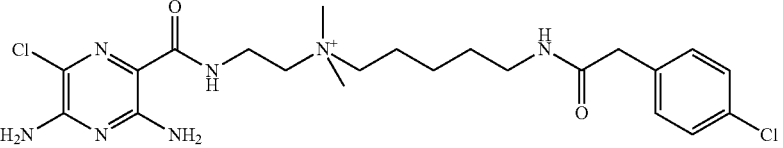 | 496 |
| 86 | 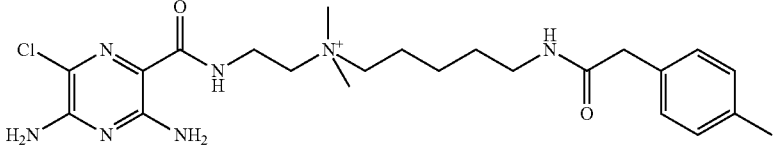 | 476 |
| 87 | 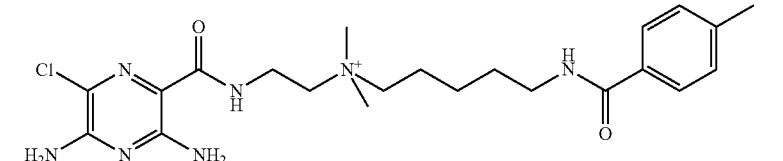 | 462 |
| 88 | 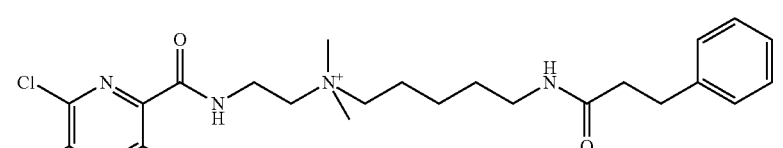 | 476 |
| 89 | 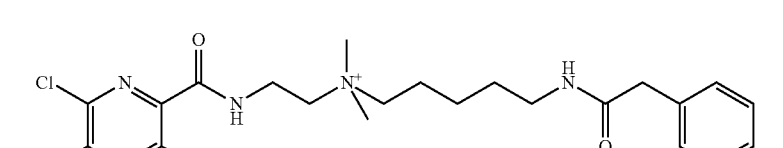 | 462 |
| 90 | 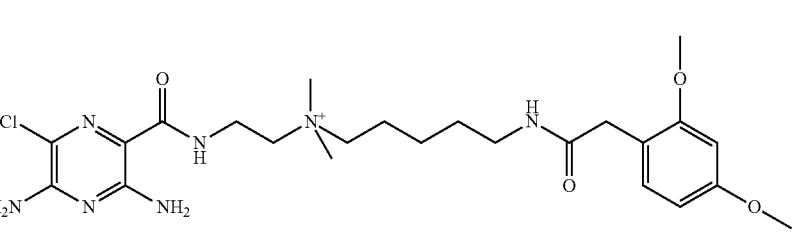 | 522 |
| 91 | 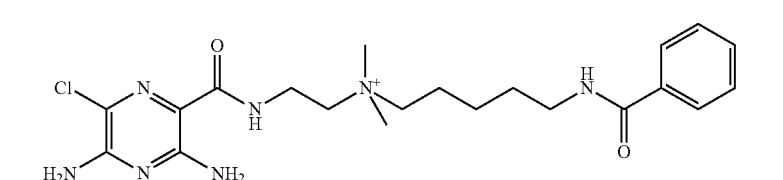 | 448 |
| 92 | 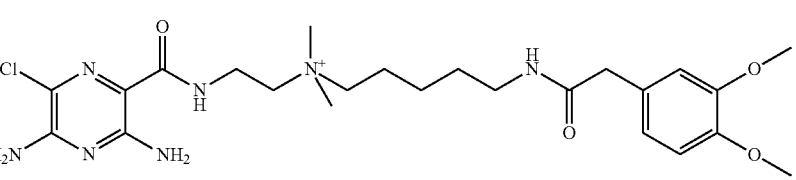 | 522 |

| Ex. | Structure | M+ |
|---|---|---|
| 93 | 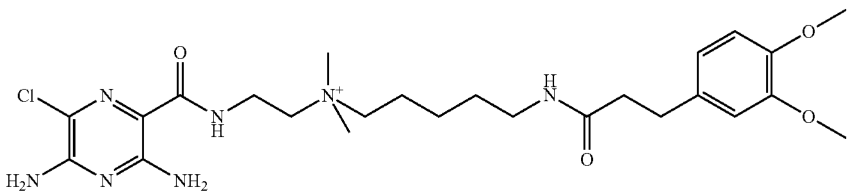 | 536 |
| 94 | 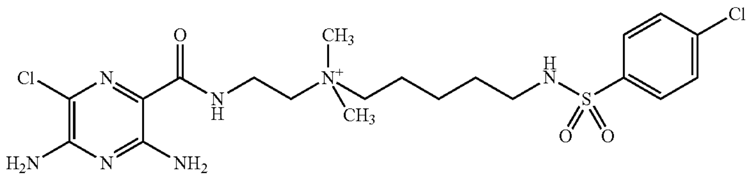 | 578 |
| 95 | 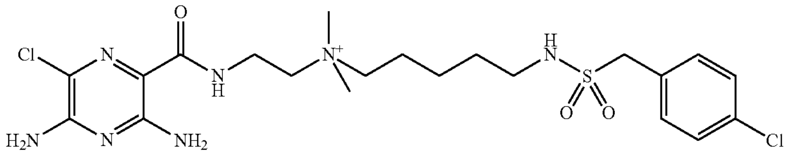 | 533 |
| 96 | 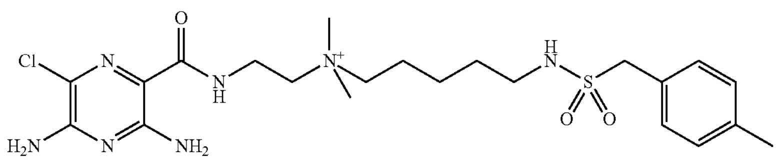 | 512 |
| 97 | 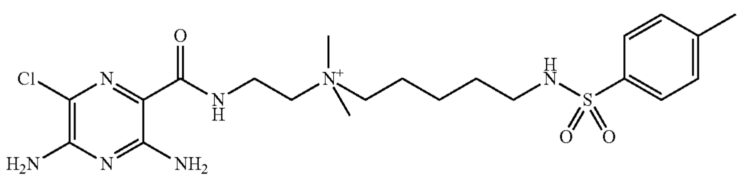 | 498 |
| 98 | 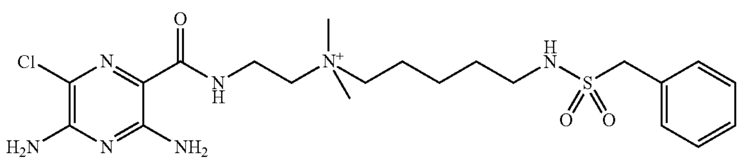 | 498 |
| 99 | 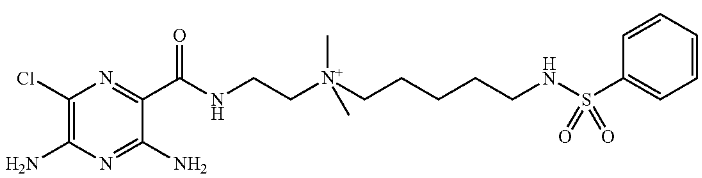 | 484 |
| 100 | 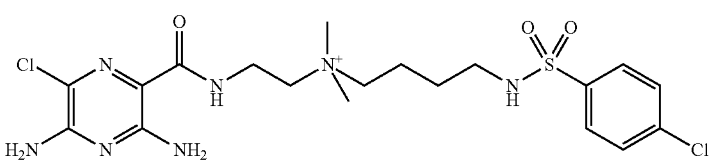 | 504 |
| 101 | 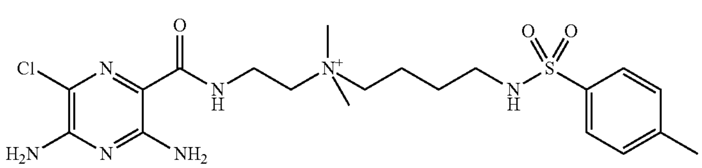 | 484 |

TABLE 1-continued
| Ex. | Structure | M+ |
|---|---|---|
| 102 | 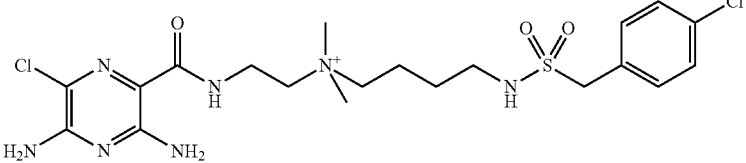 | 518 |
| 103 | 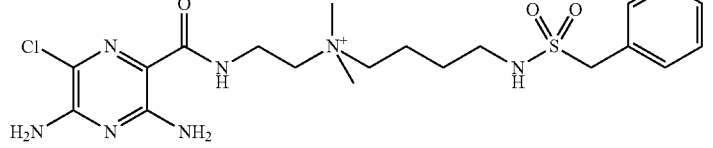 | 484 |
| 104 | 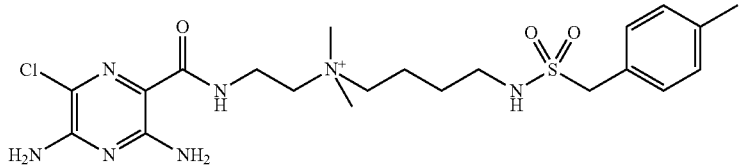 | 498 |
| 105 | 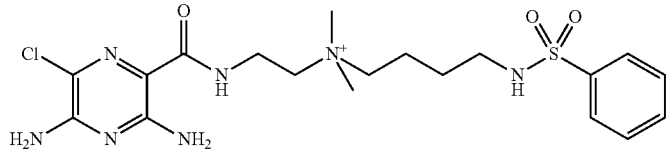 | 470 |
| 106 | 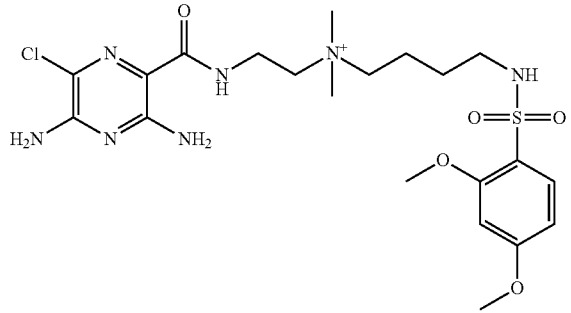 | 530 |
| 107 | 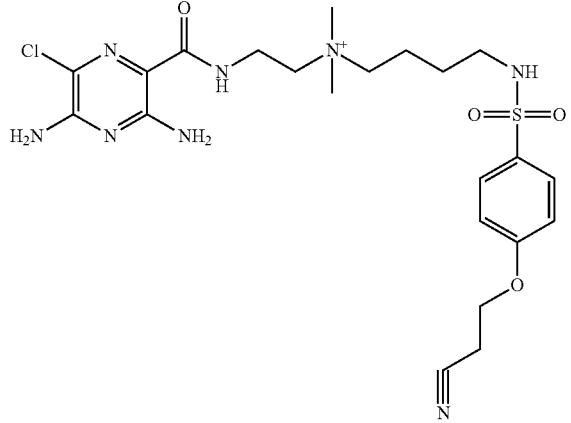 | 539 |

TABLE 1-continued

| Ex. | Structure | M⁺ |
|---|---|---|
| 108 | 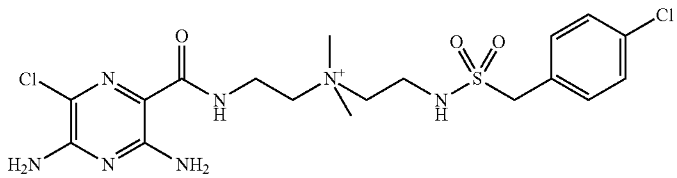 | 490 |
| 109 | 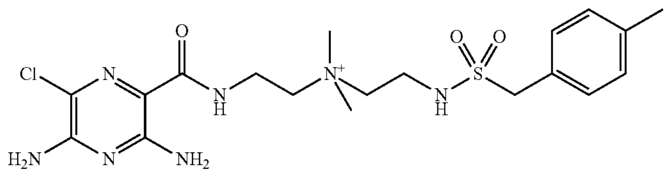 | 470 |
| 110 | 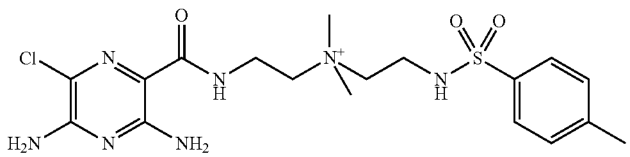 | 456 |
| 111 | 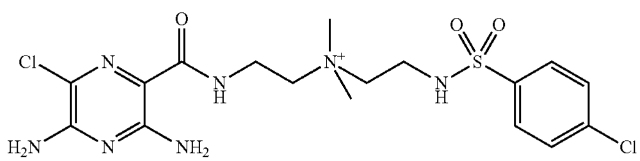 | 476 |
| 112 | 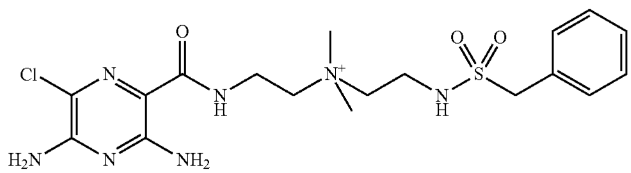 | 456 |
| 113 | 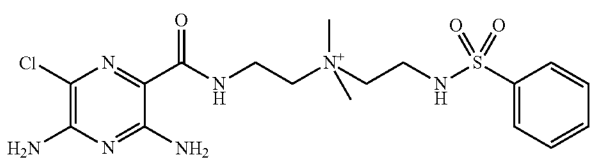 | 442 |
| 114 | 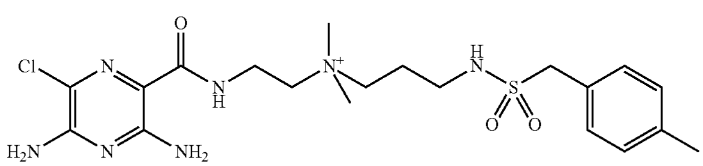 | 484 |
| 115 | 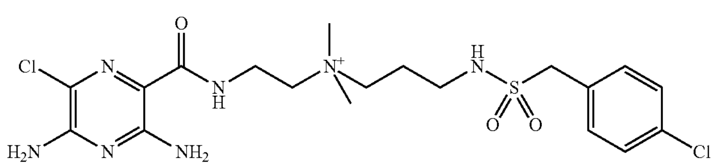 | 504 |
| 116 | 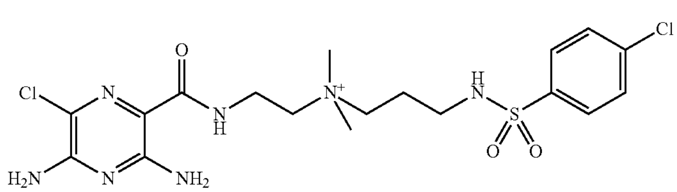 | 490 |

TABLE 1-continued

| Ex. | Structure | M+ |
|---|---|---|
| 117 | 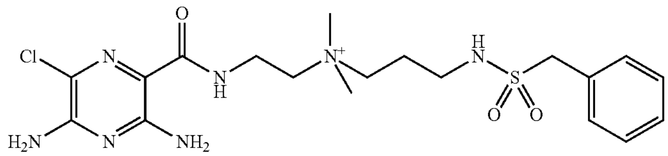 | 470 |
| 118 | 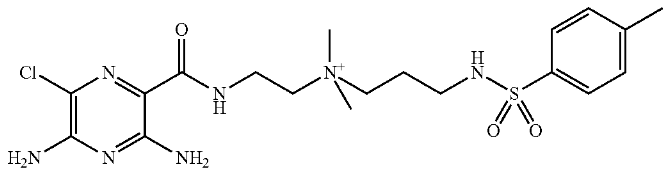 | 470 |
| 119 | 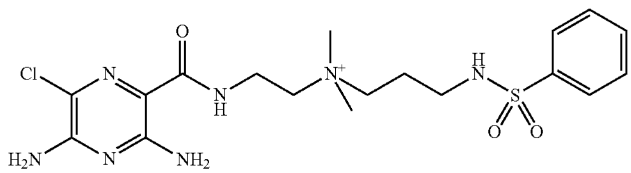 | 456 |
| 120 | 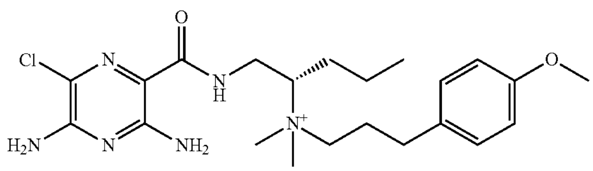 | 449 |
| 121 | 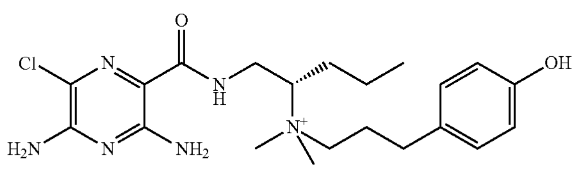 | 435 |
| 122 | 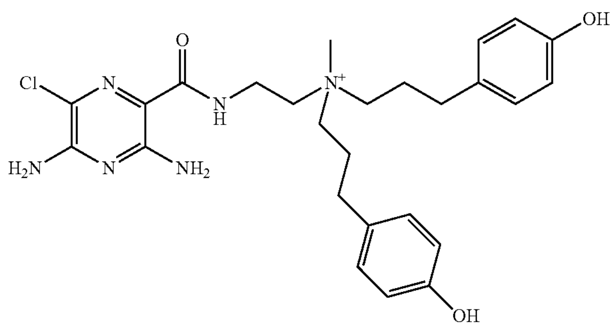 | 513 |
| 123 | 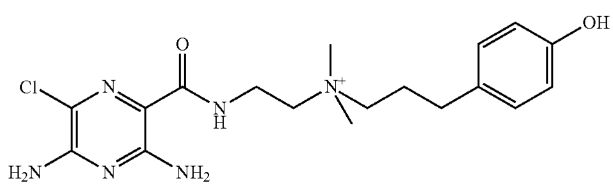 | 393 |
| 124 | 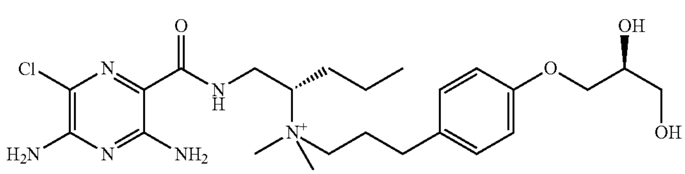 | 509 |

TABLE 1-continued

| Ex. | Structure | M+ |
|---|---|---|
| 125 | 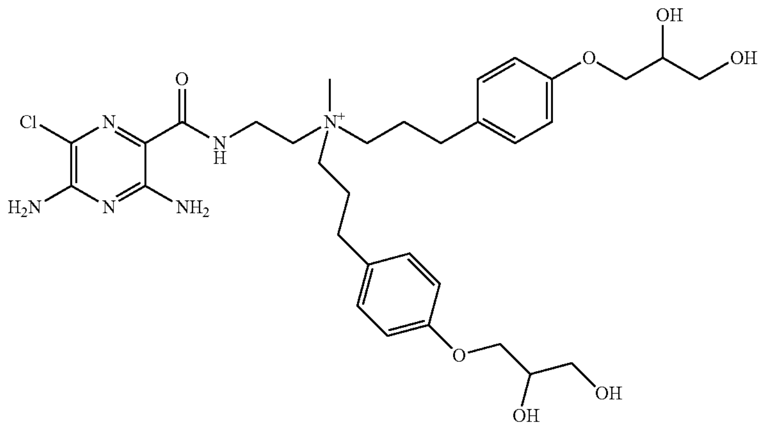 | 661 |
| 126 | 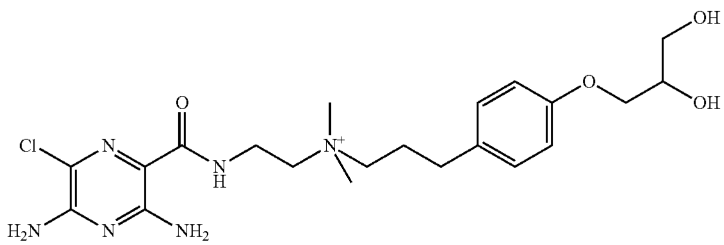 | 467 |
| 127 | 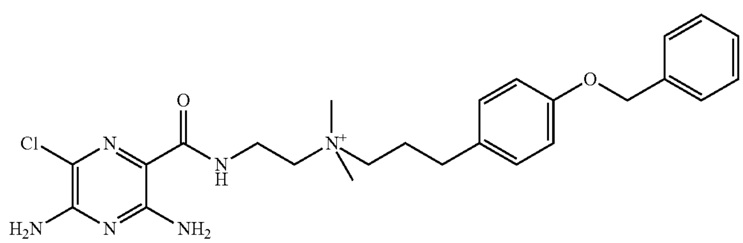 | 483 |
| 128 | 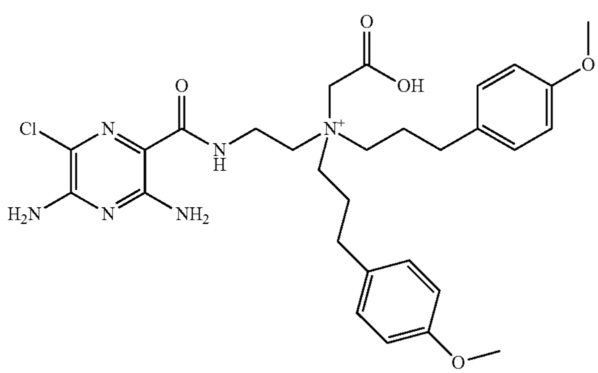 | 585 |
| 129 | 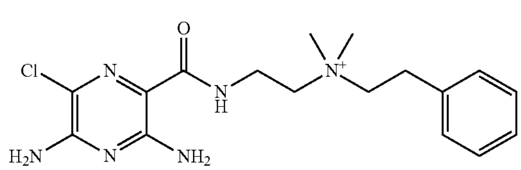 | 363 |
| 130 | 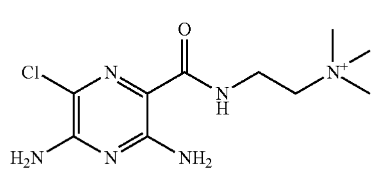 | 273 |

TABLE 1-continued

| Ex. | Structure | M+ |
|---|---|---|
| 131 | 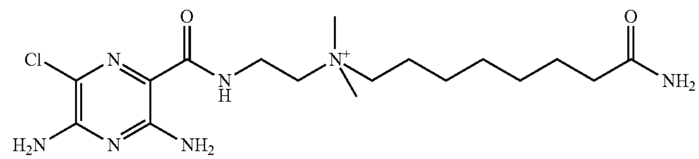 | 400 |
| 132 | 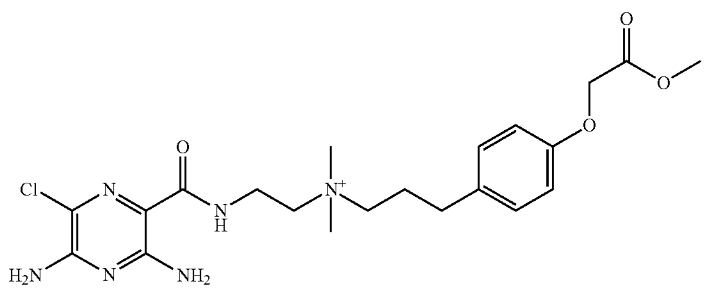 | 465 |
| 133 | 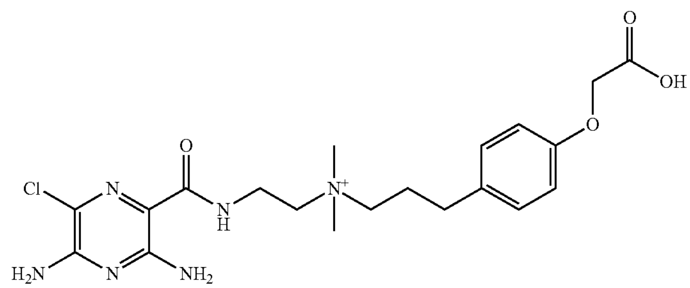 | 451 |

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

General Conditions:

Mass spectra are run on LCMS systems using electrospray ionization. These are either Agilent 1100 HPLC/Micromass Platform Mass Spectrometer combinations or Waters Acquity HPLC with SQD Mass Spectrometer. [M+H]+ and M+ refers to mono-isotopic molecular weights.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

In addition various trade reagents and materials available have been utilized. Such reagents and materials include: [Iso-lute™ (available from Biotage) and Celite® (available from Aldrich)] and can be readily obtained from the suppliers indicated.

For the examples below as well as throughout the application, the following abbreviations have the following meanings. If not defined, the terms have their generally accepted meanings.

ABBREVIATIONS

RT room temperature
DMF dimethyl-formamide
THF tetrahydrofuran
MeOH methanol
DCM dichloromethane
EtOAc ethyl acetate
EtOH ethanol
LCMS liquid chromatographic mass spectroscopy
TEA triethylamine
TFA trifluoroacetic acid
HPLC high performance liquid chromatography
DMSO dimethyl sulfoxide
Et$_3$N triethylamine
HPLC high performance liquid chromatography
HATU N—[(dimethylamino)-1H-1,2,3-triazolo[4,5-B]pyridin-1-ylmethylene]-N-methylmethanaminiumhexafluorophosphate
CDI 1,1'-carbonyl-diimidazole
DEAD diethylazodicarboxylate
PS polymer-supported
9-BBN 9-borabicyclo[3.3.1]nonane
dppf (diphenylphosphino)ferrocene

Preparation of Final Compounds

Example 1

((R)-1-{[(3,5-Diamino-6-chloro-pyrazine-2-carbonyl)-amino]-methyl}-butyl)-trimethyl-ammonium iodide

Step 1: [(R)-1-(1,3-Dioxo-1,3-dihydro-isoindol-2-ylmethyl)-butyl]-carbamic acid tert-butyl ester To a mixture of phthalimide (1.43 g, 9.72 mmol), ((R)-1-hydroxymethyl-butyl)-carbamic acid tert-butyl ester (prepared according to the procedure described in Tetrahedron Letters (1987), 28(48), 6069-72) (1.97 g, 9.69 mmol) and triphenylphosphine (2.55 g, 9.72 mmol) in DCM (25 mL) at 0° C. is added DEAD (1.6 mL, 10.2 mmol) dropwise. The reaction mixture is stirred at RT overnight. The reaction mixture is adsorbed onto silica gel and purification by column chromatography (SiO$_2$, EtOAc/iso-hexane, gradient of 0-15% EtOAc) affords the title compound as white solid. [M+H]$^+$ 233.

Step 2: ((R)-1-Aminomethyl-butyl)-carbamic acid tert-butyl ester

A mixture of [(R)-1-(1,3-dioxo-1,3-dihydro-isoindol-2-ylmethyl)-butyl]-carbamic acid tert-butyl ester (1.2 g, 3.61 mmol) and hydrazine monohydrate (1.0 mL, 20.6 mmol) in EtOH (25 mL) and DCM (75 mL) is stirred at RT for 48 h. The precipitated solid is removed by filtration and washed with DCM. The filtrate is concentrated in vacuo to afford the title compound as white solid that is used without further purification.

Step 3: ((R)-1-1{[(3,5-Diamino-6-chloro-pyrazine-2-carbonyl)-amino]-methyl}-butyl)-carbamic acid tert-butyl ester A mixture of ((R)-1-aminomethyl-butyl)-carbamic acid tert-butyl ester (0.70 g, 3.46 mmol), 3,5-diamino-6-chloro-pyrazine-2-carboxylic acid (0.65 g, 3.45 mmol), N-methyl-morpholine (1.5 mL, 13.6 mmol) and HATU (1.32 g, 3.47 mmol) in anhydrous DMF (50 mL) is stirred at RT for 16 h. The reaction mixture is concentrated in vacuo and the resulting residue is purified by column chromatography (basic alumina, 0-1% methanol in DCM) to afford the title compound as pale yellow solid. [M+H]$^+$ 373.

Step 4: 3,5-Diamino-6-chloro-pyrazine-2-carboxylic acid ((R)-2-amino-pentyl)-amide hydrochloride To a solution of ((R)-1-{[(3,5-diamino-6-chloro-pyrazine-2-carbonyl)-amino]-methyl}-butyl)-carbamic acid tert-butyl ester (0.65 g, 1.74 mmol) in 1,4-dioxane (15 mL) is added HCl (30 mL of a 4 M solution in 1,4-dioxane, 120 mmol) and the reaction mixture is stirred at RT for 16 h. The reaction mixture is concentrated in vacuo and the yellow solid obtained is triturated with diethyl ether; the ether layer is decanted and the product is dissolved in minimal MeOH and is precipitated by the addition of diethyl ether. The solvent is decanted and the resulting solid is dried under vacuum to afford the title compound. [M+H]$^+$ 273.

Step 5: ((R)-1-{[(3,5-Diamino-6-chloro-pyrazine-2-carbonyl)-amino]-methyl}-butyl)-trimethyl-ammonium iodide To a mixture of 3,5-Diamino-6-chloro-pyrazine-2-carboxylic acid ((R)-2-amino-pentyl)-amide hydrochloride (0.08 g, 0.26 mmol) and potassium carbonate (0.20 g, 1.45 mmol) in acetonitrile (15 mL) is added iodomethane (0.10 mL, 1.60 mmol). The reaction mixture is stirred at RT for 16 h after which time the reaction mixture is filtered through Celite® (filter material). The filtrate is concentrated and the resulting solid is dissolved in acetonitrile and filtered through Celite®. The filtrate is concentrated and then triturated with diethyl ether and the solvent is decanted. The resulting solid is dried under vacuum to afford the title compound as a yellow solid. M$^+$ 315. $^1$H NMR (400 MHz, DMSO) δ 8.30 (1H, t), 7.36 (2H, br), 7.10 (2H, br), 3.70-3.64 (1H, m), 3.51-3.43 (2H, m), 3.02 (9H, s), 1.85-1.79 (1H, m), 1.61-1.41 (3H, m), 0.92 (3H, t).

Example 2

((S)-1-{[(3,5-Diamino-6-chloro-pyrazine-2-carbonyl)-amino]-methyl}-propyl)-trimethyl-ammonium iodide The title compound is prepared by an analogous procedure to Example 1 by replacing ((R)-1-aminomethyl-butyl)-carbamic acid tert-butyl ester in Step 3 with ((S)-1-aminomethyl-propyl)-carbamic acid tert-butyl ester. M$^+$ 301.

Example 3

((R)-t-{[(3,5-Diamino-6-chloro-pyrazine-2-carbonyl)-amino]-methyl}-propyl)-trimethyl-ammonium iodide The title compound is prepared by an analogous procedure to Example 1 by replacing ((R)-1-aminomethyl-butyl)-carbamic acid tert-butyl ester in Step 3 with ((R)-1-aminomethyl-propyl)-carbamic acid tert-butyl ester (prepared according to the procedure described in WO2007125331, page 217-218). M$^+$ 301.

Example 4

((S)-1-{[(3,5-Diamino-6-chloro-pyrazine-2-carbonyl)-amino]-methyl}-pentyl)-trimethyl-ammonium iodide The title compound is prepared by an analogous procedure to Example 1 by replacing ((R)-1-hydroxymethyl-butyl)-carbamic acid tert-butyl ester in Step 1 with ((S)-1-hydroxymethyl-pentyl)-carbamic acid tert-butyl ester (prepared according to the procedure described in Tetrahedron Letters 1987, 28(48), 6069-72). M$^+$ 329.

Example 5

((S)-1-{[(3,5-Diamino-6-chloro-pyrazine-2-carbonyl)-amino]-methyl}-butyl)-trimethyl-ammonium trifluoroacetate The title compound is prepared by an analogous procedure to Example 1 by replacing ((R)-1-hydroxymethyl-butyl)-carbamic acid tert-butyl ester in Step 1 with ((S)-1-hydroxymethyl-butyl)-carbamic acid tert-butyl ester (prepared accord-

Example 6

((S)-1-{[(3,5-Diamino-6-chloro-pyrazine-2-carbonyl)-amino]-methyl}-2-methyl-propyl)-trimethyl-ammonium iodide The title compound is prepared by an analogous procedure to Example 1 by replacing ((R)-1-hydroxymethyl-butyl)-carbamic acid tert-butyl ester in Step 1 with N-(tert-butoxycarbonyl)-L-valinol. M$^+$ 315.

ing to the procedure described in US 2007/0032433 page 232). M$^+$ 315. $^1$H NMR (400 MHz, DMSO-d$_6$) δ 8.30 (1H, t), 7.20 (2H, br), 7.09 (2H, br), 3.73-3.62 (1H, m), 3.55-3.48 (2H, m), 3.08 (9H, s), 1.90-1.78 (1H, m), 1.65-1.47 (3H, m), 0.93 (3H, t).

Example 7

(R)-2-{[(3,5-Diamino-6-chloro-pyrazine-2-carbonyl)-amino]-methyl}-1,1-dimethyl-piperidinium iodide The title compound is prepared by an analogous procedure to Example 1 by replacing ((R)-1-aminomethyl-butyl)-carbamic acid tert-butyl ester in Step 3 with (R)-2-aminomethyl-1-N-Boc-piperidine. M$^+$ 313.

Example 8

(S)-2-{[(3,5-Diamino-6-chloro-pyrazine-2-carbonyl)-amino]-methyl}-1,1-dimethyl-piperidinium iodide The title compound is prepared by an analogous procedure to Example 1 by replacing ((R)-1-aminomethyl-butyl)-carbamic acid tert-butyl ester in Step 3 with (S)-2-aminomethyl-1-N-Boc-piperidine. M$^+$ 313.

Example 9

(1-{[(3,5-Diamino-6-chloro-pyrazine-2-carbonyl)-amino]-methyl}-cyclopentyl)-trimethyl-ammonium iodide The title compound is prepared by an analogous procedure to Example 1 by replacing ((R)-1-aminomethyl-butyl)-carbamic acid tert-butyl ester in Step 3 with (1-aminomethyl-cyclopentyl)-carbamic acid tert-butyl ester. M$^+$ 327. $^1$H NMR (400 MHz, DMSO-d$_6$) δ 8.27 (1H, t), 7.50 (2H, br), 7.12 (2H, br), 3.69 (2H, d), 3.09 (9H, s), 2.19-2.09 (2H, m), 1.95-1.88 (2H, m), 1.67-1.53 (4H, m).

Example 10

(S)-2-{[(3,5-Diamino-6-chloro-pyrazine-2-carbonyl)-amino]-methyl}-1,1-dimethyl-pyrrolidinium iodide The title compound is prepared by an analogous procedure to Example 1 by replacing ((R)-1-aminomethyl-butyl)-carbamic acid tert-butyl ester in Step 3 with (S)-2-aminomethyl-1-N-Boc-pyrrolidine. M$^+$ 299.

Example 11

(R)-2-{[(3,5-Diamino-6-chloro-pyrazine-2-carbonyl)-amino]-methyl}-1,1-dimethyl-pyrrolidinium iodide The title compound is prepared by an analogous procedure to Example 1 by replacing ((R)-1-aminomethyl-butyl)-carbamic acid tert-butyl ester in Step 3 with (R)-2-aminomethyl-1-N-Boc-pyrrolidine. M$^+$ 299. $^1$H NMR (400 MHz, DMSO-d$_6$) δ 8.39 (1H, t), 7.60 (2H, br), 7.10 (2H, br), 3.81-3.71 (1H, m), 3.69-3.43 (4H, m), 3.11 (3H, s), 3.00 (3H, s), 2.23-2.19 (1H, m), 2.05-1.88 (3H, m).

Example 12

{(S)-2-[(3,5-Diamino-6-chloro-pyrazine-2-carbonyl)-amino]-1-methyl-ethyl}-trimethyl-ammonium iodide The title compound is prepared by an analogous procedure to Example 1 by replacing ((R)-1-hydroxymethyl-butyl)-carbamic acid tert-butyl ester in Step 1 with ((S)-2-hydroxy-1-methyl-ethyl)-carbamic acid tert-butyl ester. M$^+$ 287.

Example 13

{(S)-1-Benzyl-2-[(3,5-diamino-6-chloro-pyrazine-2-carbonyl)-amino]-ethyl}-trimethyl-ammonium iodide The title compound is prepared using an analogous procedure to Example 1 by replacing 3,5-diamino-6-chloro-pyrazine-2-carboxylic acid ((R)-2-amino-pentyl)-amide hydrochloride in Step 4 with 3,5-diamino-6-chloro-pyrazine-2-carboxylic acid ((S)-2-amino-3-phenyl-propyl)-amide (Intermediate A). M$^+$ 363. $^1$H NMR (400 MHz, CD$_3$OD) δ 7.54-7.00 (5H, m), 3.85-3.56 (2H, m), 3.57 (1H, dd), 3.41-3.33 (m, 2H), 3.22 (9H, s).

Example 14

((S)-5-[3-(4-Benzyloxy-phenyl)-propionylamino]-1-{[(3,5-diamino-6-chloro-pyrazine-2-carbonyl)-amino]-methyl}-pentyl)-trimethyl-ammonium iodide Step 1: ((S)-5-[3-(4-Benzyloxy-phenyl)-propionylamino]-1-{[(3,5-diamino-6-chloro-pyrazine-2-carbonyl)-amino]-methyl}-pentyl)-carbamic acid tert-butyl ester To a solution of 3-(4-benzyloxyphenyl)propionic acid (0.19 g, 0.74 mmol) and HATU (0.29 g, 0.75 mmol) in DMF (10 mL) is added N-methylmorpholine (0.32 mL, 2.91 mmol) followed by ((S)-5-amino-1-{[(3,5-diamino-6-chloro-pyrazine-2-carbonyl)-amino]-methyl}-pentyl)-carbamic acid tert-butyl ester (Intermediate B) (0.30 g, 0.75 mmol). The resulting mixture is stirred at RT for 16 h. The solvent is removed in vacuo and the residue is purified by column chromatography (basic alumina, 2% MeOH in DCM) to afford the title compound as yellow solid. [M-Boc+H]+ 540.

Step 2: 3,5-Diamino-6-chloro-pyrazine-2-carboxylic acid {(S)-2-amino-6-[3-(4-benzyloxy-phenyl)-propionylamino]-hexyl}-amide hydrochloride A solution of ((S)-5-[3-(4-benzyloxy-phenyl)-propionylamino]-1-{[(3,5-diamino-6-chloro-pyrazine-2-carbonyl)-amino]-methyl}-pentyl)-carbamic acid tert-butyl ester (0.29 g, 0.45 mmol) in 1,4-dioxane (3 mL) and HCl (5 mL of a 4 M solution in 1,4-dioxane, 20 mmol) is stirred at RT for 2 h. The solvent is removed in vacuo and the resulting residue is triturated with diethyl ether and then the diethyl ether is decanted. The remaining solid is dissolved in a minimal amount of MeOH then diethyl ether is added to cause precipitation. The supernatant solvents are decanted and the remaining solid is washed with diethyl ether then dried under vacuum to afford the title compound as yellow solid. [M+H]+ 540.

Step 3: ((S)-5-[3-(4-Benzyloxy-phenyl)-propionylamino]-1-{[(3,5-diamino-6-chloro-pyrazine-2-carbonyl)-amino]-methyl}-pentyl)-trimethyl-ammonium iodide The title compound is prepared using an analogous procedure to Example 1 by replacing 3,5-diamino-6-chloro-pyrazine-2-carboxylic acid ((R)-2-amino-pentyl)-amide hydrochloride in Step 5 with 3,5-diamino-6-chloro-pyrazine-2-carboxylic acid {(S)-2-amino-6-[3-(4-benzyloxy-phenyl)-propionylamino]-hexyl}-amide hydrochloride M+ 582.

Example 15

((S)-5-[2-(4-Benzyloxy-phenyl)-acetylamino]-1-{[(3,5-diamino-6-chloro-pyrazine-2-carbonyl)-amino]-methyl}-pentyl)-trimethyl-ammonium iodide The title compound is prepared using an analogous procedure to Example 14 by replacing 3-(4-benzyloxyphenyl)propionic acid in Step 1 with (4-benzyloxy-phenyl)-acetic acid. M+ 568. $^1$H NMR (400 MHz, DMSO-$d_6$) δ 8.31 (1H, t), 7.97 (1H, t), 7.42-7.31 (4H, m), 7.14 (2H, d), 7.13-7.09 (1H, m), 7.05 (4H, br), 6.90 (2H, d), 5.04 (2H, s), 3.50-3.40 (4H, m), 3.30 (2H, s), 3.05 (9H, s), 1.49-1.32 (6H, m).

Example 16

4-Benzyl-1-{2-[(3,5-diamino-6-chloro-pyrazine-2-carbonyl)-amino]-ethyl}-1-methyl-piperidinium iodide Step 1: 3,5-Diamino-6-chloro-pyrazine-2-carboxylic acid [2-(4-benzyl-piperidin-1-yl)-ethyl]amide A solution of 3,5-diamino-6-chloro-pyrazine-2-carboxylic acid (0.10 g, 0.53 mmol) and CDI (0.172 g, 1.06 mmol) in DMF (2 mL) is stirred at RT for 1 h. To this reaction mixture is added 2-(4-benzylpiperidinol)-1-ethanamine (0.139 g, 0.63 mmol) and stirring is continued at RT for a further 48 h. The reaction mixture is diluted with water (20 mL) and extracted with EtOAc (3×20 mL). The combined organic portions are dried (MgSO$_4$) and concentrated in vacuo to afford a yellow solid which is recrystallised from acetonitrile to yield the title compound as off-white crystals. [M+H]+ 389.

Step 2: 4-Benzyl-1-{2-[(3,5-diamino-6-chloro-pyrazine-2-carbonyl)-amino]-ethyl}-1-methyl-piperidinium iodide A solution of 3,5-diamino-6-chloro-pyrazine-2-carboxylic acid [2-(4-benzyl-piperidin-1-yl)-ethyl]-amide (39 mg, 0.10 mmol) and methyl iodide (0.031 mL, 0.50 mmol) in acetone (2 mL) is heated at reflux for 3 h. After cooling to RT the solvent is removed in vacuo to afford the title compound as yellow solid. M+ 403. $^1$H NMR (400 MHz, DMSO-$d_6$) δ 8.30 (1H, t), 7.62 (2H, br), 7.39-7.36 (2H, m), 7.29-7.23 (3H, m), 7.16 (2H, br), 3.73-3.47 (6H, m), 3.35-3.28 (2H, m), 3.14 (3H, s), 2.67 (2H, d), 1.92-1.81 (1H, m), 1.74-1.68 (4H, m).

Example 17

Allyl-{2-[(3,5-diamino-6-chloro-pyrazine-2-carbonyl)-amino]-ethyl}-bis-[3-(4-methoxy-phenyl)-propyl]-ammonium trifluoroacetate To a solution of 3,5-diamino-6-chloro-pyrazine-2-carboxylic acid (2-{bis-[3-(4-methoxy-phenyl)-propyl]-amino}-ethyl)-amide trifluoroacetate (Intermediate D) (0.20 g, 0.31 mmol) in acetone (5 mL) is added sodium carbonate (99 mg, 0.94 mmol) followed by allyl bromide (0.082 mL, 0.94 mmol). The reaction mixture is heated at reflux for 72 h, cooled to RT then filtered to remove inorganic salts. The filtrate is concentrated and purification by reverse phase column chromatography (Isolute™ C18, 0-100% acetonitrile in water with 0.1% TFA) affords the title compound. M+ 567. $^1$H NMR (400 MHz, DMSO-$d_6$) δ 8.32 (1H, t), 7.76 (2H, br), 7.16 (2H, br), 7.11 (4H, d), 6.85 (4H, d), 5.95 (1H, ddt) 5.62 (1H, d), 5.57 (1H, d), 3.99 (2H, d), 3.72 (6H, s), 3.58-3.54 (2H, m), 3.30 (2H, t), 3.24-3.20 (4H, m), 2.50 (4H, t), 1.97-1.78 (4H, m).

Example 18

{2-[(3,5-Diamino-6-chloro-pyrazine-2-carbonyl)-amino]-ethyl}-tris-[3-(4-methoxy-phenyl)-propyl]-ammonium trifluoroacetate The title compound is prepared using an analogous procedure to Example 17 by replacing allyl bromide with 1-(3-bromo-propyl)-4-methoxy-benzene. M+ 675. $^1$H NMR (400 MHz, CD$_3$OD) 7.07 (6H, d), 6.83 (6H, d), 3.88 (9H, s), 3.59 (2H, t), 3.39 (2H, t), 3.26-3.21 (6H, m), 2.54 (6H, t), 1.80 (6H, m).

Example 19

{2-[(3,5-Diamino-6-chloro-pyrazine-2-carbonyl)-amino]-ethyl}-(2-diethylamino-ethyl)-bis-[3-(4-methoxy-phenyl)-propyl]-ammonium trifluoroacetate The title compound is prepared using an analogous procedure to Example 17 by replacing allyl bromide with diethylaminoethyl bromide. M+ 626.

Example 20

{2-[(3,5-Diamino-6-chloro-pyrazine-2-carbonyl)-amino]-ethyl}-bis-[3-(4-methoxy-phenyl)-propyl]-methyl-ammonium trifluoroacetate The title compound is prepared using an analogous procedure to Example 17 by replacing allyl bromide with methyl iodide. M+ 541. ¹H NMR (400 MHz, DMSO-d₆) δ 8.32 (1H, t), 7.75 (2H, br), 7.14 (4H, d), 6.97 (2H, br), 6.83 (4H, d), 3.73 (6H, s), 3.57 (2H, dt), 3.38 (2H, t), 3.34-3.41 (4H, m), 3.03 (3H, s), 2.49 (4H, t), 1.94-1.87 (4H, m).

Example 21

{2-[(3,5-Diamino-6-chloro-pyrazine-2-carbonyl)-amino]-ethyl}-bis-[3-(4-methoxy-phenyl)-propyl]-propyl-ammonium trifluoroacetate The title compound is prepared using an analogous procedure to Example 17 by replacing allyl bromide with propyl iodide. M+ 569.

Example 22

Carbamoylmethyl-{2-[(3,5-diamino-6-chloro-pyrazine-2-carbonyl)-amino]-ethyl}-bis-[3-(4-methoxy-phenyl)-propyl]-ammonium trifluoroacetate The title compound is prepared using an analogous procedure to Example 17 by replacing allyl bromide with 2-bromoacetamide. M+ 584.

Example 23

Benzyl-{2-[(3,5-diamino-6-chloro-pyrazine-2-carbonyl)-amino]-ethyl}-bis-[3-(4-methoxy-phenyl)-propyl]-ammonium trifluoroacetate The title compound is prepared using an analogous procedure to Example 17 by replacing allyl bromide with benzyl bromide. M+ 617.

Example 24

{2-[(3,5-Diamino-6-chloro-pyrazine-2-carbonyl)-amino]-ethyl}-methoxycarbonylmethyl-bis-[3-(4-methoxy-phenyl)-propyl]-ammonium trifluoroacetate The title compound is prepared using an analogous procedure to Example 17 by replacing allyl bromide with methyl bromoacetate. M+ 599.

Example 25

{2-[(3,5-Diamino-6-chloro-pyrazine-2-carbonyl)-amino]-ethyl}-ethyl-bis-[3-(4-methoxy-phenyl)-propyl]-ammonium trifluoroacetate The title compound is prepared using an analogous procedure to Example 17 by replacing allyl bromide with ethyl iodide. M+ 555.

Example 26

{4-[3-(3-Chloro-4-ethoxy-phenyl)-ureido]-butyl}-{2-[(3,5-diamino-6-chloro-pyrazine-2-carbonyl)-amino]-ethyl}-[3-(4-methoxy-phenyl)-propyl]-methyl-ammonium bromide Step 1: 3,5-Diamino-6-chloro-pyrazine-2-carboxylic acid [2-({4-[3-(3-chloro-4-ethoxy-phenyl)-ureido]-butyl}-methyl-amino)-ethyl]-amide trifluoroacetate A mixture comprising 3,5-diamino-6-chloro-pyrazine-2-carboxylic acid {2-[(4-amino-butyl)-methyl-amino]-ethyl}-amide (Intermediate F), (0.20 g, 0.63 mmol) and 1-ethoxy-2-chloro-4-isocyanato-benzene (Intermediate G) (0.91 g, 0.95 mmol) in DMF (3 mL) is stirred under an inert atmosphere of argon at 50° C. for 48 h. Purification by reverse phase column chromatography (Isolute™ C18, 0-100% acetonitrile in water with 0.1% TFA) affords the title compound. [M+H]+ 513.

Step 2: {4-[3-(3-Chloro-4-ethoxy-phenyl)-ureido]-butyl}-{2-[(3,5-diamino-6-chloro-pyrazine-2-carbonyl)-amino]-ethyl}-[3-(4-methoxy-phenyl)-propyl]-methyl-ammonium bromide A mixture comprising 3,5-diamino-6-chloro-pyrazine-2-carboxylic acid [2-({4-[3-(3-chloro-4-ethoxy-phenyl)-ureido]-butyl}-methyl-amino)-ethyl]-amide trifluoroacetate (435 mg, 0.85 mmol), 1-(3-bromo-propyl)-4-methoxy-benzene (1.83 g, 7.99 mmol) and sodium carbonate (270 mg, 2.54 mmol) in acetone (8 mL) is heated at reflux for 11 days. After cooling to RT, the mixture is filtered and concentrated in vacuo. DCM is added and the precipitated solid is collected by filtration. The solid is crystallised from ethanol to afford the title compound. M+ 661. ¹H NMR (400 MHz, DMSO-d₆) δ 8.50 (1H, s), 8.29 (1H, t), 7.63 (2H, br), 7.62 (1H, d), 7.15 (1H, dd), 7.10 (2H, d), 6.99 (1H, d), 6.93 (2H, br), 6.81 (2H, d), 6.23 (1H, t), 4.01 (2H, q), 3.71 (3H, s), 3.61-3.56 (2H, m), 3.39-3.29 (4H, m), 3.08 (2H, q), 3.03 (3H, s), 2.49 (2H, t), 2.00-1.91 (2H, m), 1.72-1.64 (2H, m), 1.42 (2H, quint), 1.32 (3H, t).

Example 27

{2-[(3,5-Diamino-6-chloro-pyrazine-2-carbonyl)-amino]-ethyl}-[3-(4-methoxy-phenyl)-propyl]-dimethyl-ammonium bromide A mixture comprising 3,5-diamino-6-chloro-pyrazine-2-carboxylic acid (2-dimethylamino-ethyl)-amide (Intermediate H) (1.8 g, 7.0 mmol) and 1-(3-bromo-propyl)-4-methoxy-benzene (3.2 g, 14.0 mmol) in acetone (50 mL) is heated at reflux for 72 h. After cooling to RT, the solvent is removed in vacuo and the resulting solid is recrystallised from ethanol to afford the title compound. M+ 407. ¹H NMR (400 MHz, DMSO-d₆) δ 8.37 (1H, t), 7.76 (2H, br), 7.19 (2H, br), 7.17 (2H, d), 6.90 (2H, d), 3.79 (3H, s), 3.67 (2H, q), 3.49 (2H, t), 3.15 (6H, s), 2.55 (2H, t), 2.02 (2H, quintet).

Example 28

{2-[(3,5-Diamino-6-chloro-pyrazine-2-carbonyl)-amino]-ethyl}-{2-[3-(4-isobutoxy-phenyl)-ureido]-ethyl}-dimethyl-ammonium chloride The title compound is prepared using an analogous procedure to Example 27 by replacing 1-(3-bromo-propyl)-4-methoxy-benzene with 1-(2-chloro-ethyl)-3-(4-isobutoxy-phenyl)-urea (Intermediate I). M+ 493.

Example 29

{2-[(3,5-Diamino-6-chloro-pyrazine-2-carbonyl)-amino]-ethyl}-[3-(4-{3-[4-((S)-2,3-dihydroxy-propoxy)-phenyl]-propoxy}-phenyl)-propyl]-dimethyl-ammonium bromide 3,5-Diamino-6-chloro-pyrazine-2-carboxylic acid (2-dimethylamino-ethyl)-amide (Intermediate H) (0.65 g, 2.52 mmol) and (S)-3-(4-{3-[4-(3-bromo-propyl)-phenoxy]-propyl}-phenoxy)-propane-1,2-diol (Intermediate J) (1.60 g, 3.78 mmol) in butan-2-one (25 mL) is heated at reflux overnight during which time precipitation of white solid is observed. The reaction mixture is filtered to collect the product, washed with warm acetone and dried under vacuum to afford the title compound. $M^+$ 601. $^1H$ NMR (400 MHz, DMSO-$d_6$) δ 8.29 (1H, t), 7.30 (1H, br), 7.12 (2H, d), 7.11 (2H, br), 7.07 (2H, d), 6.95 (1H, br), 6.84 (2H, d), 6.82 (2H, d), 4.89 (1H, d), 4.63 (1H, t), 3.94 (1H, dd), 3.89 (2H, t), 3.81 (1H, dd), 3.77 (1H, m), 3.59 (2H, m), 3.43 (2H, m), 3.42 (2H, m), 3.34 (2H, m), 3.08 (6H, s), 2.66 (2H, m), 2.47 (2H, m), 1.96 (2H, m), 1.93 (2H, m).

Example 30

{2-[(3,5-Diamino-6-chloro-pyrazine-2-carbonyl)-amino]-ethyl}-dimethyl-2-[(3-phenyl-propionylamino)-ethyl]-ammonium hexafluorophosphate A mixture of (2-amino-ethyl)-{2-[(3,5-diamino-6-chloro-pyrazine-2-carbonyl)-amino]-ethyl}-dimethyl-ammonium bromide (Intermediate K) (0.50 g, 1.31 mmol), 3-phenylpropionic acid (0.20 g, 1.33 mmol), N-methylmorpholine (0.60 mL, 5.46 mmol) and HATU (0.50 g, 1.33 mmol) in anhydrous DMF (10 mL) is stirred under a nitrogen atmosphere at RT for 16 h. The reaction mixture is concentrated in vacuo and is purified by column chromatography (basic alumina, 0-3% MeOH in DCM) to afford the title compound. $M^+$ 434. $^1H$ NMR (400 MHz, DMSO-$d_6$) δ 8.26 (1H, t), 8.16 (1H, t), 7.40 (2H, br), 7.28-7.23 (2H, m), 7.20-7.17 (3H, m), 7.15 (2H, br), 3.62-3.59 (2H, m), 3.49-3.29 (6H, m), 3.07 (6H, s), 2.81 (2H, t), 2.41 (2H, t).

Example 31

{2-[(3,5-Diamino-6-chloro-pyrazine-2-carbonyl)-amino]-ethyl}-[2-(2-1H-indol-3-yl-acetylamino)-ethyl]-dimethyl-ammonium hexafluorophosphate The title compound is prepared using an analogous procedure to Example 30 by replacing 3-phenylpropionic acid with (1H-indol-3-yl)-acetic acid. $M^+$ 459.

Example 32

{2-[2-(4-Benzyloxy-phenyl)-acetylamino]-ethyl}-{2-[(3,5-diamino-6-chloro-pyrazine-2-carbonyl)-amino]-ethyl}-dimethyl-ammonium hexafluorophosphate The title compound is prepared using an analogous procedure to Example 30 by replacing 3-phenylpropionic acid with (4-benzyloxy-phenyl)-acetic acid. $M^+$ 526.

Example 33

{2-[3-(4-Chloro-phenyl)-propionylamino]-ethyl}-{2-[(3,5-diamino-6-chloro-pyrazine-2-carbonyl)-amino]-ethyl}-dimethyl-ammonium hexafluorophosphate The title compound is prepared using an analogous procedure to Example 30 by replacing 3-phenylpropionic acid with 3-(4-chloro-phenyl)-propionic acid. $M^+$ 468.

Example 34

{2-[3-(4-Benzyloxy-phenyl)-propionylamino]-ethyl}-{2-[(3,5-diamino-6-chloro-pyrazine-2-carbonyl)-amino]-ethyl}-dimethyl-ammonium hexafluorophosphate The title compound is prepared using an analogous procedure to Example 30 by replacing 3-phenylpropionic acid with 3-(4-benzyloxy-phenyl)-propionic acid. $M^+$ 540.

Example 35

{2-[(3,5-Diamino-6-chloro-pyrazine-2-carbonyl)-amino]ethyl}-{2-[2-(6-methoxy-1,2,3,4-tetrahydro-naphthalen-1-yl)-acetylamino]-ethyl}-dimethyl-ammonium hexafluorophosphate The title compound is prepared using an analogous procedure to Example 30 by replacing 3-phenylpropionic acid with (6-methoxy-1,2,3,4-tetrahydro-naphthalen-1-yl)-acetic acid. $M^+$ 504.

Example 36

[2-(3-Benzo[1,3]dioxol-5-yl-propionylamino)-ethyl]-{2-[(3,5-diamino-6-chloro-pyrazine-2-carbonyl)-amino]-ethyl}-dimethyl-ammonium hexafluorophosphate The title compound is prepared using an analogous procedure to Example 30 by replacing 3-phenylpropionic acid with 3-Benzo[1,3]dioxol-5-yl-propionic acid. $M^+$ 478.

Example 37

{2-[(3,5-Diamino-6-chloro-pyrazine-2-carbonyl)-amino]-ethyl}-{2-[3-(4-methoxy-naphthalen-1-yl)-propionylamino]-ethyl}-dimethyl-ammonium hexafluorophosphate The title compound is prepared using an analogous procedure to Example 30 by replacing 3-phenylpropionic acid with 3-(4-methoxy-naphthalen-1-yl)-propionic acid. $M^+$ 514.

Example 38

{2-[(3,5-Diamino-6-chloro-pyrazine-2-carbonyl)-amino]-ethyl}-{2-[3-(4-fluoro-phenyl)-propionylamino]-ethyl}-dimethyl-ammonium hexafluorophosphate The title compound is prepared using an analogous procedure to Example 30 by replacing 3-phenylpropionic acid with 3-(4-fluoro-phenyl)-propionic acid. $M^+$ 452.

Example 39

{2-[2-(4-Chloro-phenyl)-acetylamino]-ethyl}-{2-[(3,5-diamino-6-chloro-pyrazine-2-carbonyl)-amino]-ethyl}-dimethyl-ammonium hexafluorophosphate The title compound is prepared using an analogous procedure to Example 30 by replacing 3-phenylpropionic acid with (4-chloro-phenyl)-acetic acid. $M^+$ 454.

Example 40

{2-[(3,5-Diamino-6-chloro-pyrazine-2-carbonyl)-amino]-ethyl}-{2-[3-(4-methoxy-phenyl)-propionylamino]-ethyl}-dimethyl-ammonium hexafluorophosphate The title compound is prepared using an analogous procedure to Example 30 by replacing 3-phenylpropionic acid with 3-(4-methoxy-phenyl)-propionic acid. $M^+$ 464.

Example 41

{2-[(3,5-Diamino-6-chloro-pyrazine-2-carbonyl)-amino]-ethyl}-{2-[4-(4-methoxy-phenyl)-butyrylamino]-ethyl}-dimethyl-ammonium hexafluorophosphate The title compound is prepared using an analogous procedure to Example 30 by replacing 3-phenylpropionic acid with 4-(4-methoxy-phenyl)-butyric acid. $M^+$ 478.

Example 42

{2-[(3,5-Diamino-6-chloro-pyrazine-2-carbonyl)-amino]-ethyl}-dimethyl-(2-phenylacetylamino-ethyl)-ammonium hexafluorophosphate The title compound is prepared using an analogous procedure to Example 30 by replacing 3-phenylpropionic acid with phenyl-acetic acid. $M^+$ 420.

Example 43

{2-[(3,5-Diamino-6-chloro-pyrazine-2-carbonyl)-amino]-ethyl}-dimethyl-[2-(2-p-tolyl-acetylamino)-ethyl]-ammonium hexafluorophosphate The title compound is prepared using an analogous procedure to Example 30 by replacing 3-phenylpropionic acid with p-tolyl-acetic acid. $M^+$ 434.

Example 44

[2-(4-Chloro-benzoylamino)-ethyl]-{2-[(3,5-diamino-6-chloro-pyrazine-2-carbonyl)-amino]-ethyl}-dimethyl-ammonium hexafluorophosphate The title compound is prepared using an analogous procedure to Example 30 by replacing 3-phenylpropionic acid with 4-chloro-benzoic acid. $M^+$ 440.

Example 45

(2-Benzoylamino-ethyl)-{2-[(3,5-diamino-6-chloro-pyrazine-2-carbonyl)-amino]-ethyl}-dimethyl-ammonium hexafluorophosphate The title compound is prepared using an analogous procedure to Example 30 by 3-phenylpropionic acid with benzoic acid. $M^+$ 406.

Example 46

{2-[(3,5-Diamino-6-chloro-pyrazine-2-carbonyl)-amino]-ethyl}-dimethyl-[2-(4-methyl-benzoylamino)-ethyl]-ammonium hexafluorophosphate The title compound is prepared using an analogous procedure to Example 30 by replacing 3-phenylpropionic acid with 4-methyl-benzoic acid. $M^+$ 420.

Example 47

{2-[(3,5-Diamino-6-chloro-pyrazine-2-carbonyl)-amino]-ethyl}-{2-[3-(3,4-dimethoxy-phenyl)-propionylamino]-ethyl}-dimethyl-ammonium hexafluorophosphate The title compound is prepared using an analogous procedure to Example 30 by replacing 3-phenylpropionic acid with 3-(3,4-dimethoxy-phenyl)-propionic acid. $M^+$ 494.

Example 48

{2-[(3,5-Diamino-6-chloro-pyrazine-2-carbonyl)-amino]-ethyl}-{2-[3-(4-methanesulfonyl-phenyl)-propionylamino]-ethyl}-dimethyl-ammonium hexafluorophosphate The title compound is prepared using an analogous procedure to Example 30 by replacing 3-phenylpropionic acid with 3-(4-methanesulfonyl-phenyl)-propionic acid. $M^+$ 512.

Example 49

{2-[(3,5-Diamino-6-chloro-pyrazine-2-carbonyl)-amino]-ethyl}-(2-{3-[3-(diaminomethylene-sulfamoyl)-4-methoxy-phenyl]-3-phenyl-propionylamino}-ethyl)-dimethyl-ammonium hexafluorophosphate The title compound is prepared using an analogous procedure to Example 30 by replacing 3-phenylpropionic acid with 3-[3-(Diaminomethylene-sulfamoyl)-4-methoxy-phenyl]-3-phenyl-propionic acid (Intermediate L). $M^+$ 661.

Example 50

{3-[2-(4-Benzyloxy-phenyl)-acetylamino]-propyl}-{2-[(3,5-diamino-6-chloro-pyrazine-2-carbonyl)-amino]-ethyl}-dimethyl-ammonium bromide A mixture of (3-amino-propyl)-{2-[(3,5-diamino-6-chloro-pyrazine-2-carbonyl)-amino]-ethyl}-dimethyl-ammonium bromide (Intermediate M) (1.0 g, 2.52 mmol), 4-benzyloxyphenylacetic acid (0.61 g, 2.52 mmol), N-methylmorpholine (1.0 mL, 9.10 mmol), N,N'-dicyclohexylcarbodiimide (0.52 g, 2.52 mmol) and 1-hydroxybenzotriazole (0.34 g, 2.52 mmol) in anhydrous DMF (20 mL) is stirred under a nitrogen atmosphere at RT for 16 h. The reaction mixture is concentrated under vacuum and is purified by column chromatography (basic alumina, 0-3% MeOH in DCM) to afford the title compound as a white solid. $M^+$ 540.
$^1$H NMR (400 MHz, DMSO-$d_6$) δ 8.23 (1H, t), 8.07 (1H, t), 7.52 (2H, br), 7.41-7.28 (5H, m), 7.16 (2H, d), 7.09 (2H, br), 6.91 (2H, d), 5.05 (2H, s), 3.58-3.3.51 (2H, m), 3.40-3.25 (6H, m), 3.11-3.03 (2H, m), 3.02 (6H, s), 1.87-1.75 (2H, m).

Example 51

{3-[2-(4-Chloro-phenyl)-acetylamino]-propyl}-{2-[(3,5-diamino-6-chloro-pyrazine-2-carbonyl)-amino]-ethyl}-dimethyl-ammonium hexafluorophosphate A mixture of (3-amino-propyl)-{2-[(3,5-diamino-6-chloro-pyrazine-2-carbonyl)-amino]-ethyl}-dimethyl-ammonium bromide (Intermediate M) (0.25 g, 0.63 mmol), (4-chloro-phenyl)-acetic acid (0.11 g, 0.64 mmol), N-methylmorpholine (0.25 mL, 2.27 mmol) and HATU (0.24 g, 0.63 mmol) in anhydrous DMF (8 mL) is stirred under a nitrogen atmosphere at RT for 16 h. The reaction mixture is concentrated in vacuo and is purified by column chromatography (basic alumina, 0-4% MeOH in DCM) to afford the title compound. $M^+$ 468. $^1$H NMR (400 MHz, DMSO-$d_6$) δ 8.22 (1H, t), 8.14 (1H, t), 7.45 (2H, br), 7.32 (2H, d), 7.24 (2H, d), 7.08 (2H, br), 3.57-3.51 (2H, m), 3.43 (2H, s), 3.42-3.25 (4H, m), 3.12-3.03 (2H, m), 3.02 (6H, s), 1.86-1.78 (2H, m).

Example 52

[3-(4-Chloro-benzoylamino)-propyl]-{2-[(3,5-diamino-6-chloro-pyrazine-2-carbonyl)-amino]-ethyl}-dimethyl-ammonium hexafluorophosphate The title compound is prepared using an analogous procedure to Example 51 by replacing (4-chloro-phenyl)-acetic acid with 4-chloro-benzoic acid. $M^+$ 454.

Example 53

{2-[(3,5-Diamino-6-chloro-pyrazine-2-carbonyl)-amino]-ethyl}-dimethyl-(3-phenylacetylamino-propyl)-ammonium hexafluorophosphate The title compound is prepared using an analogous procedure to Example 51 by replacing (4-chloro-phenyl)-acetic acid with phenyl acetic acid. $M^+$ 434.

Example 54

{2-[(3,5-Diamino-6-chloro-pyrazine-2-carbonyl)-amino]-ethyl}-dimethyl-[3-(2-p-tolyl-acetylamino)-propyl]-ammonium hexafluorophosphate The title compound is prepared using an analogous procedure to Example 51 by replacing (4-chloro-phenyl)-acetic acid with p-tolyl-acetic acid. $M^+$ 448.

Example 55

{2-[(3,5-Diamino-6-chloro-pyrazine-2-carbonyl)-amino]-ethyl}-dimethyl-[3-(3-phenyl-propionylamino)-propyl]-ammonium hexafluorophosphate The title compound is prepared using an analogous procedure to Example 51 by replacing (4-chloro-phenyl)-acetic acid with 3-phenyl-propionic acid. $M^+$ 448.

Example 56

{2-[(3,5-Diamino-6-chloro-pyrazine-2-carbonyl)-amino]-ethyl}-dimethyl-[3-(4-methyl-benzoylamino)-propyl]-ammonium hexafluorophosphate The title compound is prepared using an analogous procedure to Example 51 by replacing (4-chloro-phenyl)-acetic acid with 4-methyl-benzoic acid. $M^+$ 434.

Example 57

(3-Benzoylamino-propyl)-{2-[(3,5-diamino-6-chloro-pyrazine-2-carbonyl)-amino]-ethyl}-dimethyl-ammonium hexafluorophosphate The title compound is prepared using an analogous procedure to Example 51 by replacing (4-chloro-phenyl)-acetic acid with benzoic acid. $M^+$ 420

Example 58

{2-[(3,5-Diamino-6-chloro-pyrazine-2-carbonyl)-amino]-ethyl}-{3-[2-(4-fluoro-phenyl)-acetylamino]-propyl}-dimethyl-ammonium hexafluorophosphate The title compound is prepared using an analogous procedure to Example 51 by replacing (4-chloro-phenyl)-acetic acid with (4-fluoro-phenyl)-acetic acid. $M^+$ 452.

Example 59

{2-[(3,5-Diamino-6-chloro-pyrazine-2-carbonyl)-amino]-ethyl}-[3-(2-1H-indol-3-yl-acetylamino)-propyl]-dimethyl-ammonium hexafluorophosphate The title compound is prepared using an analogous procedure to Example 51 by replacing (4-chloro-phenyl)-acetic acid with (1H-indol-3-yl)-acetic acid. $M^+$ 473.

Example 60

{2-[(3,5-Diamino-6-chloro-pyrazine-2-carbonyl)-amino]-ethyl}-{3-[2-(4-methoxy-phenyl)-acetylamino]-propyl}-dimethyl-ammonium hexafluorophosphate The title compound is prepared using an analogous procedure to Example 51 by replacing (4-chloro-phenyl)-acetic acid with (4-methoxy-phenyl)-acetic acid. $M^+$ 464.

Example 61

{3-[3-(4-Chloro-phenyl)-propionylamino]-propyl}-{2-[(3,5-diamino-6-chloro-pyrazine-2-carbonyl)-amino]-ethyl}-dimethyl-ammonium hexafluorohosphate The title compound is prepared using an analogous procedure to Example 51 by replacing (4-chloro-phenyl)-acetic acid with 3-(4-chloro-phenyl)-propionic acid. $M^+$ 482.

Example 62

{2-[(3,5-Diamino-6-chloro-pyrazine-2-carbonyl)-amino]-ethyl}-dimethyl-[3-(3-p-tolyl-propionylamino)-propyl]-ammonium hexafluorophosphate The title compound is prepared using an analogous procedure to Example 51 by replacing (4-chloro-phenyl)-acetic acid with 3-p-tolyl-propionic acid. M⁺ 462.

Example 63

{4-[2-(4-Benzyloxy-phenyl)-acetylamino]-butyl}-{2-[(3,5-diamino-6-chloro-pyrazine-2-carbonyl)-amino]-ethyl}-dimethyl-ammonium bromide To a solution of 4-Benzyloxyphenyl acetic acid (0.013 g, 0.30 mmol) in DMF (1.5 mL) is added HATU (0.12 g, 0.3 mmol), N-methylmorpholine (0.13 mL, 1.2 mmol) and (4-amino-butyl)-{2-[(3,5-diamino-6-chloro-pyrazine-2-carbonyl)-amino]-ethyl}-dimethyl-ammonium bromide (Intermediate N) (0.1 g, 0.30 mmol). The solution is stirred at RT for 2 h. The solvent is removed in vacuo and the residue is purified by reverse phase chromatography (Isolute™ C18, 0-100% acetonitrile in water with 0.1% TFA) to yield the title compound. M⁺ 535. ¹H NMR (400 MHz, DMSO-d₆) δ 8.25 (1H, t), 8.05 (1H, t), 7.25 (2H, br), 7.42-7.32 (5H, m), 7.17 (2H, d), 7.09 (2H, br), 6.92 (2H, d), 5.06 (2H, s), 3.61-3.53 (2H, m), 3.39-3.33 (4H, m), 3.32 (2H, s), 3.10-3.03 (2H, m), 3.02 (6H, s), 1.61-1.49 (2H, m), 1.44-1.33 (2H, m).

Example 64

{4-[3-(4-Benzyloxy-phenyl)-propionylamino]-butyl}-{2-[(3,5-diamino-6-chloro-pyrazine-2-carbonyl)-amino]-ethyl}-dimethyl-ammonium hexafluorophosphate The title compound is prepared using an analogous procedure to Example 63 by replacing 4-benzyloxyphenylacetic acid with 3-(4-benzyloxy-phenyl)-propionic acid. M⁺ 568.

Example 65

{4-[3-(4-Chloro-phenyl)-propionylamino]-butyl}-{2-[(3,5-diamino-6-chloro-pyrazine-2-carbonyl)-amino]-ethyl}-dimethyl-ammonium hexafluorophosphate The title compound is prepared using an analogous procedure to Example 63 by replacing 4-benzyloxyphenylacetic acid with 3-(4-chloro-phenyl)-propionic acid. M⁺ 496.

Example 66

{2-[(3,5-Diamino-6-chloro-pyrazine-2-carbonyl)-amino]-ethyl}-dimethyl-[4-(3-p-tolyl-propionylamino)-butyl]-ammonium hexafluorophosphate The title compound is prepared using an analogous procedure to Example 63 by replacing 4-benzyloxyphenylacetic acid with 3-para-tolyl-propionic acid. M⁺ 476.

Example 67

{4-[2-(4-Chloro-phenyl)-acetylamino]-butyl}-{2-[(3,5-diamino-6-chloro-pyrazine-2-carbonyl)-amino]-ethyl}-dimethyl-ammonium hexafluorophosphate The title compound is prepared using an analogous procedure to Example 63 by replacing 4-benzyloxyphenylacetic acid with (4-chloro-phenyl)-acetic acid. M⁺ 482.

Example 68

{2-[(3,5-Diamino-6-chloro-pyrazine-2-carbonyl)-amino]-ethyl}-dimethyl-[4-(2-p-tolyl-acetylamino)-butyl]-ammonium hexafluorophosphate The title compound is prepared using an analogous procedure to Example 63 by replacing 4-benzyloxyphenylacetic acid with para-tolyl-acetic acid. M⁺ 463.

Example 69

{2-[(3,5-Diamino-6-chloro-pyrazine-2-carbonyl)-amino]-ethyl}-dimethyl-[4-(3-phenyl-propionylamino)-butyl]-ammonium hexafluorophosphate The title compound is prepared using an analogous procedure to Example 63 by replacing 4-benzyloxyphenylacetic acid with 3-phenyl-propionic acid. M⁺ 462

Example 70

{2-[(3,5-Diamino-6-chloro-pyrazine-2-carbonyl)-amino]-ethyl}-{4-[2-(4-hydroxy-phenyl)-acetylamino]-butyl}-dimethyl-ammonium trifluoroacetate The title compound is prepared using an analogous procedure to Example 63 by replacing 4-benzyloxyphenylacetic acid with (4-hydroxy-phenyl)-acetic acid. M⁺ 464.

Example 71

{2-[(3,5-Diamino-6-chloro-pyrazine-2-carbonyl)-amino]-ethyl}-[4-(2-1H-indol-3-yl-acetylamino)-butyl]-dimethyl-ammonium hexafluorophosphate The title compound is prepared using an analogous procedure to Example 63 by replacing 4-benzyloxyphenylacetic acid with (1H-indol-3-yl)-acetic acid. M⁺ 487.

Example 72

{2-[(3,5-Diamino-6-chloro-pyrazine-2-carbonyl)-amino]-ethyl}-{4-[3-(4-methoxy-phenyl)-propionylamino]-butyl}-dimethyl-ammonium hexafluorophosphate The title compound is prepared using an analogous procedure to Example 63 by replacing 4-benzyloxyphenylacetic acid with 3-(4-methoxy-phenyl)-propionic acid. M⁺ 492.

Example 73

[4-(4-Chloro-benzoylamino)-butyl]-{2-[(3,5-di-amino-6-chloro-pyrazine-2-carbonyl)-amino]-ethyl}-dimethyl-ammonium hexafluorophosphate The title compound is prepared using an analogous procedure to Example 63 by replacing 4-benzyloxyphenylacetic acid with 4-chloro-benzoic acid. M$^+$ 468.

Example 74

{2-[(3,5-Diamino-6-chloro-pyrazine-2-carbonyl)-amino]-ethyl}-dimethyl-(4-phenylacetylamino-butyl)-ammonium hexafluorophosphate The title compound is prepared using an analogous procedure to Example 63 by replacing 4-benzyloxyphenylacetic acid with phenyl-acetic acid. M$^+$ 448.

Example 75

{2-[(3,5-Diamino-6-chloro-pyrazine-2-carbonyl)-amino]-ethyl}-dimethyl-[4-(4-methyl-benzoylamino)-butyl]-ammonium hexafluorophosphate The title compound is prepared using an analogous procedure to Example 63 by replacing 4-benzyloxyphenylacetic acid with 4-methyl-benzoic acid. M$^+$ 448.

Example 76

{2-[(3,5-Diamino-6-chloro-pyrazine-2-carbonyl)-amino]-ethyl}-{4-[2-(4-methoxy-phenyl)-acetylamino]-butyl}-dimethyl-ammonium hexafluorophosphate The title compound is prepared using an analogous procedure to Example 63 by replacing 4-benzyloxyphenylacetic acid with (4-methoxy-phenyl)-acetic acid. M$^+$ 478.

Example 77

(4-Benzoylamino-butyl)-{2-[(3,5-diamino-6-chloro-pyrazine-2-carbonyl)-amino]-ethyl}-dimethyl-ammonium hexafluorophosphate The title compound is prepared using an analogous procedure to Example 63 by replacing 4-benzyloxyphenylacetic acid with benzoic acid. M$^+$ 434.

Example 78

{5-[2-(4-Benzyloxy-phenyl)-acetylamino]-pentyl}-{2-[(3,5-diamino-6-chloro-pyrazine-2-carbonyl)-amino]-ethyl}-dimethyl-ammonium bromide A solution of (5-amino-pentyl)-{2-[(3,5-diamino-6-chloro-pyrazine-2-carbonyl)-amino]-ethyl}-dimethyl-ammonium bromide (Intermediate O) (1.0 g, 2.35 mmol), 4-benzyloxy phenyl acetic acid (0.57 g, 2.35 mmol), N-methylmorpholine (1.0 mL, 9.09 mmol), DCC (0.49 g, 2.35 mmol) and HOBt (0.32 g, 2.36 mmol) in DMF (20 mL) is stirred at RT for 1 h. The reaction mixture is concentrated in vacuo, and the residue is purified by column chromatography (basic alumina, 0-4% methanol in DCM) to afford a brown solid which is crystallised from methanol and EtOAc to afford the title compound. M$^+$ 568.

Example 79

{5-[3-(4-Benzyloxy-phenyl)-propionylamino]-pentyl}-{2-[(3,5-diamino-6-chloro-pyrazine-2-carbonyl)-amino]-ethyl}-dimethyl-ammonium hexafluorophosphate The title compound is prepared using an analogous procedure to Example 78 by replacing 4-benzyloxyphenylacetic acid with 3-(4-benzyloxy-phenyl)-propionic acid. M$^+$ 582.

Example 80

{5-[3-(4-Chloro-phenyl)-propionylamino]-pentyl}-{2-[(3,5-diamino-6-chloro-pyrazine-2-carbonyl)-amino]-ethyl}-dimethyl-ammonium hexafluorophosphate The title compound is prepared using an analogous procedure to Example 78 by replacing 4-benzyloxyphenylacetic acid with 3-(4-chloro-phenyl)-propionic acid. M$^+$ 510.

Example 81

[5-(4-Chloro-benzoylamino)-pentyl]-{2-[(3,5-di-amino-6-chloro-pyrazine-2-carbonyl)-amino]-ethyl}-dimethyl-ammonium hexafluorophosphate The title compound is prepared using an analogous procedure to Example 78 by replacing 4-benzyloxyphenylacetic acid with 4-chloro-benzoic acid. M$^+$ 482.

Example 82

{2-[(3,5-Diamino-6-chloro-pyrazine-2-carbonyl)-amino]-ethyl}-{5-[4-(4-methoxy-phenyl)-butyrylamino]-pentyl}-dimethyl-ammonium hexafluorophosphate The title compound is prepared using an analogous procedure to Example 78 by replacing 4-benzyloxyphenylacetic acid with 4-(4-methoxy-phenyl)-butyric acid. M$^+$ 520.

Example 83

{2-[(3,5-Diamino-6-chloro-pyrazine-2-carbonyl)-amino]-ethyl}-dimethyl-[5-(3-p-tolyl-propionylamino)-pentyl]-ammonium hexafluorophosphate The title compound is prepared using an analogous procedure to Example 78 by replacing 4-benzyloxyphenylacetic acid with 3-p-tolyl-propionic acid. M$^+$ 490.

Example 84

{2-[(3,5-Diamino-6-chloro-pyrazine-2-carbonyl)-amino]-ethyl}-{5-[3-(4-methoxy-phenyl)-propionylamino]-pentyl}-dimethyl-ammonium hexafluorophosphate The title compound is prepared using an analogous procedure to Example 78 by replacing 4-benzyloxyphenylacetic acid with 3-(4-methoxy-phenyl)-propionic acid. M$^+$ 506.

Example 85

{5-[2-(4-Chloro-phenyl)-acetylamino]-pentyl}-{2-[(3,5-diamino-6-chloro-pyrazine-2-carbonyl)-amino]-ethyl}-dimethyl-ammonium hexafluorophosphate The title compound is prepared using an analogous procedure to Example 78 by replacing 4-benzyloxyphenylacetic acid with (4-chloro-phenyl)-acetic acid. $M^+$ 496.

Example 86

{2-[(3,5-Diamino-6-chloro-pyrazine-2-carbonyl)-amino]-ethyl}-dimethyl-[5-(2-p-tolyl-acetylamino)-pentyl]-ammonium hexafluorophosphate The title compound is prepared using an analogous procedure to Example 78 by replacing 4-benzyloxyphenylacetic acid with p-tolyl-acetic acid. $M^+$ 476.

Example 87

{2-[(3,5-Diamino-6-chloro-pyrazine-2-carbonyl)-amino]-ethyl}-dimethyl-[5-(4-methyl-benzoylamino)-pentyl]-ammonium hexafluorophosphate The title compound is prepared using an analogous procedure to Example 78 by replacing 4-benzyloxyphenylacetic acid with 4-methyl-benzoic acid. $M^+$ 462.

Example 88

{2-[(3,5-Diamino-6-chloro-pyrazine-2-carbonyl)-amino]-ethyl}-dimethyl-[5-(3-phenyl-propionylamino)-pentyl]-ammonium hexafluorophosphate The title compound is prepared using an analogous procedure to Example 78 by replacing 4-benzyloxyphenylacetic acid with 3-phenyl-propionic acid. $M^+$ 476.

Example 89

{2-[(3,5-Diamino-6-chloro-pyrazine-2-carbonyl)-amino]-ethyl}-dimethyl-(5-phenylacetylamino-pentyl)-ammonium hexafluorophosphate The title compound is prepared using an analogous procedure to Example 78 by replacing 4-benzyloxyphenylacetic acid with phenyl-acetic acid. $M^+$ 462.

Example 90

{2-[(3,5-Diamino-6-chloro-pyrazine-2-carbonyl)-amino]-ethyl}-{5-[2-(2,4-dimethoxy-phenyl)-acetylamino]-pentyl}-dimethyl-ammonium hexafluorophosphate The title compound is prepared using an analogous procedure to Example 78 by replacing 4-benzyloxyphenylacetic acid with (2,4-dimethoxy-phenyl)-acetic acid. $M^+$ 522.

Example 91

(5-Benzoylamino-pentyl)-{2-[(3,5-diamino-6-chloro-pyrazine-2-carbonyl)-amino]-ethyl}-dimethyl-ammonium hexafluorophosphate The title compound is prepared using an analogous procedure to Example 78 by replacing 4-benzyloxyphenylacetic acid with benzoic acid. $M^+$ 448.

Example 92

{2-[(3,5-Diamino-6-chloro-pyrazine-2-carbonyl)-amino]-ethyl}-{5-[2-(3,4-dimethoxy-phenyl)-acetylamino]-pentyl}-dimethyl-ammonium hexafluorophosphate The title compound is prepared using an analogous procedure to Example 78 by replacing 4-benzyloxyphenylacetic acid with (3,4-dimethoxy-phenyl)-acetic acid. $M^+$ 522.

Example 93

{2-[(3,5-Diamino-6-chloro-pyrazine-2-carbonyl)-amino]-ethyl}-{5-[3-(3,4-dimethoxy-phenyl)-propionylamino]-pentyl}-dimethyl-ammonium hexafluorophosphate The title compound is prepared using an analogous procedure to Example 78 by replacing 4-benzyloxyphenylacetic acid with 3-(3,4-dimethoxy-phenyl)-propionic acid. $M^+$ 536.

Example 94

[5-(4-Chloro-benzenesulfonylamino)-pentyl]-{2-[(3,5-diamino-6-chloro-pyrazine-2-carbonyl)-amino]-ethyl}-dimethyl-ammonium bromide A mixture of (5-amino-pentyl)-{2-[(3,5-diamino-6-chloro-pyrazine-2-carbonyl)-amino]-ethyl}-dimethyl-ammonium bromide (Intermediate O) (0.25 g, 0.59 mmol), 4-chlorobenzenesulfonyl chloride (0.13 g, 0.59 mmol) and N-methylmorpholine (0.30 mL, 2.73 mmol) in DMF (5 mL) is stirred at RT for 16 h. The reaction mixture is concentrated in vacuo and is purified by column chromatography (basic alumina, 0-10% MeOH in DCM). The solid that is obtained is dissolved in a minimum amount of MeOH and DCM then precipitated by the addition of diethyl ether. The supernatant solvent mixture is decanted and the product is washed again with diethyl ether then dried under vacuum to give the title compound. $M^+$ 578. $^1$H NMR (400 MHz, DMSO-$d_6$) δ 8.25 (1H, t), 7.78 (2H, d), 7.74 (1H, t), 7.57 (2H, br), 7.67 (2H, d), 7.11 (2H, br), 3.56 (2H, q), 3.36 (2H, t), 3.28-3.22 (2H, m), 3.04 (6H, s), 2.95 (2H, q), 1.65-1.58 (2H, m), 1.37 (2H, quintet), 1.24-1.16 (2H, m).

Example 95

[5-(4-Chloro-phenylmethanesulfonylamino)-pentyl]-{2-[(3,5-diamino-6-chloro-pyrazine-2-carbonyl)-amino]-ethyl}-dimethyl-ammonium bromide The title compound is prepared using an analogous procedure to Example 94 by replacing 4-chlorobenzenesulfonyl chloride with (4-chloro-phenyl)-methanesulfonyl chloride. $M^+$ 533.

Example 96

{2-[(3,5-Diamino-6-chloro-pyrazine-2-carbonyl)-amino]-ethyl}-dimethyl-(5-p-tolylmethanesulfonylamino-pentyl)-ammonium bromide The title compound is prepared using an analogous procedure to Example 94 by replacing 4-chlorobenzenesulfonyl chloride with p-tolyl-methanesulfonyl chloride. $M^+$ 512.

Example 97

{2-[(3,5-Diamino-6-chloro-pyrazine-2-carbonyl)-amino]-ethyl}-dimethyl-[5-(toluene-4-sulfonylamino)-pentyl]-ammonium bromide The title compound is prepared using an analogous procedure to Example 94 by replacing 4-chlorobenzenesulfonyl chloride with 4-methyl-benzenesulfonyl chloride. $M^+$ 498.

Example 98

{2-[(3,5-Diamino-6-chloro-pyrazine-2-carbonyl)-amino]-ethyl}-dimethyl-(5-phenylmethanesulfonylamino-pentyl)-ammonium bromide The title compound is prepared using an analogous procedure to Example 94 by replacing 4-chlorobenzenesulfonyl chloride with phenyl-methanesulfonyl chloride. $M^+$ 498.

Example 99

(5-Benzenesulfonylamino-pentyl)-{2-[(3,5-diamino-6-chloro-pyrazine-2-carbonyl)-amino]-ethyl}-dimethyl-ammonium bromide The title compound is prepared using an analogous procedure to Example 94 by replacing 4-chlorobenzenesulfonyl chloride with benzenesulfonyl chloride. $M^+$ 484.

Example 100

[4-(4-Chloro-benzenesulfonylamino)-butyl]-{2-[(3,5-diamino-6-chloro-pyrazine-2-carbonyl)-amino]-ethyl}-dimethyl-ammonium bromide A solution of (4-amino-butyl)-{2-[(3,5-diamino-6-chloro-pyrazine-2-carbonyl)-amino]-ethyl}-dimethyl-ammonium bromide (Intermediate N) (0.25 g, 0.60 mmol), 4-chlorobenzenesulfonyl chloride (0.125 g, 0.59 mmol) and N-methylmorpholine (0.3 mL, 2.73 mmol) in DMF (5 mL) is shaken at RT for 16 h. The reaction mixture is concentrated in vacuo, and the residue is purified by chromatography (basic alumina, 0-15% methanol in DCM) to obtain the title compound. $M^+$ 504.

Example 101

{2-[(3,5-Diamino-6-chloro-pyrazine-2-carbonyl)-amino]-ethyl}-dimethyl-[4-(toluene-4-sulfonylamino)-butyl]-ammonium bromide The title compound is prepared using an analogous procedure to Example 100 by replacing 4-chlorobenzenesulfonyl chloride with 4-methyl-benzenesulfonyl chloride. $M^+$ 484

Example 102

[4-(4-Chloro-phenylmethanesulfonylamino)-butyl]-{2-[(3,5-diamino-6-chloro-pyrazine-2-carbonyl)-amino]-ethyl}-dimethyl-ammonium bromide The title compound is prepared using an analogous procedure to Example 100 by replacing 4-chlorobenzenesulfonyl chloride with (4-chloro-phenyl)-methanesulfonyl chloride. $M^+$ 518.

Example 103

{2-[(3,5-Diamino-6-chloro-pyrazine-2-carbonyl)-amino]-ethyl}-dimethyl-(4-phenylmethanesulfonylamino-butyl)-ammonium bromide The title compound is prepared using an analogous procedure to Example 100 by replacing 4-chlorobenzenesulfonyl chloride with phenyl-methanesulfonyl chloride. $M^+$ 484.

Example 104

{2-[(3,5-Diamino-6-chloro-pyrazine-2-carbonyl)-amino]-ethyl}-dimethyl-(4-p-tolylmethanesulfonylamino-butyl)-ammonium bromide The title compound is prepared using an analogous procedure to Example 100 by replacing 4-chlorobenzenesulfonyl chloride with p-tolyl-methanesulfonyl chloride. $M^+$ 498.

Example 105

(4-Benzenesulfonylamino-butyl)-{2-[(3,5-diamino-6-chloro-pyrazine-2-carbonyl)-amino]-ethyl}-dimethyl-ammonium bromide The title compound is prepared using an analogous procedure to Example 100 by replacing 4-chlorobenzenesulfonyl chloride with benzenesulfonyl chloride. $M^+$ 470.

Example 106

{2-[(3,5-Diamino-6-chloro-pyrazine-2-carbonyl)-amino]-ethyl}-[4-(2,4-dimethoxy-benzenesulfonylamino)-butyl]-dimethyl-ammonium trifluoroacetate The title compound is prepared using an analogous procedure to Example 100 by replacing 4-chlorobenzenesulfonyl chloride with 2,4-dimethoxy-benzenesulfonyl chloride. $M^+$ 530.

Example 107

{4-[4-(2-Cyano-ethoxy)-benzenesulfonylamino]-butyl}-{2-[(3,5-diamino-6-chloro-pyrazine-2-carbonyl)-amino]-ethyl}-dimethyl-ammonium trifluoroacetate The title compound is prepared using an analogous procedure to Example 100 by replacing 4-chlorobenzenesulfonyl chloride with 4-(2-cyano-ethoxy)-benzenesulfonyl chloride. $M^+$ 539.

Example 108

[2-(4-Chloro-phenylmethanesulfonylamino)-ethyl]-{2-[(3,5-diamino-6-chloro-pyrazine-2-carbonyl)-amino]-ethyl}-dimethyl-ammonium bromide A solution of (2-amino-ethyl)-{2-[(3,5-diamino-6-chloro-pyrazine-2-carbonyl)-amino]-ethyl}-dimethyl-ammonium bromide (Intermediate K) (0.3 g, 0.78 mmol), (4-chloro-phenyl)-methanesulfonyl chloride (0.18 g, 0.78 mmol) and N-methylmorpholine (0.35 mL, 3.18 mmol) in DMF (5 mL) is shaken at RT for 16 h. After this time the solvent is removed in vacuo and the residue is subjected to chromatography (basic alumina, 0-15% methanol in DCM) to yield the title compound. $M^+$ 490.

Example 109

{2-[(3,5-Diamino-6-chloro-pyrazine-2-carbonyl)-amino]-ethyl}-dimethyl-(2-p-tolylmethanesulfonylamino-ethyl)-ammonium bromide The title compound is prepared using an analogous procedure to Example 108 by replacing (4-chloro-phenyl)-methanesulfonyl chloride with p-tolyl-methanesulfonyl chloride. $M^+$ 470.

Example 110

{2-[(3,5-Diamino-6-chloro-pyrazine-2-carbonyl)-amino]-ethyl}-dimethyl-[2-(toluene-4-sulfonylamino)-ethyl]-ammonium bromide The title compound is prepared using an analogous procedure to Example 108 by replacing (4-chloro-phenyl)-methanesulfonyl chloride with 4-methyl-benzenesulfonyl chloride. $M^+$ 456.

Example 111

[2-(4-Chloro-benzenesulfonylamino)-ethyl]-{2-[(3,5-diamino-6-chloro-pyrazine-2-carbonyl)-amino]-ethyl}-dimethyl-ammonium bromide The title compound is prepared using an analogous procedure to Example 108 by replacing (4-chloro-phenyl)-methanesulfonyl chloride with 4-chloro-benzenesulfonyl chloride. $M^+$ 476.

Example 112

{2-[(3,5-Diamino-6-chloro-pyrazine-2-carbonyl)-amino]-ethyl}-dimethyl-(2-phenylmethanesulfonylamino-ethyl)-ammonium bromide The title compound is prepared using an analogous procedure to Example 108 by replacing (4-chloro-phenyl)-methanesulfonyl chloride with phenyl-methanesulfonyl chloride. $M^+$ 456.

Example 113

(2-Benzenesulfonylamino-ethyl)-{2-[(3,5-diamino-6-chloro-pyrazine-2-carbonyl)-amino]-ethyl}-dimethyl-ammonium bromide The title compound is prepared using an analogous procedure to Example 108 by replacing (4-chloro-phenyl)-methanesulfonyl chloride with benzenesulfonyl chloride. $M^+$ 442.

Example 114

{2-[(3,5-Diamino-6-chloro-pyrazine-2-carbonyl)-amino]-ethyl}-dimethyl-(3-p-tolylmethanesulfonylamino-propyl)-ammonium bromide A solution of (3-amino-propyl)-{2-[(3,5-diamino-6-chloro-pyrazine-2-carbonyl)-amino]-ethyl}-dimethyl-ammonium bromide (Intermediate M) (0.30 g, 0.756 mmol), p-tolyl-methanesulfonyl chloride (0.16 g, 0.76 mmol) and N-methylmorpholine (0.4 mL, 3.64 mmol) in DMF (5 mL) is shaken at RT for 16 h. The solvent is removed in vacuo and the residue is subjected to chromatography (basic alumina; 0-15% methanol in DCM) to yield the title compound. $M^+$ 484.

Example 115

[3-(4-Chloro-phenylmethanesulfonylamino)-propyl]-{2-[(3,5-diamino-6-chloro-pyrazine-2-carbonyl)-amino]-ethyl}-dimethyl-ammonium bromide The title compound is prepared using an analogous procedure to Example 114 replacing p-tolyl-methanesulfonyl chloride with (4-chloro-phenyl)-methanesulfonyl chloride. $M^+$ 504.

Example 116

[3-(4-Chloro-benzenesulfonylamino)-propyl]-{2-[(3,5-diamino-6-chloro-pyrazine-2-carbonyl)-amino]-ethyl}-dimethyl-ammonium bromide The title compound is prepared using an analogous procedure to Example 114 replacing p-tolyl-methanesulfonyl chloride with 4-chloro-benzenesulfonyl chloride. $M^+$ 490.

Example 117

{2-[(3,5-Diamino-6-chloro-pyrazine-2-carbonyl)-amino]-ethyl}-dimethyl-(3-phenylmethanesulfonylamino-propyl)-ammonium bromide The title compound is prepared using an analogous procedure to Example 114 replacing p-tolyl-methanesulfonyl chloride with phenyl-methanesulfonyl chloride. $M^+$ 470.

Example 118

{2-[(3,5-Diamino-6-chloro-pyrazine-2-carbonyl)-amino]-ethyl}-dimethyl-[3-(toluene-4-sulfonylamino)-propyl]-ammonium bromide The title compound is prepared using an analogous procedure to Example 114 replacing p-tolyl-methanesulfonyl chloride with 4-methyl-benzenesulfonyl chloride. $M^+$ 470.

Example 119

(3-Benzenesulfonylamino-propyl)-{2-[(3,5-diamino-6-chloro-pyrazine-2-carbonyl)-amino]-ethyl}-dimethyl-ammonium bromide The title compound is prepared using an analogous procedure to Example 114 replacing p-tolyl-methanesulfonyl chloride with benzenesulfonyl chloride. $M^+$ 456.

Example 120

((S)-1-{[(3,5-Diamino-6-chloro-pyrazine-2-carbonyl)-amino]-methyl}-butyl)-[3-(4-methoxy-phenyl)-propyl]-dimethyl-ammonium trifluoroacetate Step 1: [(S)-1-(1,3-Dioxo-1,3-dihydro-isoindol-2-ylmethyl)-butyl]-carbamic acid tert-butyl ester To a mixture of phthalimide (1.43 g, 9.72 mmol), ((S)-1-hydroxymethyl-butyl)-carbamic acid tert-butyl ester (prepared according to the procedure described in US 2007/0032433 page 232) (1.97 g, 9.69 mmol) and triphenylphosphine (2.55 g, 9.72 mmol) in DCM (25 mL) at 0° C. is added DEAD (1.6 mL, 10.2 mmol) dropwise. The reaction mixture is stirred at RT overnight. The reaction mixture is adsorbed onto silica gel and purification by chromatograghy (SiO$_2$, 0-15% EtOAc in iso-hexane) affords the title compound as white solid. [M+H]$^+$ 233.

Step 2: ((S)-1-Aminomethyl-butyl)-carbamic acid tert-butyl ester

A mixture of [(S)-1-(1,3-dioxo-1,3-dihydro-isoindol-2-ylmethyl)-butyl]-carbamic acid tert-butyl ester (2.80 g, 8.42 mmol) and hydrazine monohydrate (3.0 mL, 60.0 mmol) in EtOH (50 mL) and DCM (75 mL) is stirred at RT for 48 h. The precipitated solid is collected by filtration and washed with DCM to afford the crude product as a white solid that is used without further purification.

Step 3: ((5)-1-{[(3,5-Diamino-6-chloro-pyrazine-2-carbonyl)-amino]-methyl}-butyl)-carbamic acid tert-butyl ester A mixture of ((S)-1-aminomethyl-butyl)-carbamic acid tert-butyl ester (1.70 g, 8.40 mmol), 3,5-diamino-6-chloro-pyrazine-2-carboxylic acid (1.59 g, 8.43 mmol), N-methyl-morpholine (3.8 mL, 34.5 mmol) and HATU (3.2 g, 8.42 mmol) in anhydrous DMF (50 mL) is stirred at RT for 16 h. The reaction mixture is concentrated in vacuo and the resulting residue is purified by column chromatography (basic alumina, MeOH:DCM) to afford the title compound as yellow solid. [M+H]$^+$ 333.

Step 4: 3,5-Diamino-6-chloro-pyrazine-2-carboxylic acid ((S)-2-amino-pentyl)-amide hydrochloride To a solution of ((S)-1-{[(3,5-diamino-6-chloro-pyrazine-2-carbonyl)-amino]-methyl}-butyl)-carbamic acid tert-butyl ester (1.30 g, 3.49 mmol) in 1,4-dioxane (20 mL) is added HCl (50 mL of a 4 M solution in 1,4-dioxane, 200 mmol) and the reaction mixture is stirred at RT for 16 h. The reaction mixture is concentrated in vacuo and the yellow solid obtained is triturated with diethyl ether; the diethyl ether layer is decanted and the product is dissolved in a minimal volume of MeOH and is precipitated by the addition of diethyl ether. The solvent is decanted and the resulting solid is dried under vacuum to afford the title compound.

Step 5: 3,5-Diamino-6-chloro-pyrazine-2-carboxylic acid {(S)-2-[3-(4-methoxy-phenyl)-propylamino]-pentyl}-amide hydrochloride 3,5-Diamino-6-chloro-pyrazine-2-carboxylic acid ((S)-2-amino-pentyl)-amide hydrochloride (400 mg, 1.467 mmol), 3-(4-methoxyphenyl)propionaldehyde (181 mg, 1.103 mmol) and sodium triacetoxyborohydride (467 mg, 2.205 mmol) are dissolved in DCM (150 mL). The reaction mixture is stirred at reflux overnight. To the reaction mixture is added 1 M NaOH solution (50 mL) and DCM (50 mL). The organic phase is separated and the aqueous phase is extracted once with DCM. The combined organic phases are washed with brine, dried (MgSO$_4$), filtered and concentrated in vacuo to afford a yellow solid. Purification by flash column chromatography (SiO$_2$, MeOH:DCM, gradient 2-10%+0.1% TEA) affords the title compound. [M+H]$^+$ 421.

Step 6: ((S)-1-{[(3,5-Diamino-6-chloro-pyrazine-2-carbonyl)-amino]-methyl}-butyl)-[3-(4-methoxy-phenyl)-propyl]-dimethyl-ammonium trifluoroacetate 3,5-Diamino-6-chloro-pyrazine-2-carboxylic acid {(S)-2-[3-(4-methoxy-phenyl)-propylamino]-pentyl}-amide hydrochloride (500 mg, 0.935 mmol) is dissolved in butan-2-one (50 mL). Potassium carbonate (646 mg, 4.67 mmol) and MeI (0.234 ml, 3.74 mmol) are added and the reaction mixture is stirred at 80° C. overnight. Further MeI (0.234 ml, 3.74 mmol) is added and reaction is heated at 80° C. for 24 h. The reaction mixture is filtered through Celite™ washing with MeOH and the filterate concentrated. Purification by reverse phase chromatography (Isolute™ C18, 0-100% acetonitrile in water with 0.1% TFA) yields the title compound. M$^+$ 449. $^1$H NMR (400 MHz, DMSO-d$_6$) δ 8.39 (1H, t), 7.11 (2H, br), 7.01 (2H, d), 6.79 (2H, d), 5.76 (2H, br), 3.70 (3H, s), 3.59-3.41 (2H, m), 3.37-3.29 (1H, m), 3.04 (3H, s), 3.01 (3H, s), 2.55-2.34 (4H, m), 1.97-1.72 (3H, m), 1.61-1.36 (3H, m), 0.91 (3H, t).

Example 121

((S)-1-{[(3,5-Diamino-6-chloro-pyrazine-2-carbonyl)-amino]-methyl}-butyl)-[3-(4-hydroxy-phenyl)-propyl]-dimethyl-ammonium trifluoroacetate To a solution of ((S)-1-{[(3,5-diamino-6-chloro-pyrazine-2-carbonyl)-amino]-methyl}-butyl)-[3-(4-methoxy-phenyl)-propyl]-dimethyl-ammonium trifluoroacetate (Example 120) (313 mg, 0.556 mmol) in DCM (100 mL) is added BBr$_3$ (3.34 mL of a 1M solution in heptane, 3.34 mmol). The reaction mixture is stirred at RT overnight. The reaction mixture is quenched cautiously by the addition of water then the organic solvents are removed in vacuo. Purification by reverse phase column chromatography (Isolute™ C18, 0-50% acetonitrile in water with 0.1% TFA) affords the title compound. M$^+$ 435. $^1$H NMR (400 MHz, DMSO-d$_6$) δ 8.40 (1H, t), 7.13 (2H, br), 6.89 (2H, d), 6.64 (2H, d), 5.29 (3H, br), 3.79-3.68 (1H, m), 3.57-3.43 (3H, m), 3.37-3.25 (1H, m), 3.04 (3H, s), 3.01 (3H, s), 2.41-2.30 (2H, m), 1.95-1.73 (3H, m), 1.64-1.35 (3H, m), 0.92 (3H, t).

Example 122

{2-[(3,5-Diamino-6-chloro-pyrazine-2-carbonyl)-amino]-ethyl}-bis-[3-(4-hydroxy-phenyl)-propyl]-methyl-ammonium trifluoroacetate The title compound is prepared using an analogous procedure to Example 121 by replacing ((S)-1-{[(3,5-diamino-6-chloro-pyrazine-2-carbonyl)-amino]-methyl}-butyl)-[3-(4-methoxy-phenyl)-propyl]-dimethyl-ammonium trifluoroacetate (Example 120) with {2-[(3,5-diamino-6- chloro-pyrazine-2-carbonyl)-amino]-ethyl}-bis-[3-(4-methoxy-phenyl)-propyl]-methyl-ammonium trifluoroacetate (Example 20). M⁺ 513.

Example 123

{2-[(3,5-Diamino-6-chloro-pyrazine-2-carbonyl)-amino]-ethyl}-[3-(4-hydroxy-phenyl)-propyl]-dimethyl-ammonium bromide The title compound is prepared using an analogous procedure to Example 121 by replacing ((S)-1-{[(3,5-diamino-6-chloro-pyrazine-2-carbonyl)-amino]-methyl}-butyl)-[3-(4-methoxy-phenyl)-propyl]-dimethyl-ammonium trifluoroacetate (Example 120) with {2-[(3,5-diamino-6-chloro-pyrazine-2-carbonyl)-amino]-ethyl}-[3-(4-methoxy-phenyl)-propyl]-dimethyl-ammonium bromide (Example 27). M⁺ 393.

Example 124

((S)-1-{[(3,5-Diamino-6-chloro-pyrazine-2-carbonyl)-amino]-methyl}-butyl)-{3-[4-((S)-2,3-dihydroxy-propoxy)-phenyl]-propyl}-dimethyl-ammonium trifluoroacetate Triethylamine (63.5 μL, 0.46 μmol) is added to a solution of ((S)-1-{[(3,5-Diamino-6-chloro-pyrazine-2-carbonyl)-amino]-methyl}-butyl)-[3-(4-hydroxy-phenyl)-propyl]-dimethyl-ammonium trifluoroacetate (Example 121)(50 mg, 0.091 mmol) in EtOH (5 mL) and the solution is heated to reflux. Once at reflux (S)-glycidol (6.04 μL, 0.091 mmol) is added and the reaction is heated at reflux overnight. Two further portions of (S)-glycidol (2×6.04 μl, 2×0.091 mmol) are added and the reaction is heated at reflux for 24 h. The reaction mixture is concentrated in vacuo and purification by reverse phase chromatography (Isolute™ C18, 0-30% acetonitrile in water with 0.1% TFA) affords the title compound. M⁺ 509. ¹H NMR (400 MHz, DMSO-d₆) δ 8.39 (1H, t), 8.20-7.18 (2H, br), 7.24-6.98 (2H, br), 6.99 (2H, d), 6.79 (2H, d), 5.70-3.98 (2H, br), 3.93-3.89 (1H, m), 3.85-3.67 (3H, m), 3.60-3.43 (3H, m), 3.42 (2H, d), 3.39-3.28 (1H, m), 3.04 (3H, s), 3.01 (3H, s), 2.48-2.32 (2H, m), 2.00-1.71 (3H, m), 1.61-1.37 (3H, m), 0.91 (3H, t).

Example 125

{2-[(3,5-Diamino-6-chloro-pyrazine-2-carbonyl)-amino]-ethyl}-bis-{3-[4-(2,3-dihydroxy-propoxy)-phenyl]-propyl}-methyl-ammonium trifluoroacetate The title compound is prepared using an analogous procedure to Example 124 by replacing ((S)-1-{[(3,5-diamino-6-chloro-pyrazine-2-carbonyl)-amino]-methyl}-butyl)-[3-(4-hydroxy-phenyl)-propyl]-dimethyl-ammonium trifluoroacetate (Example 121) with {2-[(3,5-diamino-6-chloro-pyrazine-2-carbonyl)-amino]-ethyl}-bis-[3-(4-hydroxy-phenyl)-propyl]-methyl-ammonium trifluoroacetate (Example 122) and by replacing (S)-glycidol with (±)-glycidol. M⁺ 661.

Example 126

{2-[(3,5-Diamino-6-chloro-pyrazine-2-carbonyl)-amino]-ethyl}-{3-[4-(2,3-dihydroxy-propoxy)-phenyl]-propyl}-dimethyl-ammonium trifluoroacetate The title compound is prepared using an analogous procedure to Example 124 by replacing ((S)-1-{[(3,5-Diamino-6-chloro-pyrazine-2-carbonyl)-amino]-methyl}-butyl)-[3-(4-hydroxy-phenyl)-propyl]-dimethyl-ammonium trifluoroacetate (Example 121) with {2-[(3,5-diamino-6-chloro-pyrazine-2-carbonyl)-amino]-ethyl}-[3-(4-hydroxy-phenyl)-propyl]-dimethyl-ammonium bromide (Example 123), and by replacing (S)-glycidol with (±)-glycidol. M⁺ 467.

Example 127

[3-(4-Benzyloxy-phenyl)-propyl]-{2-[(3,5-diamino-6-chloro-pyrazine-2-carbonyl)-amino]-ethyl}-dimethyl-ammonium trifluoroacetate The title compound is prepared using an analogous procedure to Example 126 by replacing (±)-glycidol with benzyl bromide. M⁺ 483.

Example 128

Carboxymethyl-{2-[(3,5-diamino-6-chloro-pyrazine-2-carbonyl)-amino]-ethyl}-bis-[3-(4-methoxy-phenyl)-propyl]-ammonium chloride Lithium hydroxide (12 mg, 0.28 mmol) is added to a stirred suspension of {2-[(3,5-Diamino-6-chloro-pyrazine-2-carbonyl)-amino]-ethyl}-methoxycarbonylmethyl-bis-[3-(4-methoxy-phenyl)-propyl]-ammonium trifluoroacetate (Example 24) (113 mg, 0.16 mmol) in methanol (9 mL), and the resulting solution is stirred at RT for 3 days. After this time the pH of the solution is adjusted to 1 using 1 N HCl solution, and the solvent then removed in vacuo. The residue is washed with water (10 mL), and dried in vacuo to yield the title compound as an orange solid. M⁺ 585.

Example 129

{2-[(3,5-Diamino-6-chloro-pyrazine-2-carbonyl)-amino]-ethyl}-dimethyl-phenethyl-ammonium trifluoroacetate A suspension of 3,5-Diamino-6-chloro-pyrazine-2-carboxylic acid (2-dimethylamino-ethyl)-amide (Intermediate H) (100 mg, 0.39 mmol) and phenylethyl iodide (280 μl, 1.9 mmol) in acetonitrile (4 mL) is heated in the microwave at 150° C. for 1 h. The solvent is removed in vacuo to afford a brown oil which is purified by reverse phase chromatography (Isolute™ C18, 0-100% acetonitrile in water with 0.1% TFA) to yield the title compound. M⁺ 363. ¹H NMR (400 MHz, DMSO-d₆) δ 8.36 (1H, t), 7.34-7.24 (5H, m), 7.13 (2H, br), 3.66 (2H, t), 3.58-3.50 (4H, m), 3.06-3.02 (2H, m), 3.17 (6H, s).

Example 130

{2-[(3,5-Diamino-6-chloro-pyrazine-2-carbonyl)-amino]-ethyl}-trimethyl-ammonium iodide Methyl iodide (120 μL, 1.9 mmol) is added to a suspension of 3,5-Diamino-6-chloro-pyrazine-2-carboxylic acid (2-dimethylamino-ethyl)-amide (Intermediate H) (100 mg, 0.39 mmol) in DCM (4 mL), and the resultant solution is stirred at RT for 2 h. The white solid which has formed is collected by filtration and washed with DCM (5 mL) to afford the title compound. M⁺ 273. ¹H NMR (400 MHz, DMSO-d₆) δ 8.27 (1H, t), 7.09 (2H, br s), 3.61 (2H, m), 3.45 (2H, t), 3.11 (9H, s).

Example 131

(7-Carbamoyl-heptyl)-{2-[(3,5-diamino-6-chloro-pyrazine-2-carbonyl)-amino]-ethyl}-dimethyl-ammonium bromide A solution of 3,5-Diamino-6-chloro-pyrazine-2-carboxylic acid (2-dimethylamino-ethyl)-amide (Intermediate H) (100 mg, 0.39 mmol) and 8-Bromo-octanoic acid amide (Intermediate P) (130 mg, 0.6 mmol) in DMF (3 mL) is heated at 70° C. for 3 days. After this time, the solvent is removed in vacuo to yield an orange oil, which is triturated with acetone (2×10 mL) to afford the title compound. M$^+$ 400.

Example 132

{2-[(3,5-Diamino-6-chloro-pyrazine-2-carbonyl)-amino]-ethyl}-[3-(4-methoxycarbonylmethoxy-phenyl)-propyl]-dimethyl-ammonium trifluoroacetate and

Example 133

[3-(4-Carboxymethoxy-phenyl)-propyl]-{2-[(3,5-diamino-6-chloro-pyrazine-2-carbonyl)-amino]-ethyl}-dimethyl-ammonium trifluoroacetate Step 1: {4-[3-({2-[(3,5-Diamino-6-chloro-pyrazine-2-carbonyl)-amino]-ethyl}-methyl-amino)-propyl]-phenoxy}-acetic acid methyl ester To a solution of 3,5-Diamino-6-chloro-pyrazine-2-carboxylic acid (2-methylamino-ethyl)-amide (Intermediate E) (0.97 g, 2.7 mmol) and [4-(3-Bromo-propyl)-phenoxy]-acetic acid methyl ester (Intermediate Q) (2.33 g, 8.12 mmol) in acetone (30 mL) is added sodium carbonate (0.86 g, 8.12 mmol), and the reaction is heated at reflux for 4 days. After this time, the reaction is allowed to cool to RT, filtered, and concentrated in vacuo. The residue is purified by reverse phase chromatography (Isolute™ C18, 0-100% acetonitrile in water with 0.1% TFA) to yield {4-[3-({2-[(3,5-Diamino-6-chloro-pyrazine-2-carbonyl)-amino]-ethyl}-methyl-amino)-propyl]-phenoxy}-acetic acid methyl ester. [M+H]$^+$ 451.

Step 2: {2-[(3,5-Diamino-6-chloro-pyrazine-2-carbonyl)-amino]-ethyl}-[3-(4-methoxycarbonylmethoxy-phenyl)-propyl]-dimethyl-ammonium trifluoroacetate and [3-(4-Carboxymethoxy-phenyl)-propyl]-{2-[(3,5-diamino-6-chloro-pyrazine-2-carbonyl)-amino]-ethyl}-dimethyl-ammonium trifluoroacetate To a solution of {4-[3-({2-[(3,5-Diamino-6-chloro-pyrazine-2-carbonyl)-amino]-ethyl}-methyl-amino)-propyl]-phenoxy}-acetic acid methyl ester (0.45 g, 0.79 mmol) in acetone (10 mL) is added sodium carbonate (0.42 g, 3.98 mmol) and methyl iodide (0.24 ml, 3.98 mmol). The reaction is heated at reflux for 3 h, then allowed to cool to RT. The reaction mixture is filtered, and the solid is washed with methanol. The methanol is removed in vacuo and separation by reverse phase column chromatography (Isolute™ C18, 0-100% acetonitrile in water with 0.1% TFA) yields the title compounds.

{2-[(3,5-Diamino-6-chloro-pyrazine-2-carbonyl)-amino]-ethyl}-[3-(4-methoxycarbonylmethoxy-phenyl)-propyl]-dimethyl-ammonium trifluoroacetate (Example 133) M$^+$ 465. $^1$H NMR (400 MHz, DMSO-d$_6$) δ 8.30 (1H, t), 7.95 (2H, br s), 7.10 (2H, d), 6.82 (2H, d), 4.75 (2H, s), 3.60 (2H, t), 3.41 (2H, t), 3.34 (2H, m), 3.07 (6H, s), 2.98 (2H, m), 2.54 (3H, s), 1.94 (2H, m).

[3-(4-Carboxymethoxy-phenyl)-propyl]-{2-[(3,5-diamino-6-chloro-pyrazine-2-carbonyl)-amino]-ethyl}-dimethyl-ammonium trifluoroacetate (Example 134) M$^+$ 451. $^1$H NMR (400 MHz, CD$_3$OD) δ 7.12 (2H, d), 6.85 (2H, d), 4.64 (2H, s), 3.74 (2H, t), 3.51 (2H, t), 3.41-3.38 (2H, m), 3.16 (6H, s), 2.59 (2H, t), 2.10 (2H, m).

Preparation of Intermediate Compounds

Intermediate A 3,5-Diamino-6-chloro-pyrazine-2-carboxylic acid ((S)-2-amino-3-phenyl-propyl)-amide To a solution of 3,5-diamino-6-chloro-pyrazine-2-carboxylic acid (0.225 g, 1.2 mmol) and HATU (0.46 g, 1.2 mmol) in DMF (10 mL) is added N-methylmorpholine (0.53 mL, 4.8 mmol) and ((S)-1-aminomethyl-2-phenyl-ethyl)-carbamic acid tert-butyl ester (0.3 g, 1.2 mmol) and the resulting yellow solution is stirred at RT for 18 h. The solvent is removed in vacuo and the residue is diluted with water (10 mL). The precipitate which forms is collected by filtration and dissolved in DCM (5 mL). TFA (1 mL) is added and the solution stirred at RT for 1 h. The solvent is removed in vacuo, and the residue is purified by reverse phase chromatography (Isolute™ C18, 0-100% acetonitrile in water with 0.1% TFA) to yield the title compound. [M+H]$^+$ 321

Intermediate B ((S)-5-Amino-1-{[(3,5-diamino-6-chloro-pyrazine-2-carbonyl)-amino]-methyl}-pentyl)-carbamic acid tert-butyl ester Step 1: ((S)-5-Benzyloxycarbonylamino-1-{[(3,5-diamino-6-chloro-pyrazine-2-carbonyl)-amino]-methyl}-pentyl)-carbamic acid tert-butyl ester To a solution of 3,5-diamino-6-chloro-pyrazine-2-carboxylic acid (0.39 g, 2.05 mmol) and HATU (0.78 g, 2.05 mmol) in DMF (10 mL) is added N-methylmorpholine (0.83 g, 8.22 mmol) followed by ((S)-1-aminomethyl-5-benzyloxycarbonylamino-pentyl)-carbamic acid tert-butyl ester (prepared according to the procedure described in WO1997/01204 page 20) (750 mg, 2.05 mmol). The resulting solution is stirred at RT for 18 h and then concentrated in vacuo to afford an orange oil. The oil is dissolved in MeOH (10 mL) and allowed to stand at RT after which time a cream precipitate forms that is collected by filtration and dried under vacuum to yield the title compound. [M+H]$^+$ 536.

Step 2: ((S)-5-Amino-1-{[(3,5-diamino-6-chloro-pyrazine-2-carbonyl)-amino]-methyl}-pentyl)-carbamic acid tert-butyl ester A suspension of ((S)-5-benzyloxycarbonylamino-1-{[(3,5-diamino-6-chloro-pyrazine-2-carbonyl)-amino]-methyl}-pentyl)-carbamic acid tert-butyl ester (0.68 g, 1.27 mmol) in EtOH (20 mL) under an inert atmosphere of N2 is treated with activated palladium on charcoal (10%). The reaction mixture is then placed under a positive pressure of hydrogen and stirred at RT. After 3 h, the catalyst is removed by filtration through Celite® (filter material). The filtrate is concentrated in vacuo and the resulting colourless oil is dissolved in MeOH (10 mL) and allowed to stand at RT overnight. A cream precipitate forms which is removed by filtration and the solution is concentrated in vacuo. Purification by reverse phase column chromatography (Isolute™ C18, 0-100% acetonitrile in water with 0.1% $NH_3$) affords the title compound. $[M+H]^+$ 402.

Intermediate C 3,5-Diamino-6-chloro-pyrazine-2-carboxylic acid (2-amino-ethyl)-amide 3,5-Diamino-6-chloro-pyrazine-2-carboxylic acid methyl ester (2.0 g, 9.88 mmol) in neat ethylene diamine (18 mL) is heated using microwave irradiation in a Personal Chemistry Emrys™ Optimizer microwave reactor at 130° C. for 1 h at 4 bar. The solvent is removed in vacuo, water (10 mL) is added to the orange solid and the suspension is then cooled to 0° C. The off-white solid is collected by filtration and dried under vacuum at 50° C. to afford the title compound. $[M+H]^+$ 231.

Intermediate D 3,5-Diamino-6-chloro-pyrazine-2-carboxylic acid (2-{bis-[3-(4-methoxy-phenyl)-propyl]-amino}-ethyl)-amide trifluoroacetate To a solution of 3,5-diamino-6-chloro-pyrazine-2-carboxylic acid (2-amino-ethyl)-amide (Intermediate C) (0.90 g, 3.91 mmol) in acetone (20 mL) is added 1-(3-bromo-propyl)-4-methoxy-benzene (2.30 g, 10.0 mmol) and sodium carbonate (1.04 g, 10.0 mmol). The reaction mixture is heated at 45° C. for 48 h. After cooling to RT the mixture is filtered to remove the inorganic salts and the solvent removed in vacuo. Purification by reverse phase column chromatography (Isolute™ C18, 0-100% acetonitrile in water with 0.1% TFA) affords the title compound. $[M+H]^+$ 527.

Intermediate E 3,5-Diamino-6-chloro-pyrazine-2-carboxylic acid (2-methylamino-ethyl)-amide trifluoroacetate Step 1: {2-[(3,5-Diamino-6-chloro-pyrazine-2-carbonyl)-amino]-ethyl}-methyl-carbamic acid tert-butyl ester A solution of 3,5-diamino-6-chloro-pyrazine-2-carboxylic acid (3.85 g, 20.5 mmol) in DMF (90 mL) is treated with CDI (6.64 g, 41 mmol) and stirred at RT for 1 h. To this mixture is added N-(2-aminoethyl)-N-methyl carbamic acid tert-butyl ester (5.0 g, 28.6 mmol) and stirring continues at RT for 72 h. The solvent is removed in vacuo and the residue is partitioned between EtOAc (100 mL) and water (60 mL). The organic portion is separated, dried ($MgSO_4$) and concentrated in vacuo. The resulting yellow residue is washed with diethyl ether to afford the title compound which is used in the next step without further purification. $[M+H]^+$ 345.

Step 2: 3,5-Diamino-6-chloro-pyrazine-2-carboxylic acid (2-methylamino-ethyl)-amide trifluoroacetate A mixture comprising {2-[(3,5-diamino-6-chloro-pyrazine-2-carbonyl)-amino]-ethyl}-methyl-carbamic acid tert-butyl ester in DCM:TFA (60 mL of a 5:1 DCM/TFA solution) is stirred at RT for 3 h. The solvent is removed in vacuo and the resulting yellow oil is dissolved in water with heating. Any undissolved material is removed by filtration and the filtrate is concentrated in vacuo to afford the title compound. $[M+H]^+$ 245.

Intermediate F 3,5-Diamino-6-chloro-pyrazine-2-carboxylic acid {2-[(4-amino-butyl)-methyl-amino]-ethyl}-amide trifluoroacetate Step 1

[4-({2-[(3,5-Diamino-6-chloro-pyrazine-2-carbonyl)-amino]-ethyl}-methyl-amino)-butyl]-carbamic acid tert-butyl ester To a mixture comprising 3,5-diamino-6-chloro-pyrazine-2-carboxylic acid (2-methylamino-ethyl)-amide (Intermediate E) (0.5 g, 2.0 mmol) and 4-(Boc-amino)butyl bromide (0.8 g, 3.1 mmol) in DMF (5 mL) is added sodium carbonate (0.4 g, 4.0 mmol). The resulting mixture is heated at reflux for 3 h and then allowed to cool to RT, filtered and concentrated in vacuo. The crude product is dissolved in DCM and filtered to remove any undissolved impurities. The filtrate is concentrated in vacuo to yield the title compound which is used in the next step without further purification.

Step 2: 3,5-Diamino-6-chloro-pyrazine-2-carboxylic acid {2-[(4-amino-butyl)-methyl-amino]-ethyl}-amide

[4-({2-[(3,5-Diamino-6-chloro-pyrazine-2-carbonyl)-amino]-ethyl}-methyl-amino)-butyl]-carbamic acid tert-butyl ester (0.54 g, 2.2 mmol) in DCM (10 mL) and TFA (2 mL) is stirred at RT for 1 h. The solvent is removed in vacuo and the resulting oil is dissolved in saturated aqueous sodium carbonate solution. The mixture is concentrated in vacuo and the residue is dissolved in MeOH and filtered to remove the sodium carbonate. The filtrate is concentrated in vacuo to afford the title compound. $[M+H]^+$ 316

Intermediate G

1-Ethoxy-2-chloro-4-isocyanato-benzene

1-Ethoxy-2-chloro-4-isocyanato-benzene is prepared by addition of triethylamine to a solution of 4-ethoxy-3-chlorophenylamine in EtOAc at 0-5° C. Triphosgene is added and the reaction mixture is slowly heated to reflux over 2 h. The solvent is removed in vacuo and the crude product is filtered through silica to afford the title compound.

Intermediate H 3,5-Diamino-6-chloro-pyrazine-2-carboxylic acid (2-dimethylamino-ethyl)-amide 3,5-Diamino-6-chloro-pyrazine-2-carboxylic acid methyl ester (25.0 g, 0.12 mol) and N,N-dimethylethylenediamine (100 mL) are heated at 100° C. in a miniclave for 20 h. The reaction mixture is concentrated in vacuo and the pale yellow crystals that form are collected by filtration, washed with MeOH and dried under vacuum to afford the title compound. [M+H]$^+$ 259.

Intermediate I 1-(2-Chloro-ethyl)-3-(4-isobutoxy-phenyl)-urea

A solution of 2-chloroethyl isocyanate (15 g, 142 mmols) is added dropwise to a solution of 4-isobutoxy phenylamine (20 g, 121 mmols) in diethyl ether (100 mL) and stirred at RT for 1 h. The solid formed is collected by filtration and recrystallisation from ethanol affords the title compound.

Intermediate J (S)-3-(4-{3-[4-(3-Bromo-propyl)-phenoxy]-propyl}-phenoxy)-propane-1,2-diol Step 1: (5)-3-[4-(3-Hydroxy-propyl)-phenoxy]-propane-1,2-diol To a solution of 3-(4-hydroxyphenyl)-1-propanol (15.0 g, 99 mmol) in acetone (300 mL) is added S-(−)-glycidol (10.0 g, 105 mmol) and potassium carbonate (20.0 g, 145 mmol) and the reaction mixture is heated at reflux for 24 h. The resulting mixture is allowed to cool to RT, filtered and the filtrate is concentrated in vacuo. Purification by column chromatography (SiO$_2$, 0-4% MeOH in DCM) affords the product as a white solid. [M+H]$^+$ 227.

Step 2: 3-[4-((R)-2,2-Dimethyl-[1,3]-dioxolan-4-ylmethoxy)-phenyl]-propan-1-ol

To a solution of (S)-3-[4-(3-hydroxy-propyl)-phenoxy]-propane-1,2-diol (6.5 g, 28.7 mmol) in anhydrous DMF (100 mL) is added 2,2-dimethoxypropane (15.0 mL, 122.0 mmol) and pyridinium p-toluenesulfonate (0.75 g, 2.98 mmol). The reaction mixture is stirred at RT for 16 h and then concentrated in vacuo. The residue is dissolved in EtOAc and the organic portion is washed with 10% aqueous NaHCO$_3$ solution, water, brine and dried over Na$_2$SO$_4$. The solvent is removed in vacuo and the crude product is purified by column chromatography (SiO$_2$, EtOAc in petroleum ether, gradient 0-30% EtOAc) to obtain the title compound as a colourless oil. [M+H]$^+$ 267.

Step 3: (R)-4-(4-{3-[4-(3-Bromo-propyl)-phenoxy]-propyl}-phenoxymethyl)-2,2-dimethyl-11,31-dioxolane To a mixture of 3-[4-((R)-2,2-dimethyl-[1,3]-dioxolan-4-ylmethoxy)-phenyl]-propan-1-ol (6.2 g, 23.3 mmol), 4-(3-bromo-propyl)-phenol (prepared according to the procedure described in WO2006/097744, page 30) (5.0 g, 23.3 mmol) and triphenylphosphine (6.1 g, 23.3 mmol) in DCM (75 mL) at 0° C. is added DEAD (3.7 mL, 23.5 mmol) dropwise and the resulting mixture is stirred at RT overnight. The solvent is removed in vacuo and the residue is triturated with diethyl ether. The precipitated solid is removed by filtration and the filtrate is concentrated in vacuo. Purification of the crude residue by column chromatography (SiO$_2$, EtOAc in petroleum ether, gradient 0-4% EtOAc) affords the title compound as white solid.

Step 4: (S)-3-(4-{3-[4-(3-Bromo-propyl)-phenoxy]-propyl}-phenoxy)-propane-1,2-diol To a solution of (R)-4-(4-{3-[4-(3-bromo-propyl)-phenoxy]-propyl}-phenoxymethyl)-2,2-dimethyl-[1,3]dioxolane (5.0 g, 10.8 mmol) in DCM (50 mL) is added TFA (2.0 mL, 26.9 mmol) dropwise followed by water (2.0 mL) and the reaction mixture is stirred at RT overnight. The solvent is removed in vacuo and the residue is treated with aqueous sodium hydrogen carbonate solution. The mixture is extracted with EtOAc (3×200 mL) and the combined organic portions are washed with water, brine, dried over Na$_2$SO$_4$ and concentrated in vacuo. Recrystallizisation of the residue from diethyl ether-hexane affords the title compound as white solid.

Intermediate K (2-Amino-ethyl)-{2-[(3,5-diamino-6-chloro-pyrazine-2-carbonyl)-amino]-ethyl}-dimethyl-ammonium bromide Step 1: {2-[(3,5-Diamino-6-chloro-pyrazine-2-carbonyl)-amino]-ethyl}-[2-(1,3-dioxo-1,3-dihydro-isoindol-2-yl)-ethyl]-dimethyl-ammonium bromide The title compound is prepared analogously to Example 27 by replacing 1-(3-bromo-propyl)-4-methoxy-benzene with N-(4-bromoethyl)-phthalimide.

Step 2: (2-Amino-ethyl)-{2-[(3,5-diamino-6-chloro-pyrazine-2-carbonyl)-amino]-ethyl}-dimethyl-ammonium bromide A mixture of {2-[(3,5-diamino-6-chloro-pyrazine-2-carbonyl)-amino]-ethyl}-[2-(1,3-dioxo-1,3-dihydro-isoindol-2-yl)-ethyl]-dimethyl-ammonium bromide (47 g, 92 mmol) and hydrazine monohydrate (20 mL, 412 mmol) in EtOH (500 mL) is heated at 40° C. for 4 h. After cooling to RT the resulting solid is removed by filtration and washed with diethyl ether. The filtrate is concentrated in vacuo to afford the title product. [M+H]$^+$ 302.

Intermediate L

3-[3-(Diaminomethylene-sulfamoyl)-4-methoxy-phenyl]-3-phenyl-propionic acid

Step 1:
3-(4-Methoxy-3-sulfo-phenyl)-3-phenyl-propionic acid methyl ester

To a solution of 3-(4-methoxy-phenyl)-3-phenyl-propionic acid methyl ester (prepared according to the procedure reported in Tetrahedron (2006), 62(41), 9610-9621) (2.50 g, 9.25 mmol) in DCM (250 mL) at 0° C. is added chlorosulfonic acid (30.7 ml, 462.5 mmol). The reaction mixture is allowed to warm to RT and is stirred at this temperature for 2 h. Ice water is added to cause precipitation of the product. The solvents are decanted and the residual solid is washed with ice water. The solid is then dried under vacuum to afford the title compound that is used without further purification.

Step 2: 3-(3-Chlorosulfonyl-4-methoxy-phenyl)-3-phenyl-propionic acid methyl ester To a solution of 3-(4-methoxy-3-sulfo-phenyl)-3-phenyl-propionic acid methyl ester (850 mg, 2.43 mmol) in 1,3-dimethyl-2-imidazolidinone (25 mL) is added POCl$_3$ (0.57 ml, 6.06 mmol) and pyridine (0.33 mL, 4.13 mmol). The reaction mixture is stirred at RT for 1 h. After this time, water (50 mL) is added and the reaction mixture is extracted with DCM (3×50 mL). The combined organic phases are washed with brine (30 mL) then dried over MgSO$_4$, filtered and concentrated in vacuo to afford the title compound as an oil.

Step 3: 3-[3-(Diaminomethylene-sulfamoyl)-4-methoxy-phenyl]-3-phenyl-propionic acid methyl ester To a solution of 3-(3-chlorosulfonyl-4-methoxy-phenyl)-3-phenyl-propionic acid methyl ester (500 mg, 1.36 mmol) in DCM (50 mL) is added triethylamine (0.57 ml, 4.08 mmol) and guanidine hydrochloride (0.14 g, 1.50 mmol). The reaction mixture is stirred at RT overnight, then diluted with DCM (100 mL). The reaction mixture is washed with an aqueous saturated solution of NaHCO$_3$ (30 mL), water (30 mL) then brine (30 mL). The organic phase is then dried over MgSO$_4$, filtered and concentrated in vacuo. Purification of the residue by reverse phase chromatography (Isolute™ C18, 0-100% acetonitrile in water with 0.1% TFA) affords the title compound.

Step 4: 3-[3-(Diaminomethylene-sulfamoyl)-4-methoxy-phenyl]-3-phenyl-propionic acid To a solution of 3-[3-(diaminomethylene-sulfamoyl)-4-methoxy-phenyl]-3-phenyl-propionic acid methyl ester (400 mg, 1.02 mmol) in a mixture of MeOH and water (30 mL of 1:1 solution) is added LiOH (73 mg, 3.06 mmol). The reaction mixture is stirred at RT overnight. 1 M aqueous HCl is added to neutralise the reaction mixture. The resulting solid is collected by filtration and dried under vacuum to afford the title compound that is used without further purification.

Intermediate M (3-Amino-propyl)-{2-[(3,5-diamino-6-chloro-pyrazine-2-carbonyl)-amino]-ethyl}-dimethyl-ammonium bromide The title compound is prepared by an analogous procedure to (2-amino-ethyl)-{2-[(3,5-diamino-6-chloro-pyrazine-2-carbonyl)-amino]-ethyl}-dimethyl-ammonium bromide (Intermediate K) by replacing N-(4-bromoethyl)-phthalimide with N-(4-bromopropyl)-phthalimide. M$^+$ 316.

Intermediate N (4-Amino-butyl)-{2-[(3,5-diamino-6-chloro-pyrazine-2-carbonyl)-amino]-ethyl}-dimethyl-ammonium bromide The title compound is prepared by an analogous procedure to (2-amino-ethyl)-{2-[(3,5-diamino-6-chloro-pyrazine-2-carbonyl)-amino]-ethyl}-dimethyl-ammonium bromide (Intermediate K) by replacing N-(4-bromoethyl)-phthalimide with N-(4-bromobutyl)-phthalimide. M$^+$ 330.

Intermediate O (5-Amino-pentyl)-{2-[(3,5-diamino-6-chloro-pyrazine-2-carbonyl)-amino]-ethyl}-dimethyl-ammonium bromide The title compound is prepared by an analogous procedure to (2-amino-ethyl)-{2-[(3,5-diamino-6-chloro-pyrazine-2-carbonyl)-amino]-ethyl}-dimethyl-ammonium bromide (Intermediate K) by replacing N-(4-bromoethyl)-phthalimide with N-(4-bromopentyl)-phthalimide.

Intermediate P

8-Bromo octanamide

The title compound is prepared as described in 'Ortho esters with 2,4,10-Trioxa admanatane Structure as Carboxyl Protecting Groups; Applications in the Synthesis of Substituted Carboxylic Acids by Means of Grignard Reagents', G. Voss and H. Gerlach, Helvetica Chimica Acta, 1983, 66, 2294-2307, p 2300

Intermediate Q

[4-(3-Bromo-propyl)-phenoxy]-acetic acid methyl ester

Step 1: [4-(3-Hydroxy-propyl)-phenoxy]-acetic acid methyl ester

To a solution of 3-(4-hydroxyphenyl)-1-propanol (3 g, 19.7 mmol) in acetone (30 mL) is added potassium carbonate (4.08 g, 29.5 mmol) and methyl bromoacetate (2.8 mL, 29.3 mmol) and the reaction is heated at reflux for 15 h. The reaction mixture is allowed to cool to RT, filtered, and the solvent removed in vacuo. The residue is purified by chromatography (SiO$_2$, EtOAc:iso-hexane, 2:3) to afford the title compound. $^1$H NMR (400 MHz, CDCl$_3$) δ 7.14 (2H, d), 6.85 (2H, d), 4.64 (2H, s), 3.82 (3H, s), 3.69 (2H, t), 2.68 (2H, t), 1.82 (2H, m).

Step 2: [4-(3-Bromo-propyl)-phenoxy]-acetic acid methyl ester

To a solution of [4-(3-Hydroxy-propyl)-phenoxy]-acetic acid methyl ester (2.45 g, 10.9 mmol) in DCM (60 mL) is added polymer-supported triphenylphosphine (7.26 g, 21.8 mmol) and carbon tetrabromide (3.47 g, 11.99 mmol) and the resulting reaction mixture is stirred at RT for 15 h. The reaction mixture is filtered to remove the polymer-supported reagent, and then concentrated in vacuo. The residue is purified by chromatography (SiO$_2$, EtOAc:iso-hexane, 1:5) to yield the title compound. $^1$H NMR (400 MHz, CDCl$_3$) δ 7.14 (2H, d), 6.86 (2H, d), 4.69 (2H, s), 3.83 (3H, s), 3.40 (2H, t), 2.74 (2H, t), 2.15 (2H, m).

The invention claimed is:
1. A compound of Formula I:

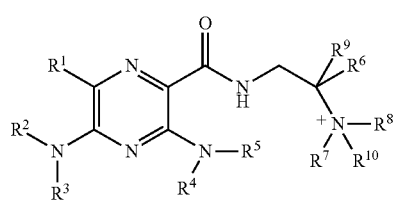

wherein
R$^1$ is halogen;
R$^2$, R$^3$, R$^4$ and R$^5$ are each independently selected from H and C$_1$-C$_6$ alkyl;
R$^6$ is —(C$_0$-C$_6$ alkylene)-R$^{6a}$, wherein the alkylene linker is optionally substituted by one or more groups selected from C$_1$-C$_3$ alkyl, halo and OH;

$R^{6a}$ is selected from H, a $C_3$-$C_{10}$ carbocyclic group, $NR^{11}R^{12}$, $C(O)NR^{13}R^{14}$, aryl, heteroaryl, heterocyclyl and a group of the formula P—$(CH_2)_m$-Q, wherein each of the ring systems is optionally substituted by one or more substituents selected from the List Z;

P is selected from a bond, —O—, —C(O)—, —C(O)O—, —NHC(=N)NH— and —S(O$_2$)—, —S(O$_2$)NR$^a$—, —NR$^a$C(O)—, —NR$^a$C(O)O—, —NR$^a$S(O$_2$)— and —NR$^a$C(O)NR$^b$—;

$R^a$ and $R^b$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

Q is selected from H, $C_1$-$C_6$ alkyl, a $C_3$-$C_{10}$ carbocyclic group, aryl, heteroaryl and heterocyclyl, wherein the carbocyclic, aryl, heteroaryl and heterocyclyl groups are each optionally substituted by one or more substituents selected from List Z;

m is 0, 1, 2 or 3;

$R^7$, $R^8$ and $R^{10}$ are each independently selected from $C_1$-$C_6$ alkyl, $C_2$-$C_6$ alkenyl, $C_2$-$C_6$ alkynyl, a $C_3$-$C_{10}$ carbocyclic group, —($C_1$-$C_3$ alkylene)-$C_3$-$C_{10}$ carbocyclic group, aryl, heteroaryl, heterocyclyl or a group of the formula $(CH_2)_a$-A-$(CH_2)_b$—B, wherein the carbocyclic, aryl, heteroaryl and heterocyclyl groups are each optionally substituted by one or more substituents selected from List Z; and wherein the alkyl and alkylene groups are optionally substituted by one or more halogen atoms, OH groups or phenyl groups; or $R^7$ and $R^8$, together with the nitrogen atom to which they are attached form a 4- to 10-membered nitrogen-containing heterocyclic group which is optionally substituted by one or more substituents selected from the List Z; or $R^6$ and $R^8$, together with the atoms to which they are attached form a 4- to 10-membered nitrogen-containing heterocyclic group which is optionally substituted by one or more substituents selected from the List Z;

A is selected from a bond, —O—, —C(O)—, —C(O)NR$^c$—, —C(O)O—, —OC(O)—, —NHC(=N)NH—, —S(O$_2$)—, —S(O$_2$)NR$^c$—, —NR$^c$C(O)—, —NR$^c$C(O)O—, —OC(O)NR$^c$—, —NR$^c$S(O$_2$)—, —C(O)NR$^c$S(O$_2$)—, —NR$^c$C(O)NR$^d$—, —NR$^c$—, -aryl-, —$C_3$-$C_{10}$ carbocyclyl-, -heteroaryl-, -heterocyclyl-, -aryl-O—, —O-aryl-, —O—$C_3$-$C_{10}$ carbocyclyl- and —$C_3$-$C_{10}$ carbocyclyl-O—, wherein the aryl, carbocyclyl, heteroaryl and heterocyclyl groups are each optionally substituted by one or more substituents selected from List Z;

B is selected from H, $C_1$-$C_6$ alkyl, a $C_3$-$C_{10}$ carbocyclic group, $NR^xR^y$, $C(O)OR^z$, aryl, heteroaryl and heterocyclyl, wherein the carbocyclic, aryl, heteroaryl and heterocyclyl groups are each optionally substituted by one or more substituents selected from List Z;

d is 1, 2, 3, 4, 5, 6 or 7;

b is 0, 1, 2 or 3;

$R^c$, $R^d$, $R^x$ and $R^y$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

$R^z$ is H or $C_1$-$C_6$ alkyl;

$R^9$ is H or $C_1$-$C_6$ alkyl; or $R^6$ and $R^9$, together with the carbon atom to which they are attached, form a $C_3$-$C_{10}$ carbocyclic group or a 4- to 10-membered heterocyclyl group, wherein each of the ring systems is optionally substituted by one or more substituents selected from the List Z;

$R^{11}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{12}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —C(O)$C_1$-$C_6$ alkyl, —C(O)$C_3$-$C_{10}$ carbocyclic, —C(O)($C_1$-$C_3$ alkylene)-$C_3$-$C_{10}$ carbocyclic, —C(O)$(CH_2)_x$ aryl, —C(O)$(CH_2)_x$ heteroaryl, —C(O)$(CH_2)_x$ heterocyclyl, —C(O)Oalkyl, C(O)Oaryl, $(CH_2)_x$ aryl, $(CH_2)_x$ heteroaryl and —$(CH_2)_x$ heterocyclyl, wherein each of the ring systems is optionally substituted by one or more substituents selected from the List Z;

$R^{13}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{14}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —$(CH_2)_z$ aryl, $(CH_2)_z$ heteroaryl and $(CH_2)_z$ heterocyclyl, wherein each of the ring systems is optionally substituted by one or more substituents selected from the List Z;

x is 0, 1, 2 or 3;

z is 0, 1, 2 or 3;

each Z is independently selected from OH, aryl, heteroaryl, heterocyclyl, benzyl, $C_1$-$C_6$ alkyl optionally substituted by one or more halogen atoms, CN or OH groups, $C_1$-$C_6$ alkoxy optionally substituted by one or more halogen atoms, CN or OH groups, -Oaryl, -Obenzyl, —O$(CH_2)_a$ C(O)E, $NR^{15}(SO_2)R^{17}$, $(SO_2)NR^{15}R^{16}$, $(SO_2)R^{18}$, $NR^{15}C(O)R^{17}$, $C(O)NR^{15}R^{17}$, $NR^{15}C(O)NR^{16}R^{17}$, $NR^{15}C(O)OR^{17}$, $NR^{15}R^{17}$, $C(O)OR^{15}$, $OC(O)R^{15}$, $OC(O)NR^{15}$, $C(O)R^{17}$, $SR^{15}$, CN, $NO_2$, and halogen; and when there are two or more Z substitutents, two Z substituents together with the atoms to which they are attached optionally form a 5- to 7-membered carbocyclic or a 4- to 7-membered heterocyclic substituent fused to the ring system;

a is 0, 1, 2, 3 or 4, where the alkylene group is optionally substituted by OH or $NH_2$ when a is 1, 2, 3 or 4;

E is $NR^{15}R^{17}$ or $OR^{17}$;

each $R^{15}$ and $R^{16}$ is independently selected from H, $C_1$-$C_6$ alkyl, a $C_3$-$C_{10}$ carbocyclic group and —($C_1$-$C_3$ alkylene)-$C_3$-$C_{10}$ carbocyclic;

each $R^{17}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl and heterocyclyl, where each of the ring systems is optionally substituted by OH, halo, $C_1$-$C_3$ alkyl and $C_1$-$C_3$ alkoxy; and $R^{18}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl, heterocyclyl and $NHC(=NH)NH_2$, where each of the ring systems is optionally substituted by OH, halo, $C_1$-$C_3$ alkyl and $C_1$-$C_3$ alkoxy.

2. The compound according to claim 1 having the formula Ia

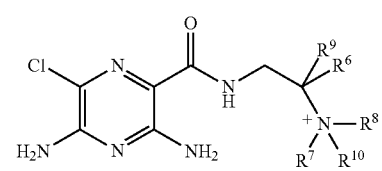

wherein $R^6$ is —($C_0$-$C_6$ alkylene)-$R^{6a}$, wherein the alkylene linker is optionally substituted by one or more groups selected from $C_1$-$C_3$ alkyl, halo and OH;

$R^{6a}$ is selected from H, a $C_3$-$C_{10}$ carbocyclic group, $NR^{11}R^{12}$, $C(O)NR^{13}R^{14}$, aryl, heteroaryl, heterocyclyl and a group of the formula P—$(CH_2)_m$-Q, wherein each of the ring systems is optionally substituted by one or more substituents selected from the List Z;

P is selected from a bond, —O—, —C(O)—, —C(O)O—, —NHC(=N)NH— and —S(O$_2$)—, —S(O$_2$)NR$^a$—, —NR$^a$C(O)—, —NR$^a$C(O)O—, —NR$^a$S(O$_2$)— and —NR$^a$C(O)NR$^b$—;

$R^a$ and $R^b$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

Q is selected from H, $C_1$-$C_6$ alkyl, a $C_3$-$C_{10}$ carbocyclic group, aryl, heteroaryl and heterocyclyl, wherein the carbocyclic, aryl, heteroaryl and heterocyclyl groups are each optionally substituted by one or more substituents selected from List Z;

m is 0, 1, 2 or 3;

$R^7$, $R^8$ and $R^{10}$ are each independently selected from $C_1$-$C_6$ alkyl, $C_2$-$C_6$ alkenyl, $C_2$-$C_6$ alkynyl, a $C_3$-$C_{10}$ carbocyclic group, —($C_1$-$C_3$ alkylene)-$C_3$-$C_{10}$ carbocyclic group, aryl, heteroaryl, heterocyclyl or a group of the formula $(CH_2)_d$-A-$(CH_2)_b$—B, wherein the carbocyclic, aryl, heteroaryl and heterocyclyl groups are each optionally substituted by one or more substituents selected from List Z; and wherein the alkyl and alkylene groups are optionally substituted by one or more halogen atoms, OH groups or phenyl groups; or $R^7$ and $R^8$, together with the nitrogen atom to which they are attached form a 4- to 10-membered nitrogen-containing heterocyclic group which is optionally substituted by one or more substituents selected from the List Z; or $R^6$ and $R^8$, together with the atoms to which they are attached form a 4- to 10-membered nitrogen-containing heterocyclic group which is optionally substituted by one or more substituents selected from the List Z;

A is selected from a bond, —O—, —C(O)—, —C(O)NR$^c$—, —C(O)O—, —OC(O)—, —NHC(=N)NH—, —S(O$_2$)—, —S(O$_2$)NR$^c$—, —NR$^c$C(O)—, —NR$^c$C(O)O—, —OC(O)NR$^c$—, —NR$^c$S(O$_2$)—, —C(O)NR$^c$S(O$_2$)—, —NR$^c$C(O)NR$^d$—, —NR$^c$—, -aryl-, —$C_3$-$C_{10}$ carbocyclyl-, -heteroaryl-, -heterocyclyl-, -aryl-O—, —O-aryl-, —O—$C_3$-$C_{10}$ carbocyclyl- and —$C_3$-$C_{10}$ carbocyclyl-O—, wherein the aryl, carbocyclyl, heteroaryl and heterocyclyl groups are each optionally substituted by one or more substituents selected from List Z;

B is selected from H, $C_1$-$C_6$ alkyl, a $C_3$-$C_{10}$ carbocyclic group, $NR^xR^y$, $C(O)OR^z$, aryl, heteroaryl and heterocyclyl, wherein the carbocyclic, aryl, heteroaryl and heterocyclyl groups are each optionally substituted by one or more substituents selected from List Z;

d is 1, 2, 3, 4, 5, 6 or 7;

b is 0, 1, 2 or 3;

$R^c$, $R^d$, $R^x$ and $R^y$ are each independently selected from H, $C_1$-$C_6$ alkyl, a $C_3$-$C_{10}$ carbocyclic group and —($C_1$-$C_3$ alkylene)-$C_3$-$C_{10}$ carbocyclic;

$R^z$ is H or $C_1$-$C_6$ alkyl;

$R^9$ is H or $C_1$-$C_6$ alkyl; or $R^6$ and $R^9$, together with the carbon atom to which they are attached, form a $C_3$-$C_{10}$ carbocyclic group or a 4- to 10-membered heterocyclyl group, wherein each of the ring systems is optionally substituted by one or more substituents selected from the List Z;

$R^{11}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{12}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —C(O)$C_1$-$C_6$ alkyl, —C(O)$C_3$-$C_{10}$ carbocyclic, —C(O)($C_1$-$C_3$ alkylene)-$C_3$-$C_{10}$ carbocyclic, —C(O)(CH$_2$)$_x$ aryl, —C(O)(CH$_2$)$_x$ heteroaryl, —C(O)(CH$_2$)$_x$ heterocyclyl, —C(O)Oalkyl, C(O)Oaryl, (CH$_2$)$_x$ aryl, (CH$_2$)$_x$ heteroaryl and —(CH$_2$)$_x$ heterocyclyl, wherein each of the ring systems is optionally substituted by one or more substituents selected from the List Z;

$R^{13}$ is selected from H, $C_1$-$C_6$ alkyl, a $C_3$-$C_{10}$ carbocyclic group and —($C_1$-$C_3$ alkylene)-$C_3$-$C_{10}$ carbocyclic;

$R^{14}$ is selected from H, $C_1$-$C_6$ alkyl, a $C_3$-$C_{10}$ carbocyclic group, —($C_1$-$C_3$ alkylene)-$C_3$-$C_{10}$ carbocyclic, —(CH$_2$)$_z$ aryl, (CH$_2$)$_z$ heteroaryl and (CH$_2$)$_z$ heterocyclyl, wherein each of the ring systems is optionally substituted by one or more substituents selected from the List Z;

x is 0, 1, 2 or 3;

z is 0, 1, 2 or 3;

each Z is independently selected from OH, aryl, heteroaryl, heterocyclyl, benzyl, $C_1$-$C_6$ alkyl optionally substituted by one or more halogen atoms, CN or OH groups, $C_1$-$C_6$ alkoxy optionally substituted by one or more halogen atoms, CN or OH groups, -Oaryl, -Obenzyl, —O(CH$_2$)$_a$C(O)E, $NR^{15}(SO_2)R^{17}$, $(SO_2)NR^{15}R^{16}$, $(SO_2)R^{18}$, $NR^{15}C(O)R^{17}$, $C(O)NR^{15}R^{17}$, $NR^{15}C(O)NR^{16}R^{17}$, $NR^{15}C(O)OR^{17}$, $NR^{15}R^{17}$, $C(O)OR^{15}$, $OC(O)R^{15}$, $OC(O)NR^{15}$, $C(O)R^{17}$, $SR^{15}$, CN, $NO_2$, and halogen; and when there are two or more Z substitutents, two Z substituents together with the atoms to which they are attached optionally form a 5- to 7-membered carbocyclic or a 4- to 7-membered heterocyclic substituent fused to the ring system;

a is 0, 1, 2, 3 or 4, where the alkylene group is optionally substituted by OH or NH$_2$ when a is 1, 2, 3 or 4;

E is $NR^{15}R^{17}$ or $OR^{17}$;

each $R^{15}$ and $R^{16}$ is independently selected from H, $C_1$-$C_6$ alkyl, a $C_3$-$C_{10}$ carbocyclic group and —($C_1$-$C_3$ alkylene)-$C_3$-$C_{10}$ carbocyclic;

each $R^{17}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl and heterocyclyl, where each of the ring systems is optionally substituted by OH, halo, $C_1$-$C_3$ alkyl and $C_1$-$C_3$ alkoxy; and $R^{18}$ is selected from H, $C_1$-$C_6$ alkyl, a $C_3$-$C_{10}$ carbocyclic group, —($C_1$-$C_3$ alkylene)-$C_3$-$C_{10}$ carbocyclic, aryl, heteroaryl, heterocyclyl and NHC(=NH)NH$_2$, where each of the ring systems is optionally substituted by OH, halo, $C_1$-$C_3$ alkyl and $C_1$-$C_3$ alkoxy.

3. The compound according to claim 1, wherein $R^9$ is H.

4. The compound according to claim 1, wherein $R^9$ is H and $R^6$ is selected from H and $C_1$-$C_6$ alkyl.

5. The compound according to claim 1, which is selected from:
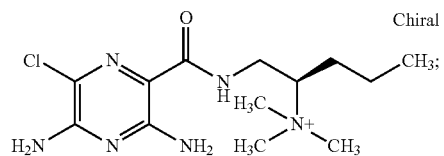
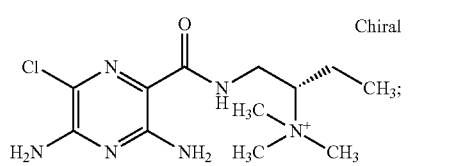
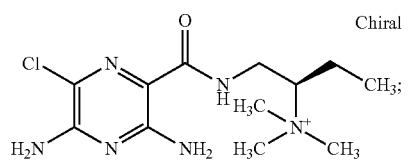
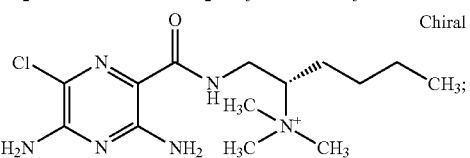
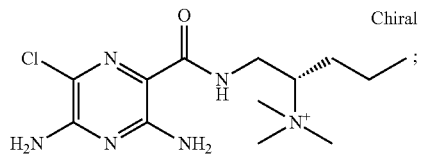
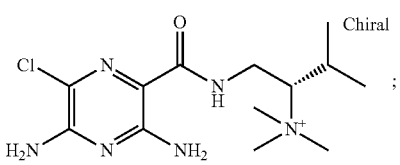
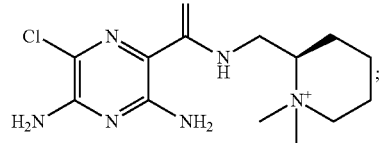
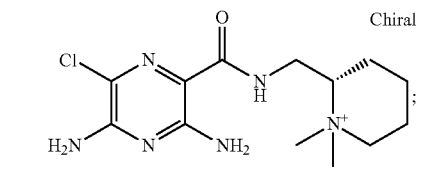
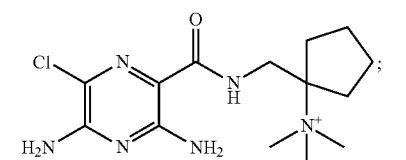
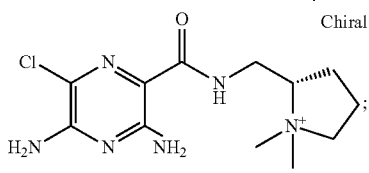
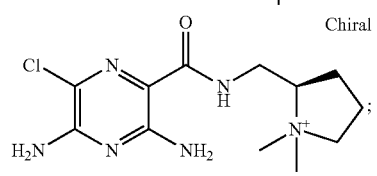
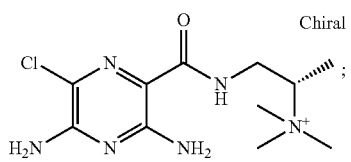
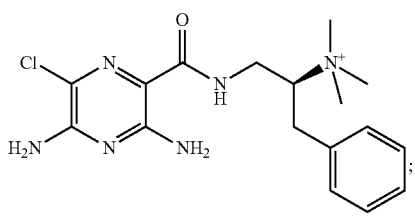
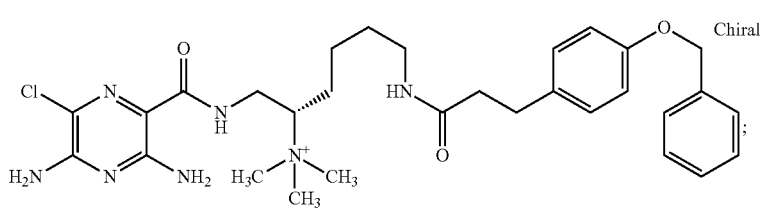
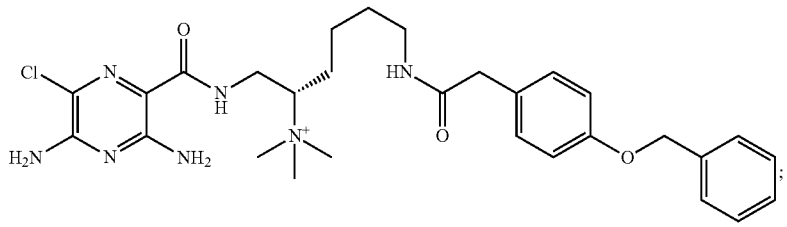

-continued
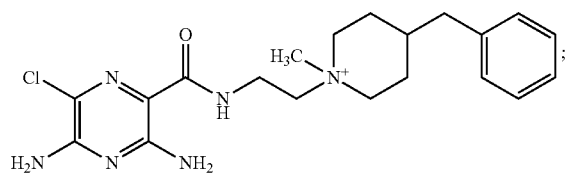
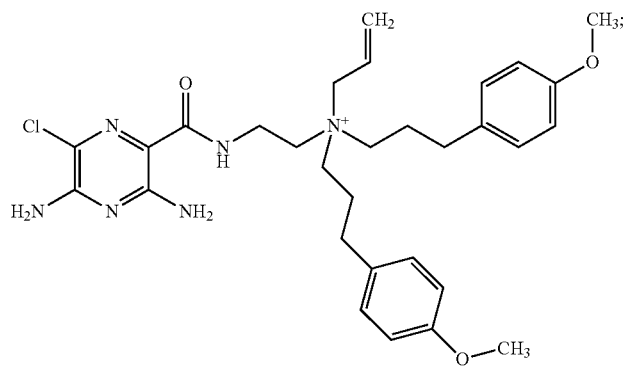
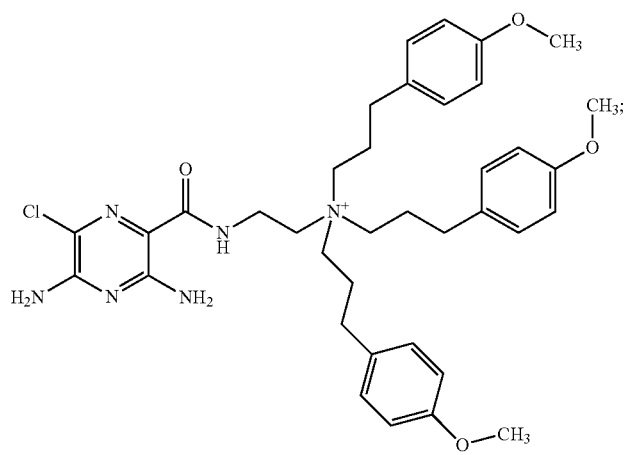
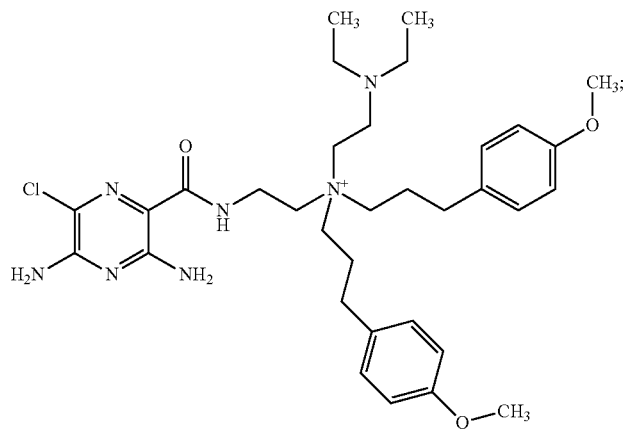

-continued
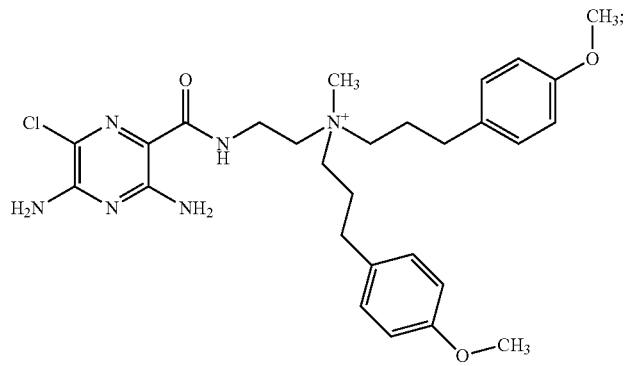
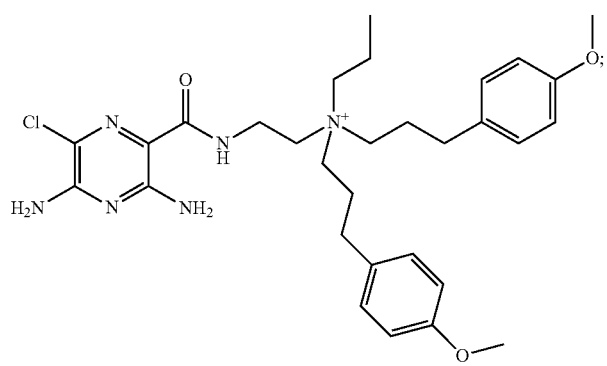
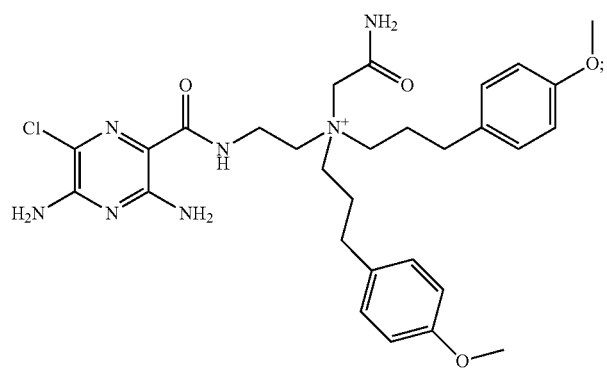
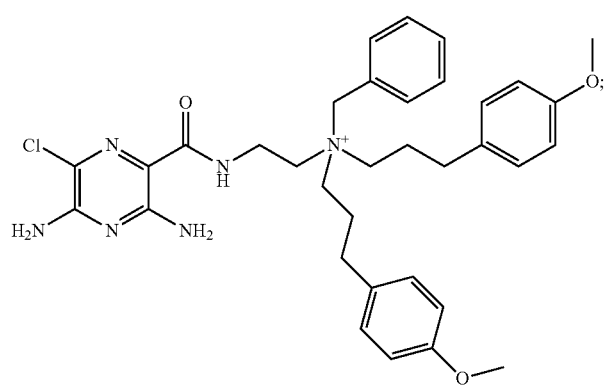

-continued
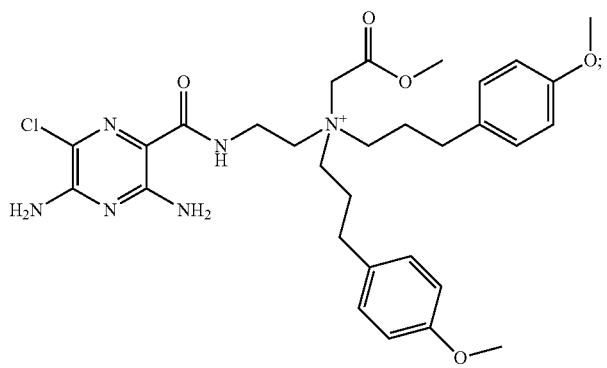
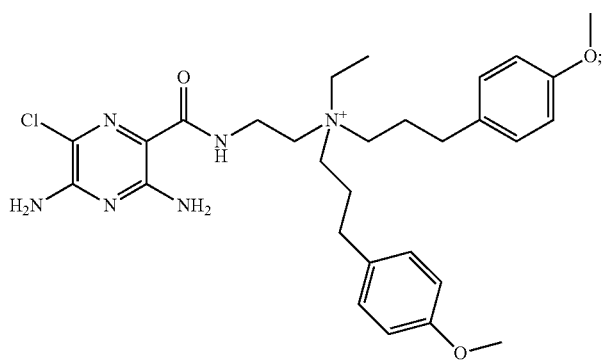
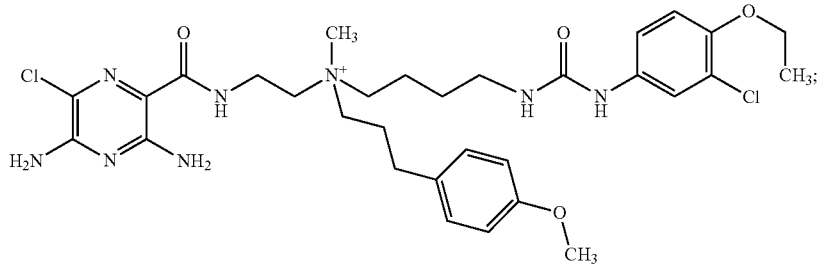
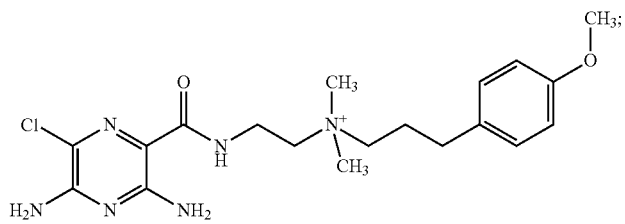
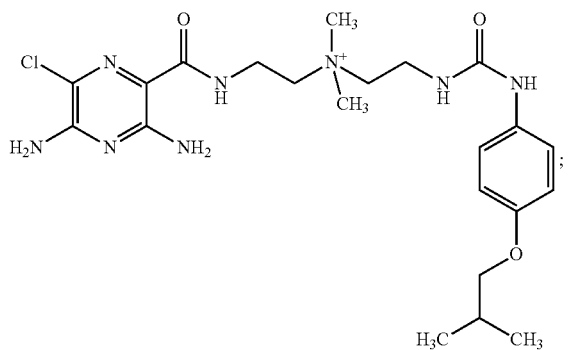

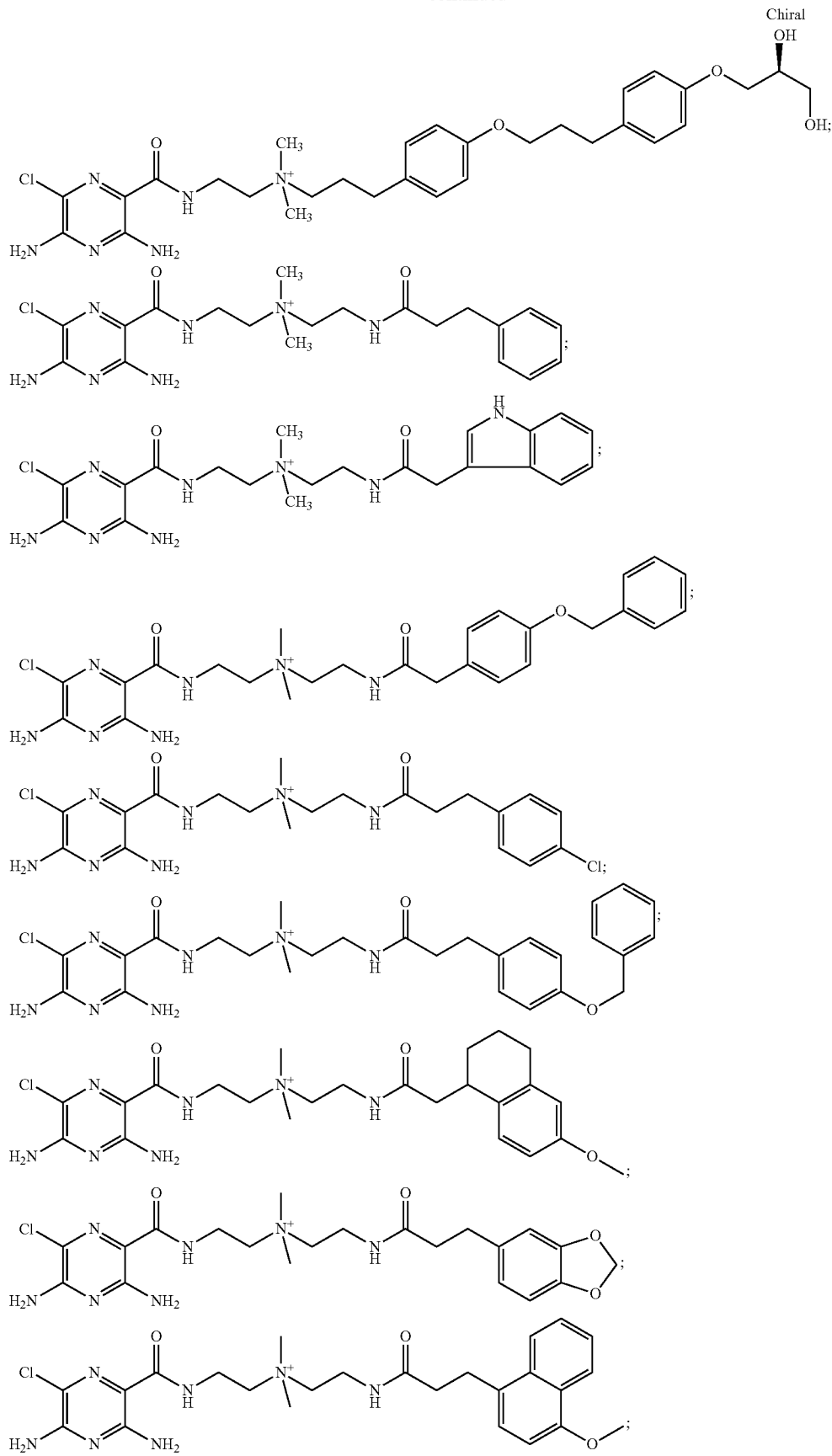

-continued
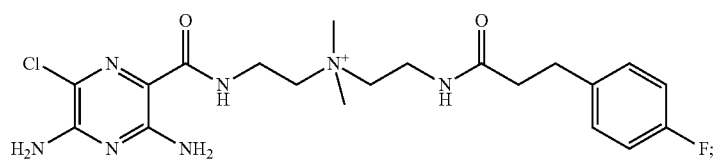
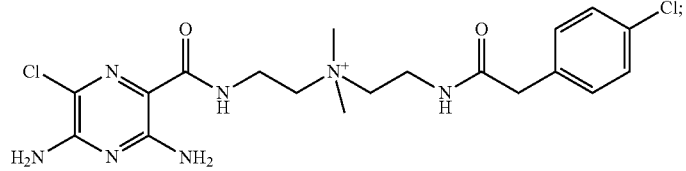
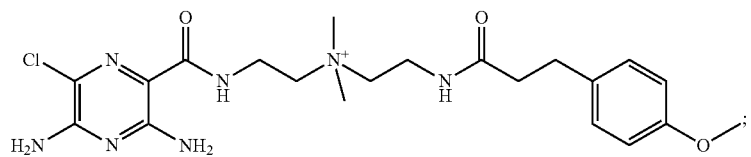
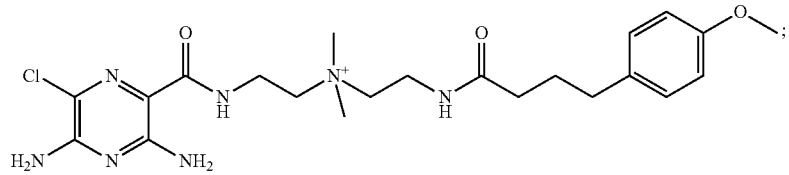
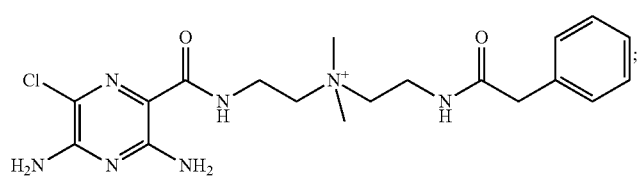
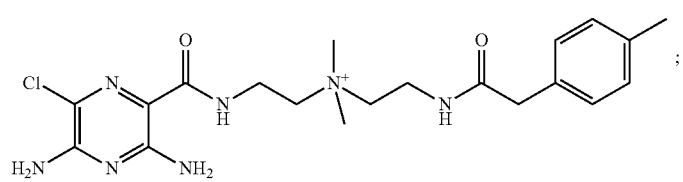
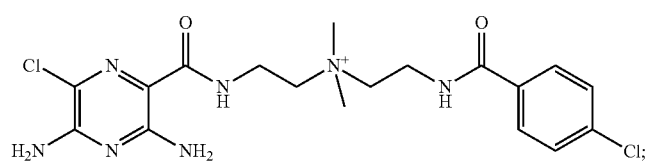
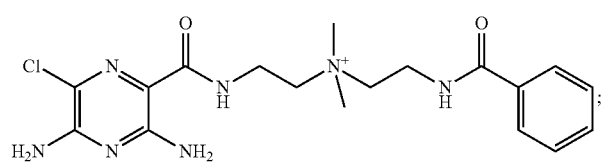
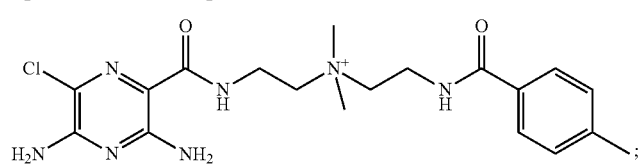
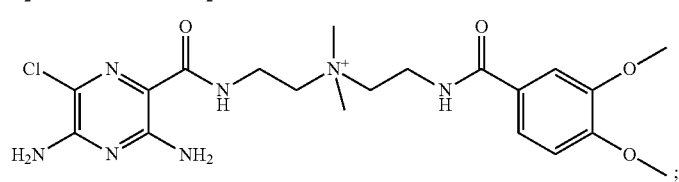

-continued
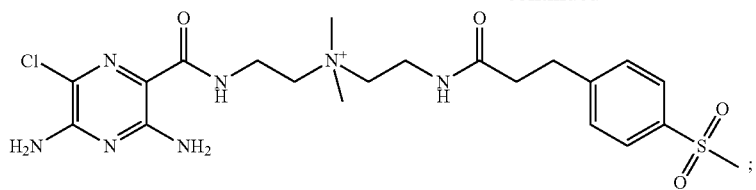
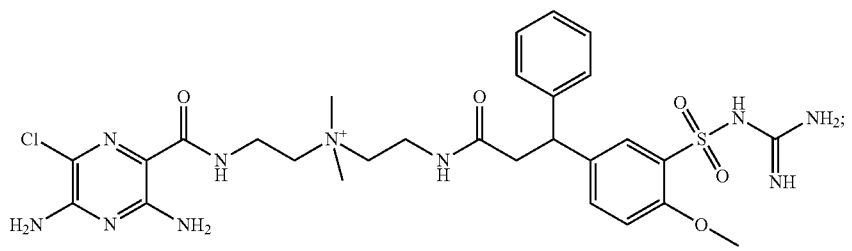
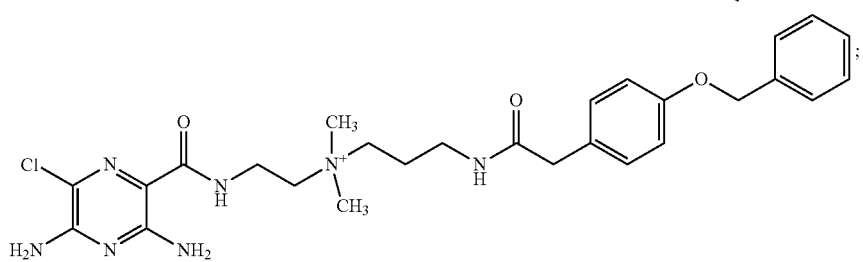
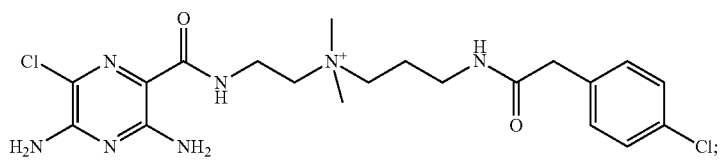
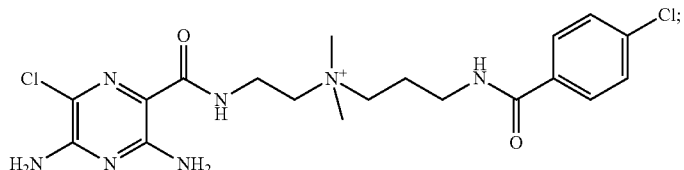
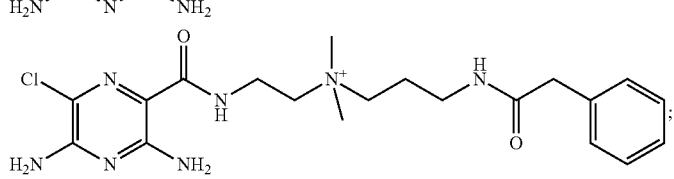
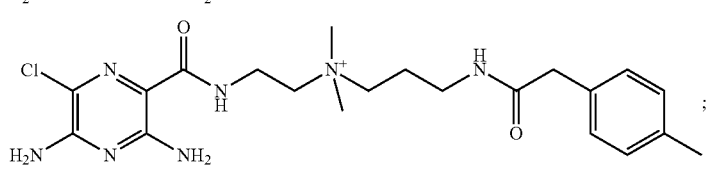
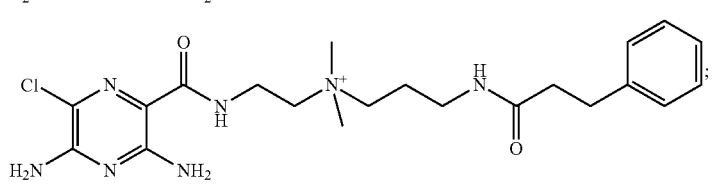
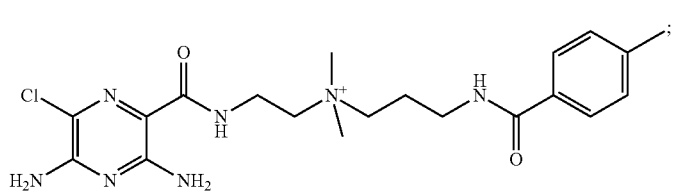

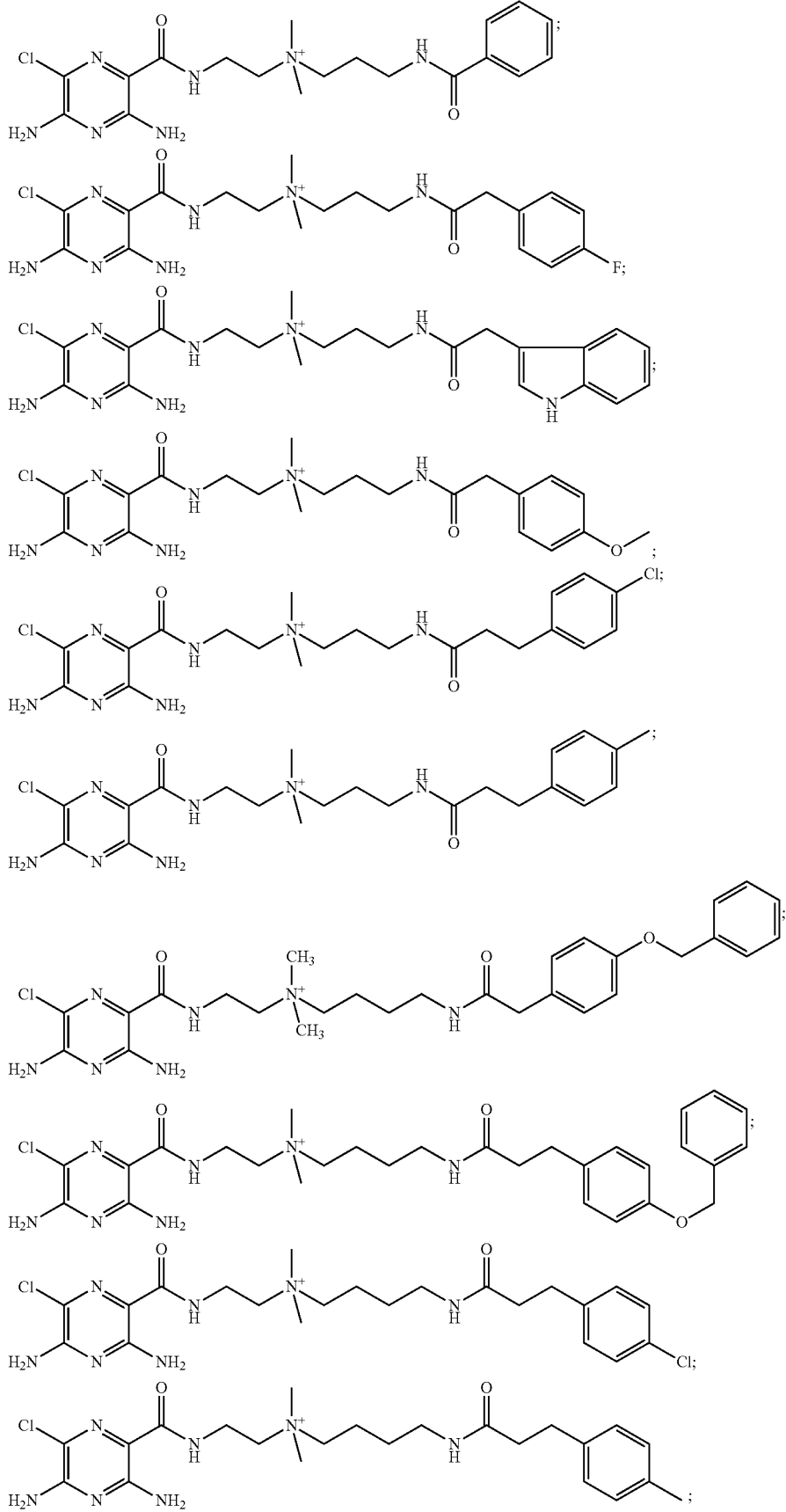

-continued
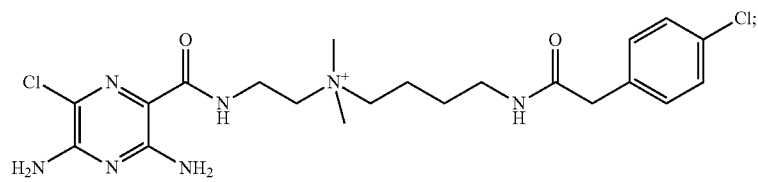
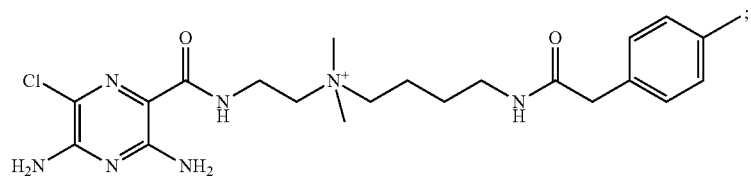
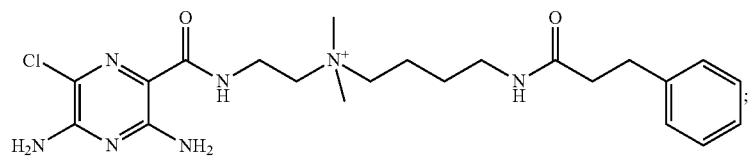
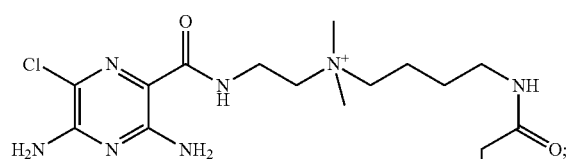
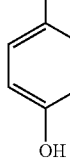
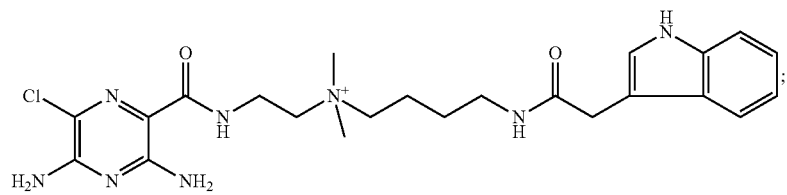
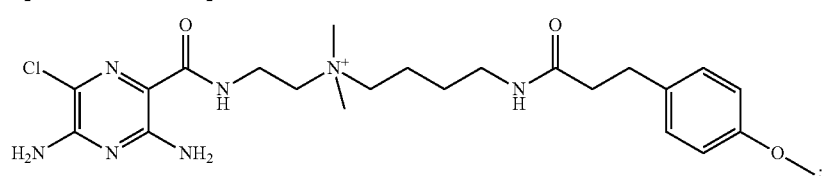
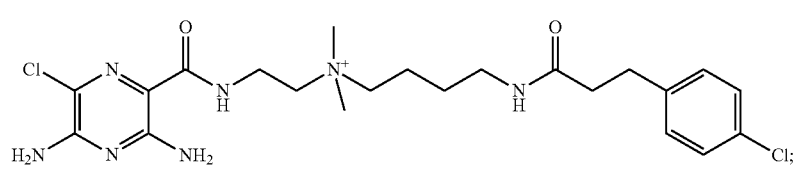
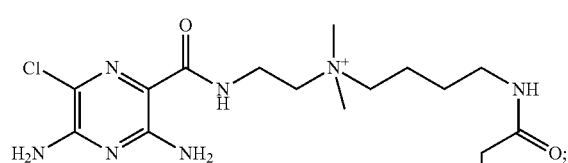
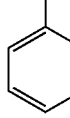

-continued
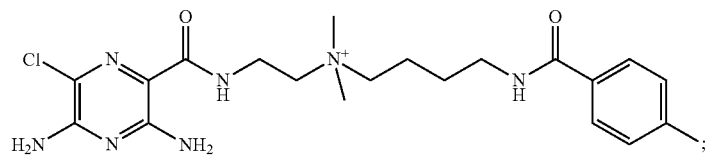
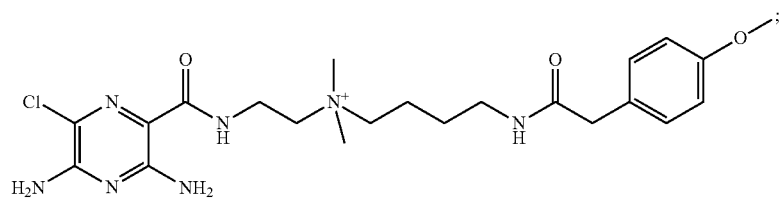
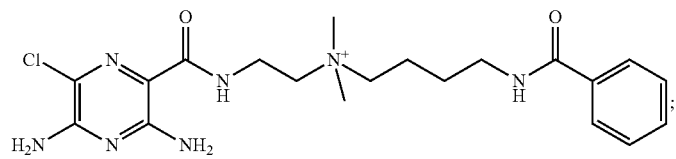
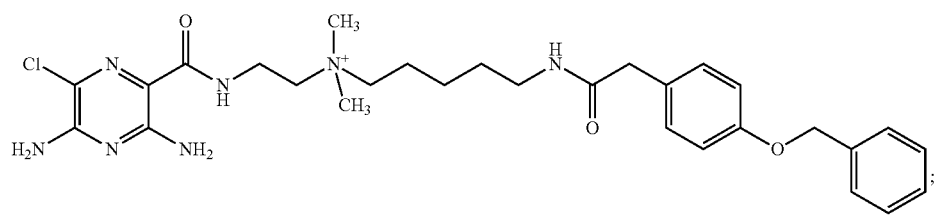
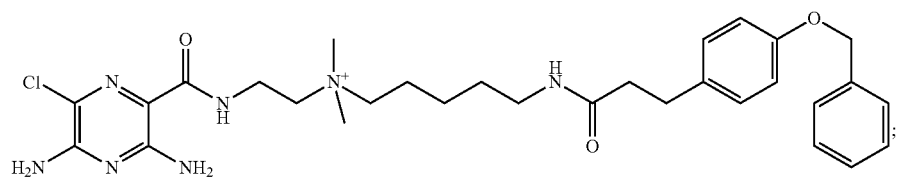
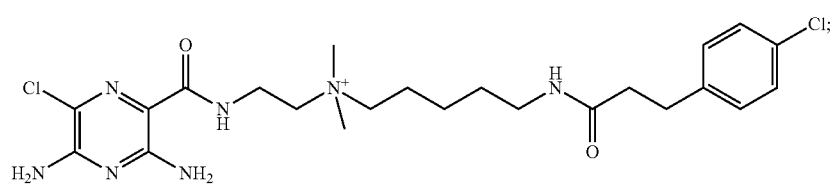
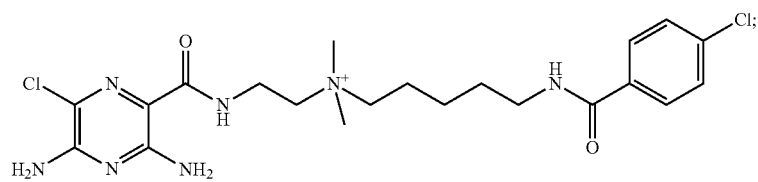
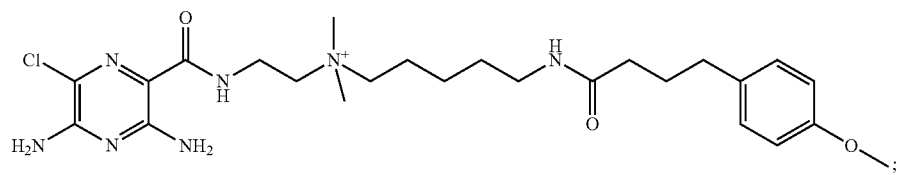
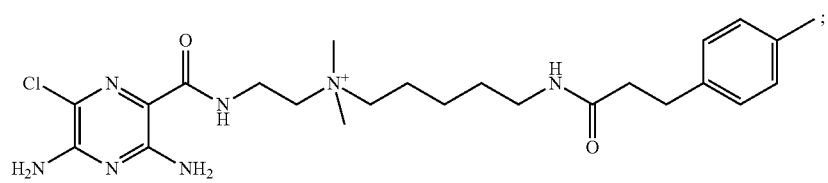

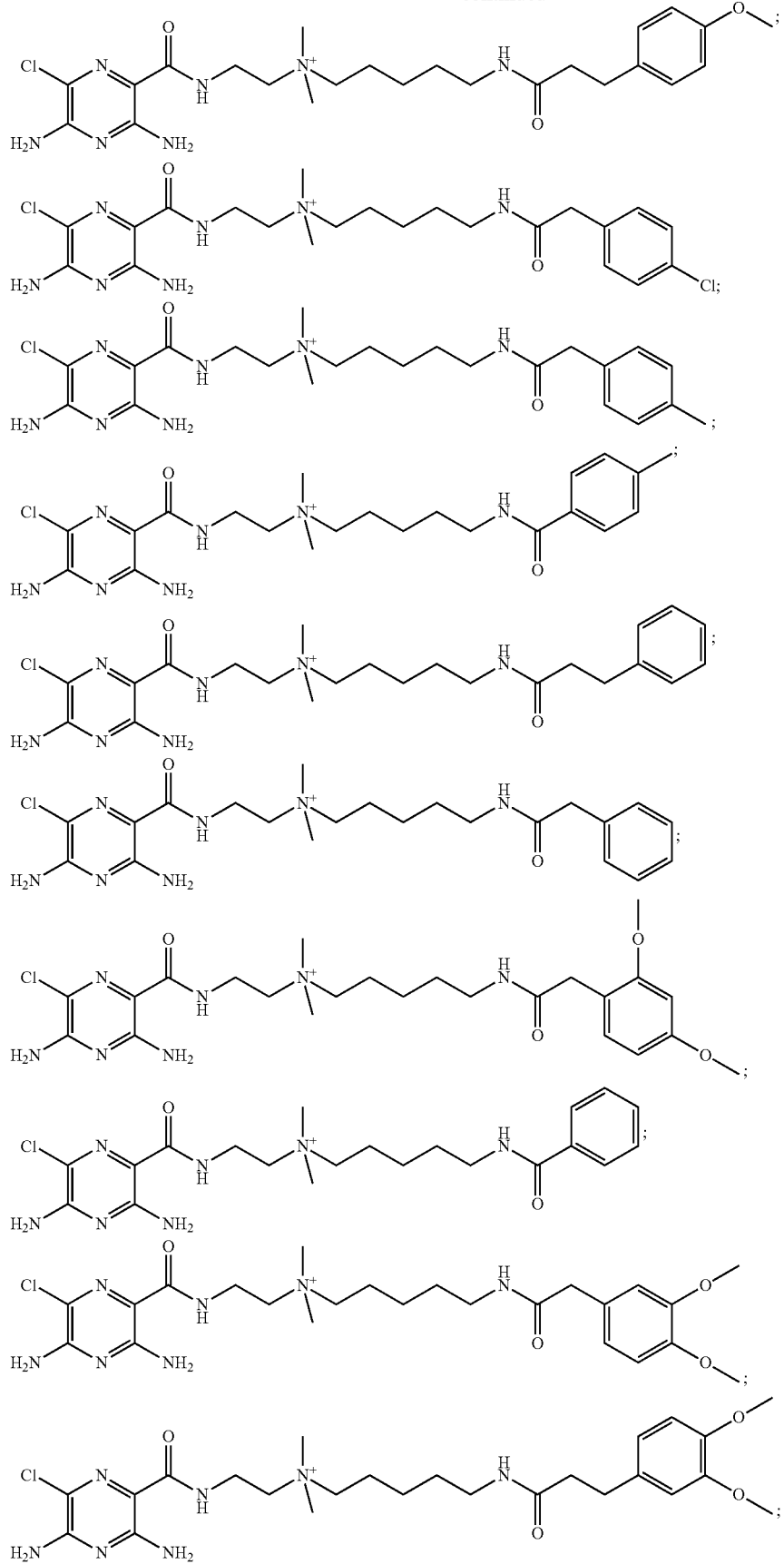

-continued
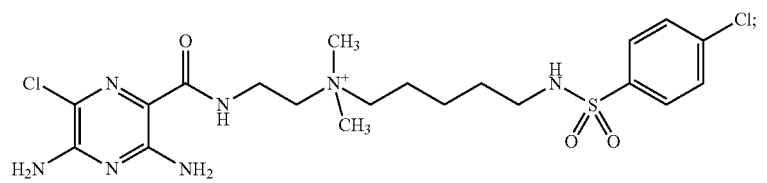
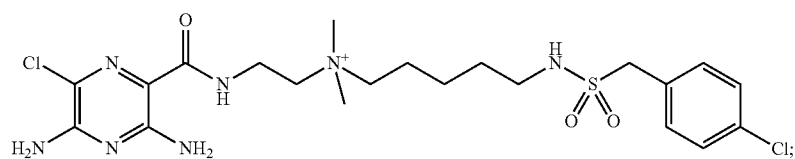
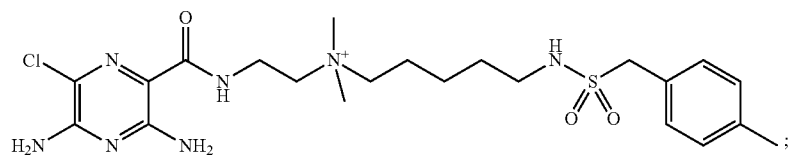
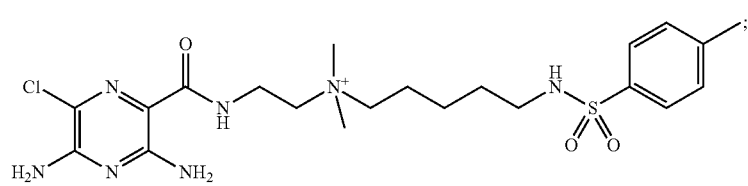
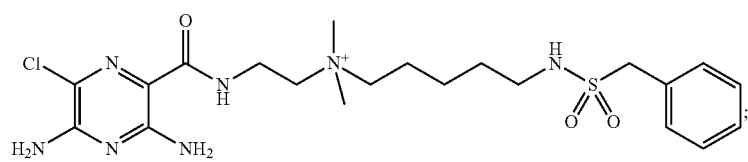
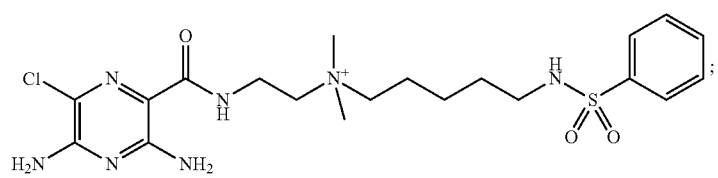
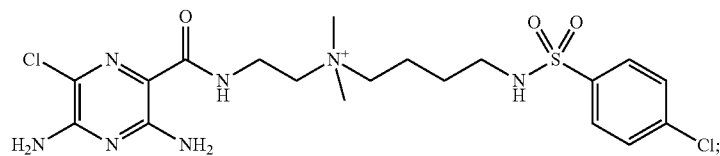
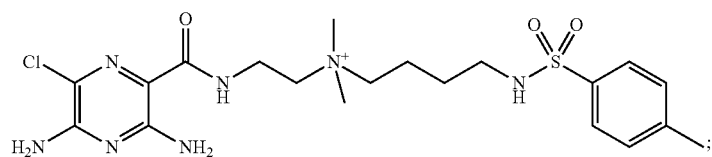
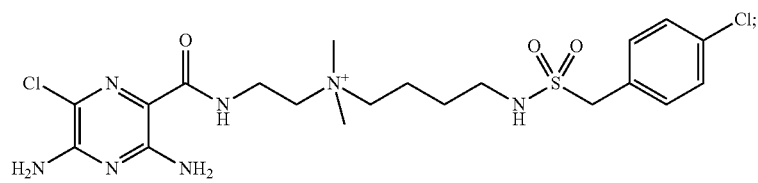
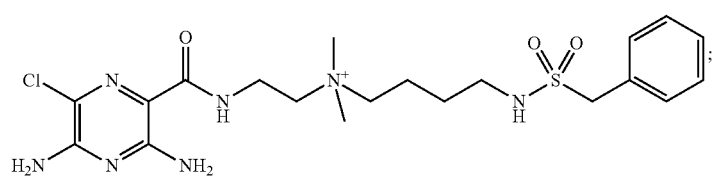

-continued
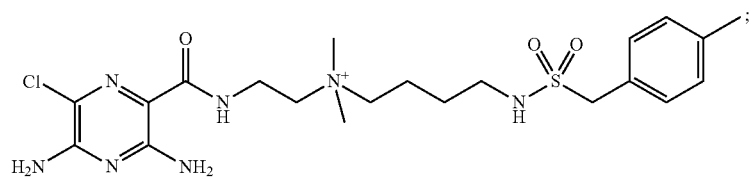
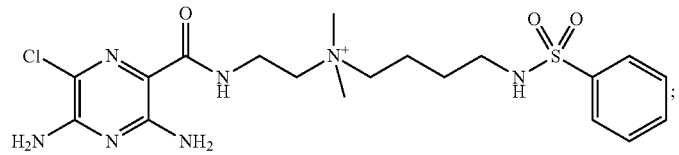
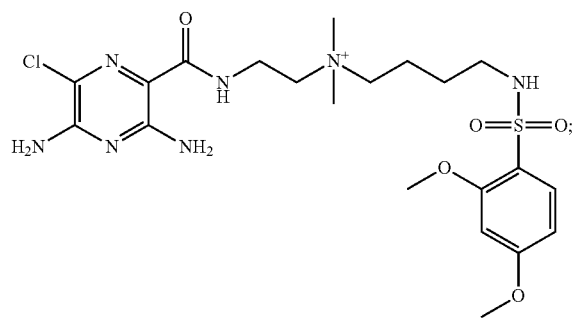
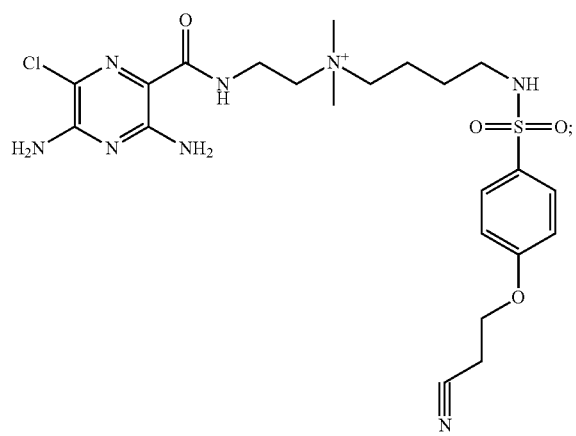
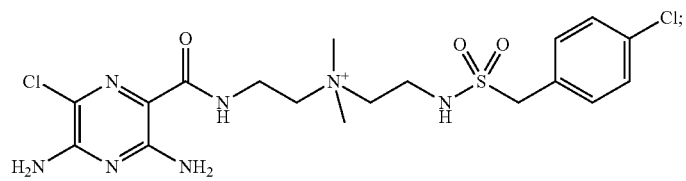
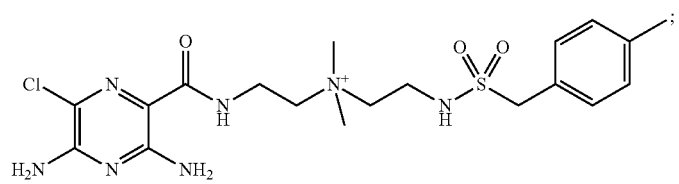
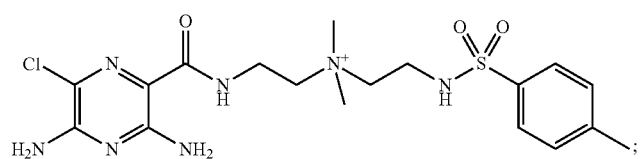

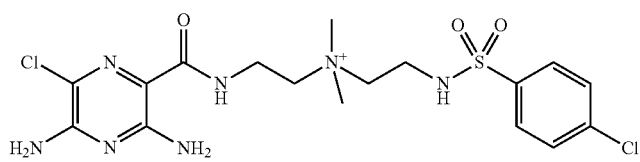
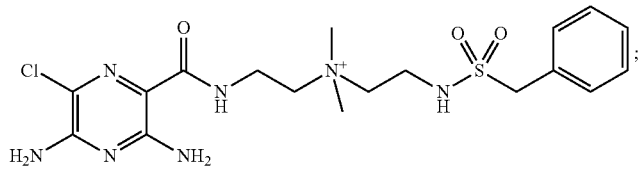
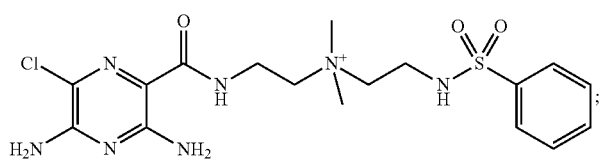
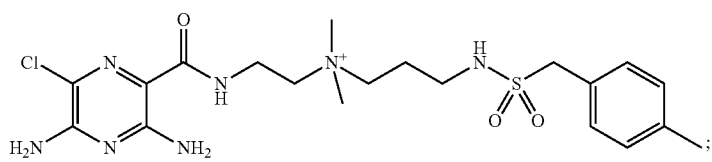
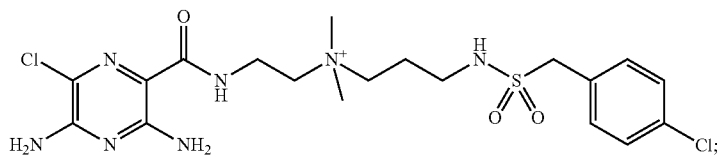
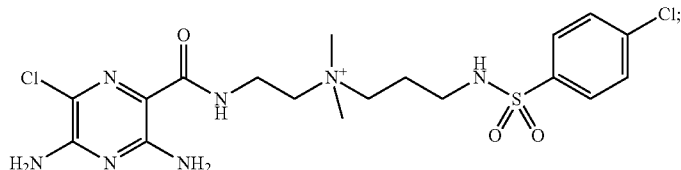
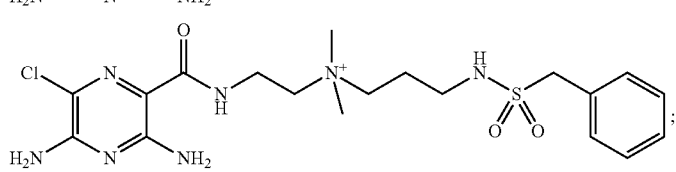
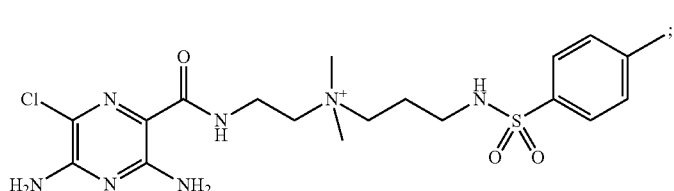
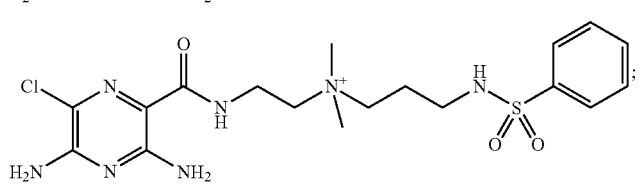
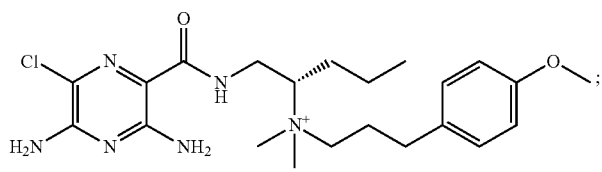

-continued
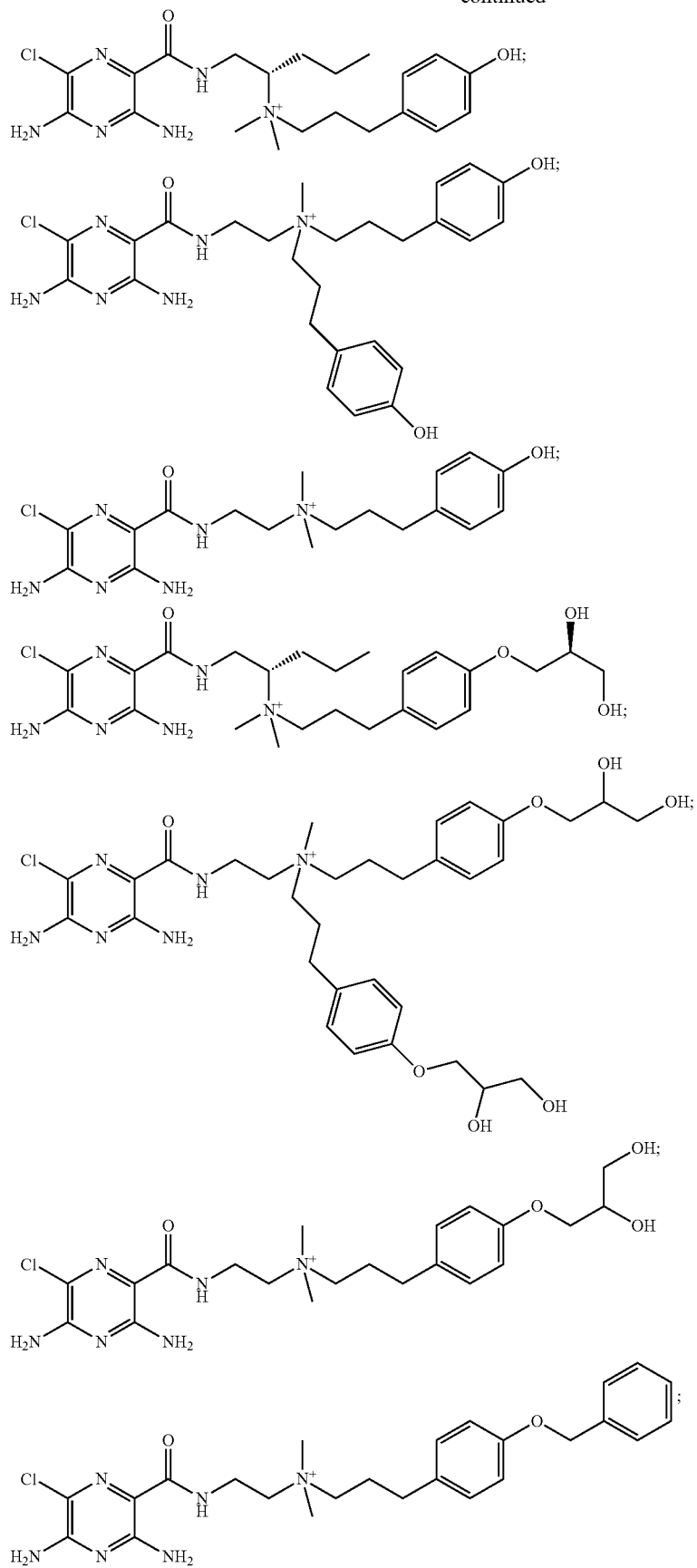

-continued

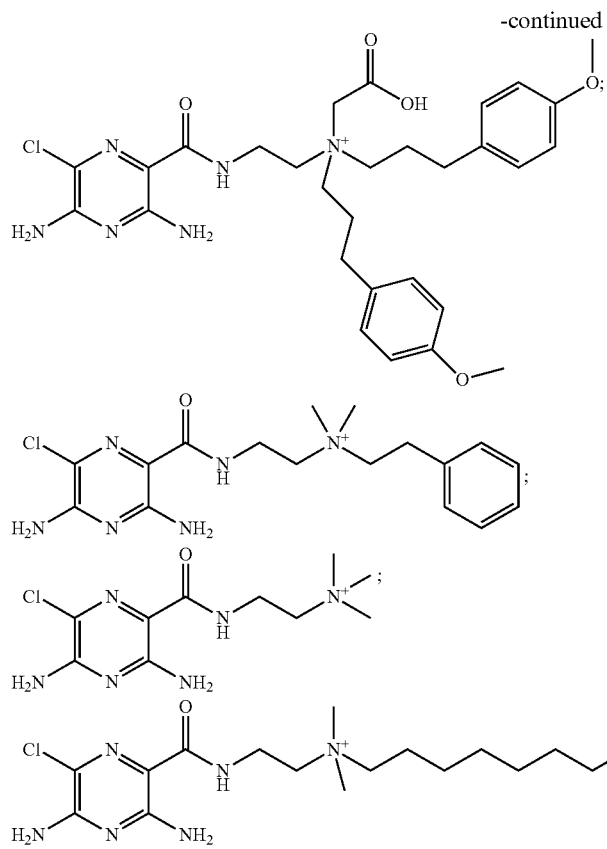

6. A pharmaceutical composition, comprising:
the compound according to claim 1, together with one or more pharmaceutical excipients.

7. A method to treat cystic fibrosis, comprising:
administering to a subject in need thereof an effective amount of the compound of claim 1.

8. A pharmaceutical composition, comprising:
the compound according to claim 1 and
an anti-inflammatory, bronchodilatory, antihistamine or anti-tussive drug substance.

* * * * *